(12) United States Patent
Ayvali et al.

(10) Patent No.: US 11,660,147 B2
(45) Date of Patent: May 30, 2023

(54) ALIGNMENT TECHNIQUES FOR PERCUTANEOUS ACCESS

(71) Applicant: AURIS HEALTH, INC., Redwood City, CA (US)

(72) Inventors: Elif Ayvali, Redwood City, CA (US); Bulat Ibragimov, Copenhagen (DK); Sarah Plewe, Redwood City, CA (US); Janet Zhen Bone, San Mateo, CA (US); Miroslav Drahos, Freehold, NJ (US); Yuriy Malinin, Palo Alto, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 17/131,117

(22) Filed: Dec. 22, 2020

(65) Prior Publication Data
US 2021/0196399 A1    Jul. 1, 2021

Related U.S. Application Data

(60) Provisional application No. 62/956,019, filed on Dec. 31, 2019.

(51) Int. Cl.
*A61B 34/30* (2016.01)
*A61B 34/20* (2016.01)

(52) U.S. Cl.
CPC .............. *A61B 34/20* (2016.02); *A61B 34/30* (2016.02); *A61B 2034/2051* (2016.02); *A61B 2034/2068* (2016.02); *A61B 2034/301* (2016.02)

(58) Field of Classification Search
CPC ......... A61B 34/37; A61B 34/30; A61B 34/20; A61B 2034/2051; A61B 2034/301; A61B 17/3403; A61B 19/201; A61B 19/203; A61B 19/5244; A61B 2034/2068
See application file for complete search history.

(56) References Cited

U.S. PATENT DOCUMENTS

| 4,644,237 A | 2/1987 | Frushour et al. |
| 4,745,908 A | 5/1988 | Wardle |
| 4,748,969 A | 6/1988 | Wardle |

(Continued)

FOREIGN PATENT DOCUMENTS

| CN | 1364275 A | 8/2002 |
| CN | 1511249 A | 7/2004 |

(Continued)

OTHER PUBLICATIONS

U.S. Appl. No. 17/130,700, filed Dec. 22, 2020, Sarah Plewe.

(Continued)

*Primary Examiner* — Vi X Nguyen
(74) *Attorney, Agent, or Firm* — Chang & Hale LLP

(57) ABSTRACT

Techniques for aligning a medical instrument for percutaneous access to a location within the human anatomy can include determining an orientation of the medical instrument, determining a target location within the human anatomy, and determining a plane that includes the target location. Further, the techniques can include determining a projected position of the medical instrument on the plane and generating interface data indicating a distance between the projected position and the target location on the plane.

30 Claims, 39 Drawing Sheets

(56) References Cited

U.S. PATENT DOCUMENTS

| | | |
|---|---|---|
| D307,263 S | 4/1990 | Ishida |
| 5,194,791 A | 3/1993 | Cull |
| 5,199,417 A | 4/1993 | Muller et al. |
| 5,251,611 A | 10/1993 | Zehel et al. |
| 5,273,025 A | 12/1993 | Sakiyama et al. |
| 5,280,781 A | 1/1994 | Oku |
| 5,408,263 A | 4/1995 | Kikuchi et al. |
| 5,526,812 A | 6/1996 | Dumoulin et al. |
| 5,550,953 A | 8/1996 | Seraji |
| 5,669,876 A | 9/1997 | Schechter et al. |
| 5,672,877 A | 9/1997 | Liebig et al. |
| 5,769,086 A | 6/1998 | Ritchart et al. |
| 5,831,614 A | 11/1998 | Tognazzini et al. |
| 5,876,325 A | 3/1999 | Mizuno et al. |
| 5,899,851 A | 5/1999 | Koninckx |
| 5,935,075 A | 8/1999 | Casscells et al. |
| 6,004,016 A | 12/1999 | Spector |
| 6,038,467 A | 3/2000 | Bliek et al. |
| 6,047,080 A | 4/2000 | Chen et al. |
| 6,059,718 A | 5/2000 | Taniguchi et al. |
| 6,063,095 A | 5/2000 | Wang et al. |
| 6,167,292 A | 12/2000 | Badano et al. |
| 6,198,974 B1 | 3/2001 | Webster, Jr. |
| 6,203,493 B1 | 3/2001 | Ben-Haim |
| 6,246,200 B1 | 6/2001 | Blumenkranz et al. |
| 6,246,784 B1 | 6/2001 | Summers et al. |
| 6,246,898 B1 | 6/2001 | Vesely et al. |
| 6,332,089 B1 | 12/2001 | Acker et al. |
| 6,425,865 B1 | 7/2002 | Salcudean et al. |
| 6,459,926 B1 | 10/2002 | Nowlin et al. |
| 6,466,198 B1 | 10/2002 | Feinstein |
| 6,490,467 B1 | 12/2002 | Bucholz et al. |
| 6,553,251 B1 | 4/2003 | Lähdesmäki |
| 6,665,554 B1 | 12/2003 | Charles et al. |
| 6,671,538 B1 | 12/2003 | Ehnholm et al. |
| 6,690,963 B2 | 2/2004 | Ben-Haim et al. |
| 6,690,964 B2 | 2/2004 | Bieger et al. |
| 6,755,797 B1 | 6/2004 | Stouffer |
| 6,812,842 B2 | 11/2004 | Dimmer |
| 6,837,846 B2 | 1/2005 | Jaffe et al. |
| 6,899,672 B2 | 5/2005 | Chin et al. |
| 6,926,709 B2 | 8/2005 | Bieger et al. |
| 7,180,976 B2 | 2/2007 | Wink et al. |
| 7,197,354 B2 | 3/2007 | Sobe |
| 7,206,627 B2 | 4/2007 | Abovitz et al. |
| 7,233,820 B2 | 6/2007 | Gilboa |
| 7,386,339 B2 | 6/2008 | Strommer et al. |
| 7,607,440 B2 | 10/2009 | Coste-Maniere et al. |
| 7,756,563 B2 | 7/2010 | Higgins et al. |
| 7,763,015 B2 | 7/2010 | Cooper et al. |
| 7,772,541 B2 | 8/2010 | Froggatt et al. |
| 7,850,642 B2 | 12/2010 | Moll et al. |
| 7,901,348 B2 | 3/2011 | Soper et al. |
| 7,963,288 B2 | 6/2011 | Rosenberg et al. |
| 8,021,326 B2 | 9/2011 | Moll et al. |
| 8,155,403 B2 | 4/2012 | Tschirren et al. |
| 8,190,238 B2 | 5/2012 | Moll et al. |
| 8,298,135 B2 | 10/2012 | Ito et al. |
| 8,317,746 B2 | 11/2012 | Sewell et al. |
| 8,335,557 B2 | 12/2012 | Maschke |
| 8,348,931 B2 | 1/2013 | Cooper et al. |
| 8,376,934 B2 | 2/2013 | Takahashi et al. |
| 8,394,054 B2 | 3/2013 | Wallace et al. |
| 8,396,595 B2 | 3/2013 | Dariush |
| 8,442,618 B2 | 5/2013 | Strommer et al. |
| 8,460,236 B2 | 6/2013 | Roelle et al. |
| 8,469,945 B2 | 6/2013 | Schena |
| 8,498,691 B2 | 7/2013 | Moll et al. |
| 8,506,555 B2 | 8/2013 | Morales |
| 8,554,368 B2 | 10/2013 | Fielding et al. |
| 8,573,228 B2 | 11/2013 | Kalpin |
| 8,652,030 B2 | 2/2014 | Matsuura et al. |
| 8,720,448 B2 | 5/2014 | Reis et al. |
| 8,738,181 B2 | 5/2014 | Greer et al. |
| 8,821,376 B2 | 9/2014 | Tolkowsky |
| 8,827,948 B2 | 9/2014 | Romo et al. |
| 8,858,424 B2 | 10/2014 | Hasegawa et al. |
| 8,894,610 B2 | 11/2014 | MacNamara et al. |
| 8,929,631 B2 | 1/2015 | Pfister et al. |
| 8,945,095 B2 | 2/2015 | Blumenkranz et al. |
| 9,014,851 B2 | 4/2015 | Wong et al. |
| 9,023,060 B2 | 5/2015 | Cooper et al. |
| 9,084,623 B2 | 7/2015 | Gomez et al. |
| 9,125,639 B2 | 9/2015 | Mathis et al. |
| 9,129,417 B2 | 9/2015 | Zheng et al. |
| 9,138,129 B2 | 9/2015 | Diolaiti |
| 9,173,713 B2 | 11/2015 | Hart et al. |
| 9,183,354 B2 | 11/2015 | Baker et al. |
| 9,186,046 B2 | 11/2015 | Ramamurthy et al. |
| 9,199,372 B2 | 12/2015 | Henderson et al. |
| 9,226,796 B2 | 1/2016 | Bowling et al. |
| 9,256,940 B2 | 2/2016 | Carelsen et al. |
| 9,259,274 B2 | 2/2016 | Prisco |
| 9,272,416 B2 | 3/2016 | Hourtash et al. |
| 9,289,578 B2 | 3/2016 | Walker et al. |
| 9,302,702 B1 | 4/2016 | Schepmann et al. |
| 9,314,306 B2 | 4/2016 | Yu |
| 9,345,456 B2 | 5/2016 | Tsonton et al. |
| 9,358,682 B2 | 6/2016 | Morales |
| 9,452,276 B2 | 9/2016 | Duindam et al. |
| 9,459,087 B2 | 10/2016 | Dunbar et al. |
| 9,504,604 B2 | 11/2016 | Alvarez |
| 9,522,034 B2 | 12/2016 | Johnson et al. |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,595 B2 | 4/2017 | Walker et al. |
| 9,629,682 B2 | 4/2017 | Wallace et al. |
| 9,636,184 B2 | 5/2017 | Lee et al. |
| 9,668,768 B2 | 6/2017 | Piron et al. |
| 9,675,422 B2 | 6/2017 | Hourtash et al. |
| 9,710,921 B2 | 7/2017 | Wong et al. |
| 9,713,509 B2 | 7/2017 | Schuh et al. |
| 9,717,563 B2 | 8/2017 | Tognaccini et al. |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,782,229 B2 | 10/2017 | Crawford et al. |
| 9,788,910 B2 | 10/2017 | Schuh |
| 9,789,608 B2 | 10/2017 | Itkowitz et al. |
| 9,839,481 B2 | 12/2017 | Blumenkranz et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,130,345 B2 | 11/2018 | Wong et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |

(56) References Cited

U.S. PATENT DOCUMENTS

| | | | |
|---|---|---|---|
| 10,278,778 B2 | 5/2019 | State et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,383,765 B2 | 8/2019 | Alvarez et al. |
| 10,398,518 B2 | 9/2019 | Yu et al. |
| 10,405,939 B2 | 9/2019 | Romo |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer et al. |
| 10,454,347 B2 | 10/2019 | Covington et al. |
| 10,464,209 B2 | 11/2019 | Ho et al. |
| 10,470,830 B2 | 11/2019 | Hill et al. |
| 10,482,599 B2 | 11/2019 | Mintz et al. |
| 10,492,741 B2 | 12/2019 | Walker et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan et al. |
| 10,531,864 B2 | 1/2020 | Wong et al. |
| 10,539,478 B2 | 1/2020 | Lin et al. |
| 10,543,048 B2 | 1/2020 | Noonan |
| 10,555,778 B2 | 2/2020 | Ummalaneni |
| 10,583,271 B2 | 3/2020 | Bogusky |
| 10,631,949 B2 | 4/2020 | Schuh et al. |
| 10,639,109 B2 | 5/2020 | Bovay et al. |
| 10,646,291 B2 | 5/2020 | Turner |
| 11,135,023 B2 | 10/2021 | Larkin et al. |
| 11,172,895 B2 | 11/2021 | Dickhans et al. |
| 2001/0000040 A1 | 3/2001 | Adams et al. |
| 2001/0021843 A1 | 9/2001 | Bosselmann et al. |
| 2001/0039421 A1 | 11/2001 | Heilbrun et al. |
| 2002/0035330 A1 | 3/2002 | Cline et al. |
| 2002/0065455 A1 | 5/2002 | Ben-Haim et al. |
| 2002/0077533 A1 | 6/2002 | Bieger et al. |
| 2002/0082612 A1 | 6/2002 | Moll et al. |
| 2002/0120188 A1 | 8/2002 | Brock et al. |
| 2002/0128535 A1 | 9/2002 | Kikuchi et al. |
| 2002/0161280 A1 | 10/2002 | Chatenever et al. |
| 2002/0173878 A1 | 11/2002 | Watanabe et al. |
| 2003/0045778 A1 | 3/2003 | Ohline et al. |
| 2003/0105603 A1 | 6/2003 | Hardesty |
| 2003/0125622 A1 | 7/2003 | Schweikard et al. |
| 2003/0181809 A1 | 9/2003 | Hall et al. |
| 2003/0182091 A1 | 9/2003 | Kukuk |
| 2003/0195664 A1 | 10/2003 | Nowlin et al. |
| 2004/0015079 A1* | 1/2004 | Berger .......... A61B 18/02 600/437 |
| 2004/0047044 A1 | 3/2004 | Dalton |
| 2004/0072066 A1 | 4/2004 | Cho et al. |
| 2004/0152970 A1 | 8/2004 | Hunter et al. |
| 2004/0176751 A1 | 9/2004 | Weitzner et al. |
| 2004/0186349 A1 | 9/2004 | Ewers et al. |
| 2004/0249267 A1 | 12/2004 | Gilboa |
| 2004/0257021 A1 | 12/2004 | Chang et al. |
| 2004/0263535 A1 | 12/2004 | Birkenbach et al. |
| 2005/0027397 A1 | 2/2005 | Niemeyer |
| 2005/0043718 A1 | 2/2005 | Madhani et al. |
| 2005/0060006 A1 | 3/2005 | Pflueger et al. |
| 2005/0065400 A1 | 3/2005 | Banik et al. |
| 2005/0085714 A1 | 4/2005 | Foley et al. |
| 2005/0107679 A1 | 5/2005 | Geiger et al. |
| 2005/0107917 A1 | 5/2005 | Smith et al. |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0193451 A1 | 9/2005 | Quistgaard et al. |
| 2005/0222554 A1 | 10/2005 | Wallace et al. |
| 2005/0234293 A1 | 10/2005 | Yamamoto et al. |
| 2005/0256398 A1 | 11/2005 | Hastings et al. |
| 2005/0261551 A1 | 11/2005 | Couvillon |
| 2005/0272975 A1 | 12/2005 | McWeeney et al. |
| 2006/0004286 A1 | 1/2006 | Chang et al. |
| 2006/0015096 A1 | 1/2006 | Hauck et al. |
| 2006/0025668 A1 | 2/2006 | Peterson et al. |
| 2006/0041293 A1 | 2/2006 | Mehdizadeh et al. |
| 2006/0058617 A1 | 3/2006 | Sano et al. |
| 2006/0058643 A1 | 3/2006 | Florent et al. |
| 2006/0079745 A1 | 4/2006 | Viswanathan |
| 2006/0084860 A1 | 4/2006 | Geiger et al. |
| 2006/0095066 A1 | 5/2006 | Chang et al. |
| 2006/0098851 A1 | 5/2006 | Shoham et al. |
| 2006/0149134 A1 | 7/2006 | Soper et al. |
| 2006/0173290 A1 | 8/2006 | Lavallee et al. |
| 2006/0178556 A1 | 8/2006 | Hasser et al. |
| 2006/0184016 A1 | 8/2006 | Glossop |
| 2006/0200026 A1 | 9/2006 | Wallace et al. |
| 2006/0200049 A1 | 9/2006 | Leo et al. |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0013336 A1 | 1/2007 | Nowlin et al. |
| 2007/0032826 A1 | 2/2007 | Schwartz |
| 2007/0043455 A1 | 2/2007 | Viswanathan et al. |
| 2007/0055128 A1 | 3/2007 | Glossop |
| 2007/0055144 A1 | 3/2007 | Neustadter et al. |
| 2007/0073136 A1 | 3/2007 | Metzger |
| 2007/0083193 A1 | 4/2007 | Werneth et al. |
| 2007/0123748 A1 | 5/2007 | Meglan |
| 2007/0135886 A1 | 6/2007 | Maschke |
| 2007/0142971 A1 | 6/2007 | Schena |
| 2007/0150155 A1 | 6/2007 | Kawai et al. |
| 2007/0156019 A1 | 7/2007 | Larkin et al. |
| 2007/0161857 A1 | 7/2007 | Durant et al. |
| 2007/0167743 A1 | 7/2007 | Honda et al. |
| 2007/0167801 A1 | 7/2007 | Webler et al. |
| 2007/0208252 A1 | 9/2007 | Makower |
| 2007/0232856 A1 | 10/2007 | Ueno et al. |
| 2007/0249911 A1 | 10/2007 | Simon |
| 2007/0253599 A1 | 11/2007 | White et al. |
| 2007/0269001 A1 | 11/2007 | Maschke |
| 2007/0287992 A1 | 12/2007 | Diolaiti et al. |
| 2007/0293721 A1 | 12/2007 | Gilboa |
| 2007/0299353 A1 | 12/2007 | Harlev et al. |
| 2008/0027313 A1 | 1/2008 | Shachar |
| 2008/0046122 A1 | 2/2008 | Manzo et al. |
| 2008/0071140 A1 | 3/2008 | Gattani et al. |
| 2008/0079421 A1 | 4/2008 | Jensen |
| 2008/0103389 A1 | 5/2008 | Begelman et al. |
| 2008/0108870 A1 | 5/2008 | Wiita et al. |
| 2008/0118118 A1 | 5/2008 | Berger |
| 2008/0118135 A1 | 5/2008 | Averbuch et al. |
| 2008/0123921 A1 | 5/2008 | Gielen et al. |
| 2008/0140087 A1 | 6/2008 | Barbagli |
| 2008/0147089 A1 | 6/2008 | Loh et al. |
| 2008/0159653 A1 | 7/2008 | Dunki-Jacobs et al. |
| 2008/0161681 A1 | 7/2008 | Hauck |
| 2008/0183064 A1 | 7/2008 | Chandonnet et al. |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0231221 A1 | 9/2008 | Ogawa |
| 2008/0243142 A1 | 10/2008 | Gildenberg |
| 2008/0249640 A1 | 10/2008 | Vittor et al. |
| 2008/0255505 A1 | 10/2008 | Carlson et al. |
| 2008/0262297 A1 | 10/2008 | Gilboa et al. |
| 2008/0275349 A1 | 11/2008 | Halperin et al. |
| 2008/0287963 A1 | 11/2008 | Rogers et al. |
| 2008/0306490 A1 | 12/2008 | Lakin et al. |
| 2008/0312501 A1 | 12/2008 | Hasegawa et al. |
| 2008/0312771 A1 | 12/2008 | Sugiura |
| 2009/0005768 A1 | 1/2009 | Sharareh et al. |
| 2009/0030307 A1 | 1/2009 | Govari et al. |
| 2009/0048611 A1 | 2/2009 | Funda et al. |
| 2009/0054729 A1 | 2/2009 | Mori et al. |
| 2009/0062611 A1 | 3/2009 | Toyama |
| 2009/0062813 A1 | 3/2009 | Prisco et al. |
| 2009/0076476 A1 | 3/2009 | Barbagli et al. |
| 2009/0076534 A1 | 3/2009 | Shelton, IV et al. |

(56) References Cited

U.S. PATENT DOCUMENTS

| | | |
|---|---|---|
| 2009/0149867 A1 | 6/2009 | Glozman et al. |
| 2009/0184825 A1 | 7/2009 | Anderson |
| 2009/0198298 A1 | 8/2009 | Kaiser et al. |
| 2009/0227861 A1 | 9/2009 | Ganatra et al. |
| 2009/0228020 A1 | 9/2009 | Wallace et al. |
| 2009/0245600 A1 | 10/2009 | Hoffman et al. |
| 2009/0248036 A1 | 10/2009 | Hoffman et al. |
| 2009/0256905 A1 | 10/2009 | Tashiro |
| 2009/0259099 A1 | 10/2009 | Zhou et al. |
| 2009/0259230 A1 | 10/2009 | Khadem et al. |
| 2009/0262109 A1 | 10/2009 | Markowitz et al. |
| 2009/0287354 A1 | 11/2009 | Choi |
| 2009/0292166 A1 | 11/2009 | Ito et al. |
| 2009/0295797 A1 | 12/2009 | Sakaguchi |
| 2009/0324161 A1 | 12/2009 | Prisco |
| 2009/0326318 A1 | 12/2009 | Tognaccini et al. |
| 2010/0008555 A1 | 1/2010 | Trumer et al. |
| 2010/0030061 A1 | 2/2010 | Canfield et al. |
| 2010/0030115 A1 | 2/2010 | Fujimoto et al. |
| 2010/0039506 A1 | 2/2010 | Sarvestani et al. |
| 2010/0041949 A1 | 2/2010 | Tolkowsky |
| 2010/0054536 A1 | 3/2010 | Huang et al. |
| 2010/0069920 A1 | 3/2010 | Naylor et al. |
| 2010/0076263 A1 | 3/2010 | Tanaka et al. |
| 2010/0082041 A1 | 4/2010 | Prisco |
| 2010/0121138 A1 | 5/2010 | Goldenberg et al. |
| 2010/0121139 A1 | 5/2010 | OuYang et al. |
| 2010/0137882 A1 | 6/2010 | Quaid, III |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0168918 A1 | 7/2010 | Zhao et al. |
| 2010/0198170 A1 | 8/2010 | Umeda et al. |
| 2010/0204713 A1 | 8/2010 | Morales |
| 2010/0225209 A1 | 9/2010 | Goldberg et al. |
| 2010/0228266 A1 | 9/2010 | Hourtash |
| 2010/0234856 A1 | 9/2010 | Stoianovici et al. |
| 2010/0234857 A1 | 9/2010 | Itkowitz et al. |
| 2010/0240989 A1 | 9/2010 | Stoianovici et al. |
| 2010/0256812 A1 | 10/2010 | Tsusaka et al. |
| 2010/0290530 A1 | 11/2010 | Huang et al. |
| 2010/0292565 A1 | 11/2010 | Meyer et al. |
| 2010/0298641 A1 | 11/2010 | Tanaka |
| 2010/0328455 A1 | 12/2010 | Nam et al. |
| 2011/0009880 A1 | 1/2011 | Prisco et al. |
| 2011/0015484 A1 | 1/2011 | Alvarez et al. |
| 2011/0021926 A1 | 1/2011 | Spencer et al. |
| 2011/0054303 A1 | 3/2011 | Barrick et al. |
| 2011/0082366 A1 | 4/2011 | Scully et al. |
| 2011/0082462 A1 | 4/2011 | Suarez et al. |
| 2011/0092808 A1 | 4/2011 | Shachar et al. |
| 2011/0137122 A1 | 6/2011 | Kawai |
| 2011/0153252 A1 | 6/2011 | Govari et al. |
| 2011/0160570 A1 | 6/2011 | Kariv et al. |
| 2011/0184238 A1 | 7/2011 | Higgins et al. |
| 2011/0196199 A1 | 8/2011 | Donhowe et al. |
| 2011/0218676 A1 | 9/2011 | Okazaki |
| 2011/0234780 A1 | 9/2011 | Ito et al. |
| 2011/0238082 A1 | 9/2011 | Wenderow et al. |
| 2011/0245665 A1 | 10/2011 | Nentwick |
| 2011/0248987 A1 | 10/2011 | Mitchell |
| 2011/0249016 A1 | 10/2011 | Zhang et al. |
| 2011/0257480 A1 | 10/2011 | Takahashi et al. |
| 2011/0258842 A1 | 10/2011 | Dukesherer et al. |
| 2011/0276179 A1 | 11/2011 | Banks et al. |
| 2011/0277775 A1 | 11/2011 | Holop et al. |
| 2011/0282188 A1* | 11/2011 | Burnside ............... A61B 5/062 600/424 |
| 2011/0319910 A1 | 12/2011 | Roelle et al. |
| 2012/0000427 A1 | 1/2012 | Nilsson |
| 2012/0046521 A1 | 2/2012 | Hunter et al. |
| 2012/0046522 A1 | 2/2012 | Naito |
| 2012/0056986 A1 | 3/2012 | Popovic |
| 2012/0059249 A1 | 3/2012 | Verard et al. |
| 2012/0062714 A1 | 3/2012 | Liu et al. |
| 2012/0065481 A1 | 3/2012 | Hunter et al. |
| 2012/0069167 A1 | 3/2012 | Liu et al. |
| 2012/0071752 A1 | 3/2012 | Sewell et al. |
| 2012/0071782 A1 | 3/2012 | Patil et al. |
| 2012/0071822 A1 | 3/2012 | Romo et al. |
| 2012/0071894 A1 | 3/2012 | Tanner et al. |
| 2012/0082351 A1 | 4/2012 | Higgins et al. |
| 2012/0120305 A1 | 5/2012 | Takahashi |
| 2012/0123441 A1 | 5/2012 | Au et al. |
| 2012/0130217 A1 | 5/2012 | Kauphusman et al. |
| 2012/0143268 A1 | 6/2012 | Burroughs |
| 2012/0165656 A1 | 6/2012 | Montag et al. |
| 2012/0191079 A1 | 7/2012 | Moll et al. |
| 2012/0209069 A1 | 8/2012 | Popovic et al. |
| 2012/0209293 A1 | 8/2012 | Carlson et al. |
| 2012/0215094 A1 | 8/2012 | Rahimian et al. |
| 2012/0219185 A1 | 8/2012 | Hu et al. |
| 2012/0221007 A1 | 8/2012 | Batten et al. |
| 2012/0239060 A1 | 9/2012 | Orban, III |
| 2012/0253200 A1 | 10/2012 | Stolka et al. |
| 2012/0253276 A1 | 10/2012 | Govari et al. |
| 2012/0283745 A1 | 11/2012 | Goldberg et al. |
| 2012/0283747 A1 | 11/2012 | Popovic |
| 2012/0289777 A1 | 11/2012 | Chopra et al. |
| 2012/0289783 A1 | 11/2012 | Duindam et al. |
| 2012/0302869 A1 | 11/2012 | Koyrakh et al. |
| 2012/0328077 A1 | 12/2012 | Bouvier |
| 2013/0018306 A1 | 1/2013 | Ludwin |
| 2013/0060146 A1 | 3/2013 | Yang et al. |
| 2013/0085330 A1 | 4/2013 | Ramamurthy et al. |
| 2013/0090530 A1 | 4/2013 | Ramamurthy et al. |
| 2013/0102846 A1 | 4/2013 | Sjostrom et al. |
| 2013/0123580 A1 | 5/2013 | Peters et al. |
| 2013/0131503 A1 | 5/2013 | Schneider et al. |
| 2013/0144116 A1 | 6/2013 | Cooper et al. |
| 2013/0165854 A1 | 6/2013 | Sandhu et al. |
| 2013/0165945 A9 | 6/2013 | Roelle et al. |
| 2013/0197357 A1 | 8/2013 | Green et al. |
| 2013/0204124 A1 | 8/2013 | Duindam et al. |
| 2013/0209208 A1 | 8/2013 | Bailey et al. |
| 2013/0218005 A1 | 8/2013 | Desai et al. |
| 2013/0225942 A1 | 8/2013 | Holsing et al. |
| 2013/0243153 A1 | 9/2013 | Sra et al. |
| 2013/0246334 A1 | 9/2013 | Ahuja et al. |
| 2013/0259315 A1 | 10/2013 | Angot et al. |
| 2013/0274783 A1 | 10/2013 | Wynberg |
| 2013/0303891 A1 | 11/2013 | Chopra |
| 2013/0303892 A1 | 11/2013 | Zhao et al. |
| 2013/0325030 A1 | 12/2013 | Hourtash et al. |
| 2013/0345718 A1 | 12/2013 | Crawford et al. |
| 2014/0001235 A1 | 1/2014 | Shelton, IV |
| 2014/0051049 A1 | 2/2014 | Jarc et al. |
| 2014/0058406 A1 | 2/2014 | Tsekos |
| 2014/0107390 A1 | 4/2014 | Brown et al. |
| 2014/0114180 A1 | 4/2014 | Jain |
| 2014/0135985 A1 | 5/2014 | Coste-Maniere et al. |
| 2014/0142591 A1 | 5/2014 | Alvarez et al. |
| 2014/0148808 A1 | 5/2014 | Inkpen et al. |
| 2014/0163664 A1 | 6/2014 | Goldsmith |
| 2014/0180063 A1 | 6/2014 | Zhao et al. |
| 2014/0222207 A1 | 8/2014 | Bowling et al. |
| 2014/0235943 A1 | 8/2014 | Paris et al. |
| 2014/0243801 A1 | 8/2014 | Fanelli et al. |
| 2014/0243849 A1 | 8/2014 | Saglam et al. |
| 2014/0257333 A1 | 9/2014 | Blumenkranz |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan et al. |
| 2014/0276937 A1 | 9/2014 | Wong et al. |
| 2014/0277333 A1 | 9/2014 | Lewis et al. |
| 2014/0296655 A1 | 10/2014 | Akhbardeh et al. |
| 2014/0296657 A1 | 10/2014 | Izmirli et al. |
| 2014/0296870 A1 | 10/2014 | Stern et al. |
| 2014/0309527 A1 | 10/2014 | Namati et al. |
| 2014/0309625 A1 | 10/2014 | Okamoto et al. |
| 2014/0316420 A1 | 10/2014 | Ballard et al. |
| 2014/0343416 A1 | 11/2014 | Panescu et al. |
| 2014/0343569 A1 | 11/2014 | Turner |

(56) References Cited

U.S. PATENT DOCUMENTS

| | | |
|---|---|---|
| 2014/0350391 A1 | 11/2014 | Prisco et al. |
| 2014/0357984 A1 | 12/2014 | Wallace et al. |
| 2014/0364739 A1 | 12/2014 | Liu et al. |
| 2014/0364870 A1 | 12/2014 | Alvarez et al. |
| 2015/0025549 A1 | 1/2015 | Kilroy et al. |
| 2015/0045675 A1 | 2/2015 | Chernomorsky |
| 2015/0051482 A1 | 2/2015 | Liu et al. |
| 2015/0054929 A1 | 2/2015 | Ito et al. |
| 2015/0057498 A1 | 2/2015 | Akimoto et al. |
| 2015/0073266 A1 | 3/2015 | Brannan et al. |
| 2015/0073267 A1 | 3/2015 | Brannan et al. |
| 2015/0088161 A1 | 3/2015 | Hata et al. |
| 2015/0104284 A1 | 4/2015 | Riedel |
| 2015/0119628 A1 | 4/2015 | Bharat et al. |
| 2015/0119645 A1 | 4/2015 | Baldwin |
| 2015/0141808 A1 | 5/2015 | Elhawary et al. |
| 2015/0141858 A1 | 5/2015 | Razavi et al. |
| 2015/0142013 A1 | 5/2015 | Tanner et al. |
| 2015/0150635 A1 | 6/2015 | Kilroy et al. |
| 2015/0150636 A1 | 6/2015 | Hagn et al. |
| 2015/0202015 A1 | 7/2015 | Elhawary et al. |
| 2015/0209056 A1 | 7/2015 | Shoham et al. |
| 2015/0223725 A1 | 8/2015 | Engel et al. |
| 2015/0223832 A1 | 8/2015 | Swaney |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Messick, Jr. |
| 2015/0265359 A1 | 9/2015 | Camarillo |
| 2015/0265368 A1 | 9/2015 | Chopra et al. |
| 2015/0265807 A1 | 9/2015 | Park et al. |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0297299 A1 | 10/2015 | Yeung et al. |
| 2015/0305650 A1 | 10/2015 | Hunter et al. |
| 2015/0311838 A1 | 10/2015 | Moule et al. |
| 2015/0313503 A1 | 11/2015 | Seibel et al. |
| 2015/0342695 A1 | 12/2015 | He et al. |
| 2015/0359597 A1 | 12/2015 | Gombert et al. |
| 2016/0000302 A1 | 1/2016 | Brown et al. |
| 2016/0000414 A1 | 1/2016 | Brown et al. |
| 2016/0000495 A1 | 1/2016 | Elliott et al. |
| 2016/0000520 A1 | 1/2016 | Lachmanovich et al. |
| 2016/0001038 A1 | 1/2016 | Romo et al. |
| 2016/0005168 A1 | 1/2016 | Merlet |
| 2016/0005220 A1 | 1/2016 | Weingarten et al. |
| 2016/0005576 A1 | 1/2016 | Tsukamoto |
| 2016/0008033 A1 | 1/2016 | Hawkins et al. |
| 2016/0016319 A1 | 1/2016 | Remirez et al. |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper et al. |
| 2016/0075030 A1 | 3/2016 | Takahashi |
| 2016/0081568 A1 | 3/2016 | Kolberg et al. |
| 2016/0100772 A1 | 4/2016 | Ikuma et al. |
| 2016/0111192 A1 | 4/2016 | Suzara |
| 2016/0128992 A1 | 5/2016 | Hudson et al. |
| 2016/0166320 A1 | 6/2016 | Ciulla et al. |
| 2016/0183841 A1 | 6/2016 | Duindam et al. |
| 2016/0199134 A1 | 7/2016 | Brown et al. |
| 2016/0206389 A1 | 7/2016 | Miller |
| 2016/0213432 A1 | 7/2016 | Flexman et al. |
| 2016/0228032 A1 | 8/2016 | Walker et al. |
| 2016/0270865 A1 | 9/2016 | Landey et al. |
| 2016/0278865 A1 | 9/2016 | Capote et al. |
| 2016/0287053 A1 | 10/2016 | Miura |
| 2016/0287111 A1 | 10/2016 | Jacobsen |
| 2016/0287279 A1 | 10/2016 | Bovay et al. |
| 2016/0287346 A1 | 10/2016 | Hyodo et al. |
| 2016/0314710 A1 | 10/2016 | Jarc et al. |
| 2016/0331469 A1 | 11/2016 | Hall et al. |
| 2016/0338787 A1 | 11/2016 | Popovic et al. |
| 2016/0346038 A1 | 12/2016 | Helgeson et al. |
| 2016/0346924 A1 | 12/2016 | Hasegawa et al. |
| 2016/0354057 A1 | 12/2016 | Hansen et al. |
| 2016/0354152 A1 | 12/2016 | Beck |
| 2016/0360947 A1 | 12/2016 | Iida et al. |
| 2016/0360949 A1 | 12/2016 | Hyodo et al. |
| 2016/0372743 A1 | 12/2016 | Cho et al. |
| 2017/0007337 A1 | 1/2017 | Dan |
| 2017/0023423 A1 | 1/2017 | Jackson et al. |
| 2017/0055851 A1 | 3/2017 | Al-Ali |
| 2017/0056215 A1 | 3/2017 | Nagesh et al. |
| 2017/0068796 A1 | 3/2017 | Passerini et al. |
| 2017/0071456 A1 | 3/2017 | Ratnakar |
| 2017/0079725 A1 | 3/2017 | Hoffman et al. |
| 2017/0079726 A1 | 3/2017 | Hoffman et al. |
| 2017/0095299 A1 | 4/2017 | Hendrick et al. |
| 2017/0100197 A1 | 4/2017 | Zubiate et al. |
| 2017/0106904 A1 | 4/2017 | Hanson et al. |
| 2017/0119412 A1 | 5/2017 | Noonan et al. |
| 2017/0119481 A1 | 5/2017 | Romo et al. |
| 2017/0135710 A1 | 5/2017 | Hasegawa et al. |
| 2017/0135718 A1 | 5/2017 | Lyons |
| 2017/0135833 A1 | 5/2017 | Syed |
| 2017/0143442 A1 | 5/2017 | Tesar et al. |
| 2017/0165503 A1 | 6/2017 | Hautvast et al. |
| 2017/0181809 A1 | 6/2017 | Panescu et al. |
| 2017/0189118 A1 | 7/2017 | Chopra et al. |
| 2017/0189131 A1 | 7/2017 | Weir |
| 2017/0202627 A1 | 7/2017 | Sramek et al. |
| 2017/0209073 A1 | 7/2017 | Sramek et al. |
| 2017/0209162 A1 | 7/2017 | Sperry et al. |
| 2017/0215808 A1 | 8/2017 | Shimol et al. |
| 2017/0215969 A1 | 8/2017 | Zhai et al. |
| 2017/0231647 A1 | 8/2017 | Saunders et al. |
| 2017/0238807 A9 | 8/2017 | Vertikov |
| 2017/0245854 A1 | 8/2017 | Zemlok et al. |
| 2017/0245885 A1 | 8/2017 | Lenker |
| 2017/0251988 A1 | 9/2017 | Weber et al. |
| 2017/0258366 A1 | 9/2017 | Tupin, Jr. et al. |
| 2017/0280978 A1 | 10/2017 | Yamamoto et al. |
| 2017/0281049 A1 | 10/2017 | Yamamoto et al. |
| 2017/0290631 A1 | 10/2017 | Lee et al. |
| 2017/0296032 A1 | 10/2017 | Li |
| 2017/0296202 A1 | 10/2017 | Brown |
| 2017/0303889 A1 | 10/2017 | Grim et al. |
| 2017/0303941 A1 | 10/2017 | Eisner |
| 2017/0304015 A1 | 10/2017 | Tavallaei et al. |
| 2017/0325715 A1 | 11/2017 | Mehendale et al. |
| 2017/0325896 A1 | 11/2017 | Donhowe et al. |
| 2017/0326337 A1 | 11/2017 | Romoscanu et al. |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360508 A1 | 12/2017 | Germain et al. |
| 2018/0025666 A1 | 1/2018 | Ho et al. |
| 2018/0055576 A1 | 3/2018 | Koyrakh et al. |
| 2018/0055582 A1 | 3/2018 | Krimsky |
| 2018/0064498 A1 | 3/2018 | Kapadia et al. |
| 2018/0098690 A1 | 4/2018 | Iwaki |
| 2018/0098817 A1 | 4/2018 | Nichogi |
| 2018/0169671 A1 | 6/2018 | Winter et al. |
| 2018/0193102 A1 | 7/2018 | Inoue |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289394 A1 | 10/2018 | Shah |
| 2018/0289431 A1 | 10/2018 | Draper et al. |
| 2018/0308247 A1 | 10/2018 | Gupta |
| 2018/0325499 A1 | 11/2018 | Landey et al. |
| 2018/0333044 A1 | 11/2018 | Jenkins |
| 2018/0338799 A1 | 11/2018 | Hladio et al. |
| 2018/0360435 A1 | 12/2018 | Romo |
| 2018/0368920 A1 | 12/2018 | Ummalaneni |
| 2019/0000559 A1 | 1/2019 | Berman et al. |

(56) References Cited

U.S. PATENT DOCUMENTS

| | | |
|---|---|---|
| 2019/0000560 A1 | 1/2019 | Berman et al. |
| 2019/0000576 A1 | 1/2019 | Mintz et al. |
| 2019/0046814 A1 | 2/2019 | Senden et al. |
| 2019/0066314 A1 | 2/2019 | Abhari et al. |
| 2019/0083178 A1 | 3/2019 | Mata et al. |
| 2019/0083183 A1 | 3/2019 | Moll et al. |
| 2019/0086349 A1 | 3/2019 | Nelson et al. |
| 2019/0110839 A1 | 4/2019 | Rafii-Tari et al. |
| 2019/0125164 A1 | 5/2019 | Roelle et al. |
| 2019/0151148 A1 | 5/2019 | Alvarez et al. |
| 2019/0167366 A1 | 6/2019 | Ummalaneni et al. |
| 2019/0167367 A1 | 6/2019 | Walker et al. |
| 2019/0175009 A1 | 6/2019 | Mintz et al. |
| 2019/0175062 A1 | 6/2019 | Rafii-Tari et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0201105 A1 | 7/2019 | Shelton, IV et al. |
| 2019/0209252 A1 | 7/2019 | Walker et al. |
| 2019/0216548 A1 | 7/2019 | Ummalaneni |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata et al. |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000530 A1 | 1/2020 | DeFonzo et al. |
| 2020/0000533 A1 | 1/2020 | Schuh et al. |
| 2020/0008874 A1 | 1/2020 | Barbagli et al. |
| 2020/0022767 A1 | 1/2020 | Hill et al. |
| 2020/0038123 A1 | 2/2020 | Graetzel et al. |
| 2020/0039086 A1 | 2/2020 | Meyer et al. |
| 2020/0046434 A1 | 2/2020 | Graetzel et al. |
| 2020/0054405 A1 | 2/2020 | Schuh et al. |
| 2020/0054408 A1 | 2/2020 | Schuh et al. |
| 2020/0060516 A1 | 2/2020 | Baez, Jr. |
| 2020/0078103 A1 | 3/2020 | Duindam et al. |
| 2020/0085516 A1 | 3/2020 | DeFonzo et al. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |
| 2020/0155084 A1 | 5/2020 | Walker et al. |
| 2020/0170630 A1 | 6/2020 | Wong et al. |
| 2020/0170720 A1 | 6/2020 | Ummalaneni |
| 2020/0171660 A1 | 6/2020 | Ho et al. |
| 2020/0188043 A1 | 6/2020 | Yu et al. |
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |
| 2020/0246591 A1 | 8/2020 | Bogusky |
| 2020/0261172 A1 | 8/2020 | Romo et al. |
| 2020/0268459 A1 | 8/2020 | Noonan |
| 2020/0268460 A1 | 8/2020 | Tse et al. |
| 2020/0281787 A1 | 9/2020 | Ruiz |
| 2020/0297437 A1 | 9/2020 | Schuh et al. |
| 2020/0305922 A1 | 10/2020 | Yan et al. |
| 2020/0305983 A1 | 10/2020 | Yampolsky et al. |
| 2020/0305989 A1 | 10/2020 | Schuh et al. |
| 2020/0315717 A1 | 10/2020 | Bovay et al. |
| 2020/0315723 A1 | 10/2020 | Hassan et al. |
| 2020/0323596 A1 | 10/2020 | Moll et al. |
| 2020/0330167 A1 | 10/2020 | Romo et al. |
| 2021/0196312 A1 | 7/2021 | Plewe et al. |
| 2021/0196399 A1 | 7/2021 | Ayvali et al. |

FOREIGN PATENT DOCUMENTS

| | | |
|---|---|---|
| CN | 1846181 A | 10/2006 |
| CN | 1857877 A | 11/2006 |
| CN | 101147676 A | 3/2008 |
| CN | 102316817 A | 1/2012 |
| CN | 101325920 B | 2/2012 |
| CN | 102341057 A | 2/2012 |
| CN | 101222882 B | 3/2013 |
| CN | 102973317 A | 3/2013 |
| CN | 103705307 A | 4/2014 |
| CN | 103735313 A | 4/2014 |
| CN | 102458295 B | 6/2014 |
| CN | 103930063 A | 7/2014 |
| CN | 102711586 B | 6/2015 |
| CN | 103565529 B | 6/2015 |
| CN | 103767659 B | 6/2015 |
| CN | 105030331 A | 11/2015 |
| CN | 105511881 A | 4/2016 |
| CN | 105559886 A | 5/2016 |
| CN | 104758066 B | 5/2017 |
| CN | 105559850 B | 8/2017 |
| CN | 107028659 A | 8/2017 |
| CN | 103813748 B | 4/2018 |
| CN | 108348139 A | 7/2018 |
| CN | 104931059 B | 9/2018 |
| CN | 104684502 B | 10/2018 |
| CN | 106821498 B | 2/2020 |
| DE | 102013100605 A1 | 7/2014 |
| EP | 3347098 B1 | 2/1996 |
| EP | 1250986 A2 | 10/2002 |
| EP | 1800593 A4 | 1/2009 |
| EP | 2158834 A1 | 3/2010 |
| EP | 1566150 B1 | 4/2010 |
| EP | 2615992 A2 | 7/2013 |
| EP | 3025630 A4 | 3/2017 |
| EP | 2392435 B1 | 12/2020 |
| JP | 2008528130 A | 7/2008 |
| JP | 2009509654 A | 3/2009 |
| JP | 2009524530 A | 7/2009 |
| JP | 2011088260 A | 5/2011 |
| JP | 2013510662 A | 3/2013 |
| JP | 6388686 B2 | 9/2018 |
| KR | 1020140009359 A | 1/2014 |
| RU | 2569699 C2 | 11/2015 |
| WO | 3156457 A1 | 8/2001 |
| WO | 2004029782 A2 | 4/2004 |
| WO | 2005078128 A1 | 8/2005 |
| WO | 2006122061 A1 | 11/2006 |
| WO | 2006124388 A1 | 11/2006 |
| WO | 2009097461 A1 | 8/2009 |
| WO | 2009120940 A2 | 10/2009 |
| WO | 2010127162 A1 | 11/2010 |
| WO | 2011002215 A3 | 4/2011 |
| WO | 2011058893 A1 | 5/2011 |
| WO | 2011100110 A1 | 8/2011 |
| WO | 2011132409 A1 | 10/2011 |
| WO | 2012044334 A2 | 4/2012 |
| WO | 2012082719 A1 | 6/2012 |
| WO | 2012109760 A1 | 8/2012 |
| WO | 2013039564 A2 | 3/2013 |
| WO | 2013055707 A1 | 4/2013 |
| WO | 2014052428 A1 | 4/2014 |
| WO | 2014114551 A1 | 7/2014 |
| WO | 2015089013 A1 | 6/2015 |

(56) References Cited

FOREIGN PATENT DOCUMENTS

| WO | 2015142957 A1 | 9/2015 |
| WO | 2017036774 A1 | 3/2017 |
| WO | 2017053698 A1 | 3/2017 |
| WO | 2017066108 A1 | 4/2017 |
| WO | 2017075574 A1 | 5/2017 |
| WO | 2017048194 A9 | 7/2017 |
| WO | 2017118750 A1 | 7/2017 |
| WO | 2017146890 A1 | 8/2017 |
| WO | 2017167754 A1 | 10/2017 |
| WO | 2018098477 A1 | 5/2018 |

OTHER PUBLICATIONS

U.S. Appl. No. 17/131,117, filed Dec. 22, 2020, Sarah Plewe.

Ai-Ahmad et al., dated 2005, Early experience with a computerized robotically controlled cathetersystem, Journal of Interventional Cardiac Electrophysiology, 12:199-202, 4 pages.

Blankenstein, Jun. 2008, Dynamic Registration and High Speed Visual Servoing in Robot-Assisted Surgery, Katholieke Universiteit Leuven, Leuven, Belgium, 96 pages.

Ciuti et al., 2012, Intra-operative monocular 3D reconstruction for image-guided navigation in active locomotion capsule endoscopy. Biomedical Robotics and Biomechatronics (Biorob), 4th IEEE Ras & Embs International Conference On IEEE, 7 pages.

Darwiche, 2015, Operative technique and early experience for robotic assisted laparoscopic nephroureterectomy (RALNU) using da Vinci XI, SpringerPlus, 4:298, 5 pages.

Fallavollita et al., 2010, Acquiring multiview C-arm images to assist cardiac ablation procedures, EURASIP Journal on Image and Video Processing, vol. 2010, Article ID 871408, pp. 1-10.

Gutierrez et al., Mar. 2008, A practical global distortion correction method for an image intensifierbased x-ray fluoroscopy system, Med. Phys, 35(3):997-1007, 11 pgs.

Haigron et al., 2004, Depth-map-based scene analysis for active navigation in virtual angioscopy, IEEE Transactions on Medical Imaging, 23( 11 ): 1380-1390, 11 pages.

Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).

Hansen Medical, Inc. Bibliography, product brochure, 1 p., dated as available at http://hansenmedical.com/bibliography.aspx on Jul. 14, 2006 (accessed Jun. 25, 2019 using the internet archive wav back machine).

Hansen Medical, Inc. dated 2007, Introducing the Sensei Robotic Catheter System, product brochure, 10 pp.

Hansen Medical, Inc. dated 2009, Sensei X Robotic Catheter System, product brochure, 5 pgs.

Hansen Medical, Inc. Technology Advantages, product brochure, dated as available at http://hansenmedical.com/advantages.aspx on Jul. 13, 2006 (accessed Jun. 25, 2019 using the internet archive way back machine), 1 page.

International search report and written opinion dated Dec. 18, 2019 for PCT/US2019/53600 32836259, 13 pages.

Kiraly et al, 2002, Three-dimensional Human Airway Segmentation Methods for Clinical Virtual Bronchoscopy, Acad Radio!, 9:1153-1168,16 pages.

Kiraly et al., Sep. 2004, Three-dimensional path planning for virtual bronchoscopy, IEEE Transactions on Medical Imaging, 23(9): 1365-1379, 15 pages.

Konen et al., 1998, The VN-project: endoscopic image processing for neurosurgery, Computer Aided Surgery, 3:1-6, 6 pages.

Kukuk, Oct. 5, 2001, TBNA-protocols: Guiding TransBronchial Needle Aspirations Without a Computer in the Operating Room, MICCAI 2001, 2208:997-1006, 10 pages.

Kumar et al., 2014, Stereoscopic visualization of laparoscope image using depth information from 3D model, Computer methods and programs in biomedicine 113(3):862-868, 7 pages.

Lawton et al., 1999, Ribbons and groups: A thin rod theory for catheters and filaments, J. Phys. A., 1999, 32:1709-1735, 27 pages.

Livatino et al., 2015, Stereoscopic visualization and 3-D technologies in medical endoscopic teleoperation, IEEE, 11 pages.

Luo et al., 2010, Modified hybrid bronchoscope tracking based on sequential monte carlo sampler: Dynamic phantom validation, Asian Conference on Computer Vision. Springer, Berlin, Heidelberg, 13 pages.

Marrouche et al., dated May 6, 2005, AB32-1, Preliminary human experience using a novel robotic catheter remote control. Heart Rhythm, 2(5):S63.

Mayo Clinic, Robotic Surgery, https://www.mayoclinic.org/tests-procedures/robotic-surgery/about/pac-20394974?p=1, downloaded from the internet on Jul. 12, 2018, 2 pp.

Mourgues et al., 2002, Flexible calibration of actuated stereoscopic endoscope for overlay in robot 672 assisted surgery, International Conference on Medical Image Computing and Computer-Assisted Intervention. SprinQer, Berlin, HeidelberQ, 10 pages.

Nadeem et al., 2016, Depth Reconstruction and Computer-Aided Polyp Detection in Optical Colonoscopy Video Frames, arXiv preprint arXiv:1609.01329, 12 pages.

Non-Final Office Action for U.S. Appl. No. 17/130,700 dated Apr. 5, 2021, 11 pages.

Oh et al., dated May 2005, P5-75, Novel robotic catheter remote control system: safety and accuracy in delivering RF Lesions in all 4 cardiac chambers, Heart Rhythm, 2(5):S277-S278, 2 pages.

Point Cloud, Sep. 10, 2010, Wikipedia, 2 pp.

Racadio et al., Dec. 2007, Live 3D guidance in the interventional radiology suite, AJR, 189:W357-W364, 8 pages.

Reddy et al., May 2005, P1-53. Porcine pulmonary vein ablation using a novel robotic catheter control system and realtime integration of CT imaging with electroanatomical mapping, Hearth Rhythm, 2(5):S121, 1 page.

Sasaki, 2017, Laparoscopic hemicolectomy for a patient with situs inversus totalis: a case report, Int. J. Surg. Case Rep. 41:93-96, 4 pages.

Sato et al., 2016, Techniques of stapler-based navigational thoracoscopic segmentectomy using virtual assisted lung mapping (VAL-MAP), Journal of Thoracic Disease, 8(Suppl 9):S716, 15 pages.

Shen et al., 2015, Robust camera localisation with depth reconstruction for bronchoscopic navigation. International Journal of Computer Assisted Radiology and Surgery, 10(6):801-813, 13 pages.

Shi et al., Sep. 14-18, 2014, Simultaneous catheter and environment modeling for trans-catheter aortic valve implantation, IEEE/RSJ International Conference on Intelligent Robots and Systems, pp. 2024-2029, 6 pages.

Slepian, dated 2010, Robotic Catheter Intervention: the Hansen Medical Sensei Robot Catheter System, PowerPoint presentation, 28 pp.

Solheim et al., May 14, 2009, Navigated resection of giant intracranial meningiomas based on intraoperative 3D ultrasound, Acta Neurochir, 151 :1143-1151, 9 pages.

Solomon et al., Dec. 2000, Three-dimensional CT- Guided Bronchoscopy With a Real-Time Electromagnetic Position Sensor A Comparison of Two Image Registration Methods, Chest, 118(6):1783-1787, 5 pages.

Song et al., 2012, Autonomous and stable tracking of endoscope instrument tools with monocular camera, Advanced Intelligent Mechatronics (AIM), 2012 IEEE-ASME International Conference on IEEE, 6 pages.

Vemuri et al., Dec. 2015, Inter-operative biopsy site relocations in endoluminal surgery, IEEE Transactions on Biomedical Engineering, Institute of Eleclrical and Electronics Engineers, < 10 .1109/T8ME 2015.2503981 >, 13 pages.

Verdaasdonk et al., Jan. 23, 2012, Effect of microsecond pulse length and tip shape on explosive bubble formation of 2.78 μm Er,Cr;YSGG and 2 94 μm Er:YAG laser, Proceedings of SPIE, vol. 8221. 12, 1 page.

Wilson et al., 2008, a buyer's guide to electromagnetic tracking systems for clinical applications, Proc. of SPCI, 6918:691828-1 p. 69188-11, 12 pages.

(56) References Cited

OTHER PUBLICATIONS

Yip et al., 2012, Tissue tracking and registration for image-guided surgery, IEEE transactions on medical imaging 31 (11):2169-2182, 14 pages.
Zhou et al., 2010, Synthesis of stereoscopic views from monocular endoscopic videos, Computer Vision and Pattern Recognition Workshops (CVPRW), 2010 IEEE Computer Society Conference on IEEE, 8 pages.
Notice of Allowance for U.S. Appl. No. 17/130,700, dated Jul. 8, 2021, 5 pages.
Notice of allowance for U.S. Appl. No. 17/130,700, dated Oct. 29, 2021, 5 pages.
Office Action for U.S. Appl. No. 16/586,198, dated Aug. 9, 2021, 47 pages.
Office action for U.S. Appl. No. 17/130,700, dated Apr. 5, 2021, 11 pages.
Office Action for U.S. Appl. No. 17/130,700, dated Sep. 15, 2021, 11 pages.
Office Action for U.S. Appl. No. 16/586,198 dated Dec. 31, 2019, 31 pages.
Office Action for U.S. Appl. No. 16/586,198 dated Feb. 2, 2021, 40 pages.
Office Action for U.S. Appl. No. 16/586,198 dated Jul. 23, 2020, 34 pages.
International Search Report for PCT/IB2020/062360, dated Apr. 1, 2021, 3 pages.
Non-Final Rejection for U.S. Appl. No. 16/586,198, dated Mar. 1, 2022, 54 pages.
Notice of Allowance for U.S. Appl. No. 17/130,700, dated Feb. 18, 2022, 5 pages.
Search Report for Appl. No. PCT/IB2020/062359, dated Jul. 8, 2021, 3 pages.
Written Opinion for Appl. No. PCT/IB2020/062359, dated Apr. 1, 2021, 3 pages.
Written Opinion for PCT/IB2020/062360, dated Apr. 1, 2021, 3 pages.
European Search Report for Appl. No. 19867337.8, dated May 27, 2022, 10 pages.
International Preliminary Report on Patentability and Written Opinion for Appl. No. PCT/IB2020/062359, dated Jul. 5, 2022, 4 pages.
International Preliminary Report on Patentability and Written Opinion for Appl. No. PCT/IB2020/062360, dated Jul. 5, 2022, 4 pages.
International search report and written opinion dated Dec. 18, 2019 for PCT/US2019/53600, 13 pages.
Notice of Allowance for U.S. Appl. No. 17/130,700, dated Jun. 16, 2022, 2 pages.
Notice of Allowance for U.S. Appl. No. 17/130,700, dated Jun. 3, 2022, 5 pages.
Final Rejection for U.S. Appl. No. 16/586,198, dated Sep. 30, 2022, 52 pages.
Notice of Allowance for U.S. Appl. No. 17/130,700, dated Nov. 3, 2022, 5 pages.

* cited by examiner

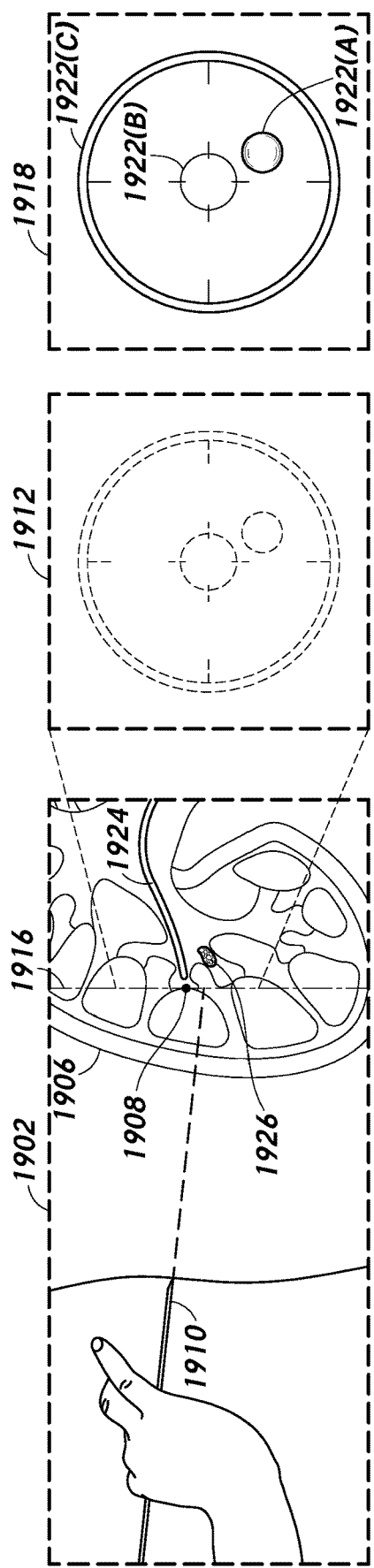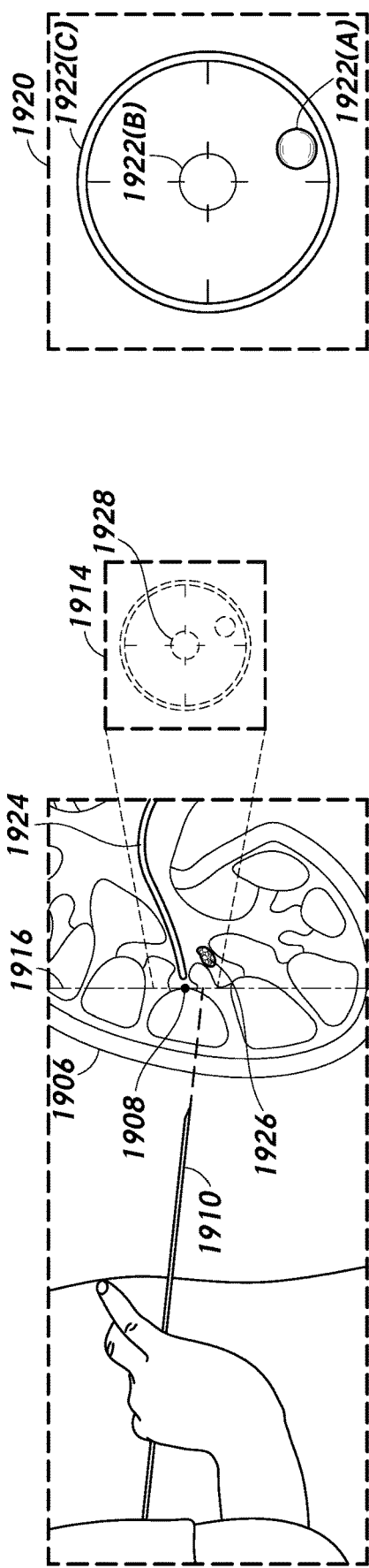
FIG. 19-1
FIG. 19-2

ALIGNMENT TECHNIQUES FOR PERCUTANEOUS ACCESS

RELATED APPLICATION(S)

This application claims priority to U.S. Provisional Application No. 62/956,019, filed Dec. 31, 2019, and entitled ALIGNMENT TECHNIQUES FOR PERCUTANEOUS ACCESS, the disclosure of which is hereby incorporated by reference in its entirety.

BACKGROUND

Field

The present disclosure relates to the field of medical procedures.

Description of the Related Art

Various medical procedures involve the use of one or more devices configured to penetrate the human anatomy to reach a treatment site. Certain operational processes can involve inserting the one or more devices through the skin and other anatomy of a patient to reach the treatment site and extract an object from the patient, such as a urinary stone.

SUMMARY

In some implementations, the present disclosure relates to a method comprising, by control circuitry of a medical system: receiving sensor data indicating a position of at least a portion of a medical instrument, based at least in part on the sensor data, determining an orientation of the medical instrument, determining a target location within an organ of the patient, and determining a plane that includes the target location. The method further comprises, based at least in part on the orientation of the medical instrument, determining a projected position of the medical instrument on the plane, generating interface data representing one or more interface elements indicating a first distance between the projected position and the target location on the plane; and displaying the one or more interface elements based at least in part on the interface data.

In some embodiments, the determining the plane includes determining the plane such that a heading of the medical instrument is normal to the plane. The method can further comprise updating an orientation of the plane as the orientation of the medical instrument changes such that the heading of the medical instrument remains normal to the plane.

In some embodiments, the determining the plane includes determining a line between a distal end of the medical instrument and the target location and determining the plane such that the line is normal to the plane. The method can further comprise maintaining an orientation of the plane as the orientation of the medical instrument changes.

In some embodiment, the determining the target location is based at least in part on additional sensor data from a scope. Further, the determining the plane includes determining the plane such that a heading of the scope is normal to the plane.

In some embodiments, the displaying the one or more interface elements includes displaying a first interface element of the one or more interface elements a second distance from a center of a second interface element of the one or more interface elements. The second distance can be based at least in part on the first distance and an insertion distance between a tip of the medical instrument and the target location on the plane.

In some embodiments, the method further comprises displaying a progress indicator indicating a proximity of a tip of the medical instrument to the target location, setting a progress change parameter for the progress indicator to a first value, the progress change parameter being indicative of an amount of progress change of the progress indicator with respect to a unit of movement of the medical instrument, determining that the tip of the medical instrument has moved closer to the target location, and based at least in part on determining that the tip of the medical instrument has moved closer to the target location, setting the progress change parameter to a second value. The second value can be associated with a greater amount of progress change of the progress indicator for the unit of movement of the medical instrument than the first value.

In some implementations, the present disclosure relates to a medical system comprising a communication interface configured to receive sensor data from a medical instrument that is configured to access a human anatomy percutaneously, and control circuitry communicatively coupled to the communication interface. The control circuitry is configured to based at least in part on the sensor data, determine an orientation of the medical instrument, determine a target location within the human anatomy, determine a plane that includes the target location, based at least in part on the orientation of the medical instrument, determine a projected position of the medical instrument on the plane; and generate interface data representing one or more interface elements indicating a distance between the projected position and the target location on the plane.

In some embodiments, the medical system further comprises an endoscope configured to access the target location via a lumen of the human anatomy. The endoscope can include a sensor that is configured to provide additional sensor data to the communication interface. The control circuitry can be configured to determine the target location based at least in part on the additional sensor data.

In some embodiments, the control circuitry is configured to determine the plane such that a heading of the medical instrument is normal to the plane. The control circuitry can be further configured to update an orientation of the plane as the orientation of the medical instrument changes such that the heading of the medical instrument remains normal to the plane.

In some embodiments, the control circuitry is configured to determine the plane by determining a line between a distal end of the medical instrument and the target location and determining the plane such that the line is normal to the plane. The control circuitry can be further configured to maintain an orientation of the plane as the orientation of the medical instrument changes.

In some embodiments, the medical system includes a robotic system coupled to a device that is configured to generate a signal and the sensor data is based at least in part on the signal. The control circuitry can be further configured to determine a coordinate frame for the medical instrument based at least in part on a coordinate frame for the robotic system, and cause the one or more interface elements to move within an interface in a direction that is correlated to a direction of movement of the medical instrument relative to the coordinate frame for the medical instrument.

In some embodiments, the control circuitry is further configured to set a position change parameter to a first value, determine that the medical instrument has moved closer to the target location, and set the position change parameter to a second value. The position change parameter can be indicative of an amount of position change of the one or more interface elements within an interface with respect to a unit of movement of the medical instrument. The second value can be associated with a greater amount of position change of the one or more interface elements within the interface for the unit of movement of the medical instrument than the first value.

In some embodiments, the control circuitry is further configured to cause a progress indicator to be displayed indicating a proximity of the medical instrument to the target location, set a progress change parameter for the progress indicator to a first value, determine that the medical instrument has moved closer to the target location, and set the progress change parameter to a second value. The progress change parameter can be indicative of an amount of progress change of the progress indicator with respect to a unit of movement of the medical instrument. The second value can be associated with a greater amount of progress change of the progress indicator for the unit of movement of the medical instrument than the first value.

In some implementations, the present disclosure relates to one or more non-transitory computer-readable media storing computer-executable instructions that, when executed by control circuitry, cause the control circuitry to perform operations comprising determining an orientation of a medical instrument that is configured to access a human anatomy percutaneously, determining a target location within the human anatomy, determining a plane that includes the target location, based at least in part on the orientation of the medical instrument, determining a projected position of the medical instrument on the plane, and generating interface data representing one or more interface elements indicating a first distance between the projected position and the target location on the plane.

In some embodiments, a heading of the medical instrument is normal to the plane. The operations can further comprise updating an orientation of the plane as the orientation of the medical instrument changes such that the heading of the medical instrument remains normal to the plane.

In some embodiments, the plane is normal to a line between a distal end of the medical instrument and the target location. The operations can further comprise maintaining an orientation of the plane as the orientation of the medical instrument changes.

In some embodiments, the operations further comprise displaying a first interface element of the one or more interface elements a second distance from a center of a second interface element of the one or more interface elements. The second distance can be based at least in part on the first distance. The second distance can be further based at least in part on an insertion distance between a tip of the medical instrument and the target location on the plane.

In some embodiments, the operations further comprise causing a progress indicator to be displayed indicating a proximity of the medical instrument to the target location, based at least in part on the medical instrument moving closer to the target location a first time by a first amount, updating the progress indicator by a second amount, and based at least in part on the medical instrument moving closer to the target location a second time by the first amount, updating the progress indicator by a third amount that is greater than the first amount.

In some embodiments, the operations further comprise generating progress region data indicating multiple regions for an environment of the medical instrument, based at least in part on the first sensor data and the progress region data, determining a region, from among the multiple regions, in which the medical instrument is located, determining a state of the medical instrument based at least in part on the region, and causing an indication to be displayed of the state.

In some implementations, the present disclosure relates to a method comprising receiving, by control circuitry of a medical system, first sensor data from a needle that is configured to be inserted into a patient percutaneously, based at least in part on the first sensor data, determining, by the control circuitry, a pose of the needle, receiving, by the control circuitry, second sensor data from an endoscope that is disposed at least partially within an anatomical lumen of the patient, based at least in part on the second sensor data, determining, by the control circuitry, a target location within an organ of the patient, determining, by the control circuitry, a plane that includes the target location, based at least in part on the pose of the needle, determining, by the control circuitry, a projected position of the needle on the plane, and generating interface data representing one or more interface elements indicating a distance between the projected position and the target location on the plane.

In some embodiments, the method further comprises displaying the one or more interface elements in an interface, identifying a scaling ratio of dimensions represented on the plane to dimensions represented on the interface, determining that the needle has moved closer to the target location; and based at least in part on determining that the needle has moved closer to the target location, updating the scaling ratio.

In some embodiments, the method further comprises setting a position change parameter to a first value, determining that the medical instrument has moved closer to the target location, based at least in part on determining that the medical instrument has moved closer to the target location, setting the position change parameter to a second value. The position change parameter can be indicative of an amount of position change of the one or more interface elements within an interface with respect to a unit of position or orientation change of the needle. The second value can be associated with a greater amount of position change of the one or more interface elements within the interface for the unit of position or orientation change of the needle than the first value.

In some embodiments, the medical system includes a robotic arm coupled to an electromagnetic field generator, and the first sensor data is based at least in part on electromagnetic fields from the electromagnetic field generator. The method can further comprise determining a world coordinate frame for a robotic system associated with the robotic arm, representing the pose of the needle in the world coordinate frame, representing the plane in the world coordinate frame, determining a target coordinate frame for the plane represented in the world coordinate frame based at least in part on the pose of the needle within the world coordinate frame, determining a coordinate frame for the needle based at least in part on the target coordinate frame, and moving the one or more interface elements within an interface in a direction that is correlated to a direction of movement of the needle relative to the coordinate frame for the needle.

For purposes of summarizing the disclosure, certain aspects, advantages and features have been described. It is to be understood that not necessarily all such advantages may be achieved in accordance with any particular embodiment.

Thus, the disclosed embodiments can be carried out in a manner that achieves or optimizes one advantage or group of advantages as taught herein without necessarily achieving other advantages as can be taught or suggested herein.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

FIGS. 6-1 through 6-11 illustrate example interfaces to provide information regarding an alignment and/or a progress of a medical instrument during a procedure in accordance with one or more embodiments.

FIG. 7 illustrates an example flow diagram of a process for determining an alignment of a medical instrument relative to a target trajectory and presenting information regarding the alignment in accordance with one or more embodiments.

FIG. 8 illustrates an example flow diagram of a process for presenting information regarding an orientation of a medical instrument in accordance with one or more embodiments.

FIG. 9 illustrates an example flow diagram of a process for presenting information regarding a proximity of a medical instrument to a target location in accordance with one or more embodiments.

FIG. 10 illustrates an example flow diagram of a process for setting and/or updating a position change parameter associated with an instrument-alignment element in accordance with one or more embodiments.

FIG. 11 illustrates example details of the robotic system of FIG. 1 in accordance with one or more embodiments.

FIGS. 13-1 through 13-3 illustrate example techniques of mapping a pose of a medical instrument onto a representation/plane that remains fixed as the pose of the medical instrument changes in accordance with one or more embodiments.

FIGS. 14-1 through 14-3 illustrate example techniques of mapping a pose of a medical instrument onto a representation/plane that updates as the pose of the medical instrument changes in accordance with one or more embodiments.

FIGS. 15-1 through 15-3 illustrate another example of mapping a pose of a medical instrument onto a representation/plane that updates as the pose of the medical instrument changes in accordance with one or more embodiments.

FIGS. 16-1 through 16-3 illustrate a further example of mapping a pose of a medical instrument onto a representation/plane that updates as the pose of the medical instrument changes in accordance with one or more embodiments.

FIGS. 19-1 and 19-2 illustrate example techniques of scaling a target plane based on an insertion distance of a medical instrument in accordance with one or more embodiments.

FIG. 19-3 illustrates an example graph of a scaling of a target plane relative to a distance of a medical instrument to a target location in accordance with one or more embodiments.

DETAILED DESCRIPTION

Figure 1:
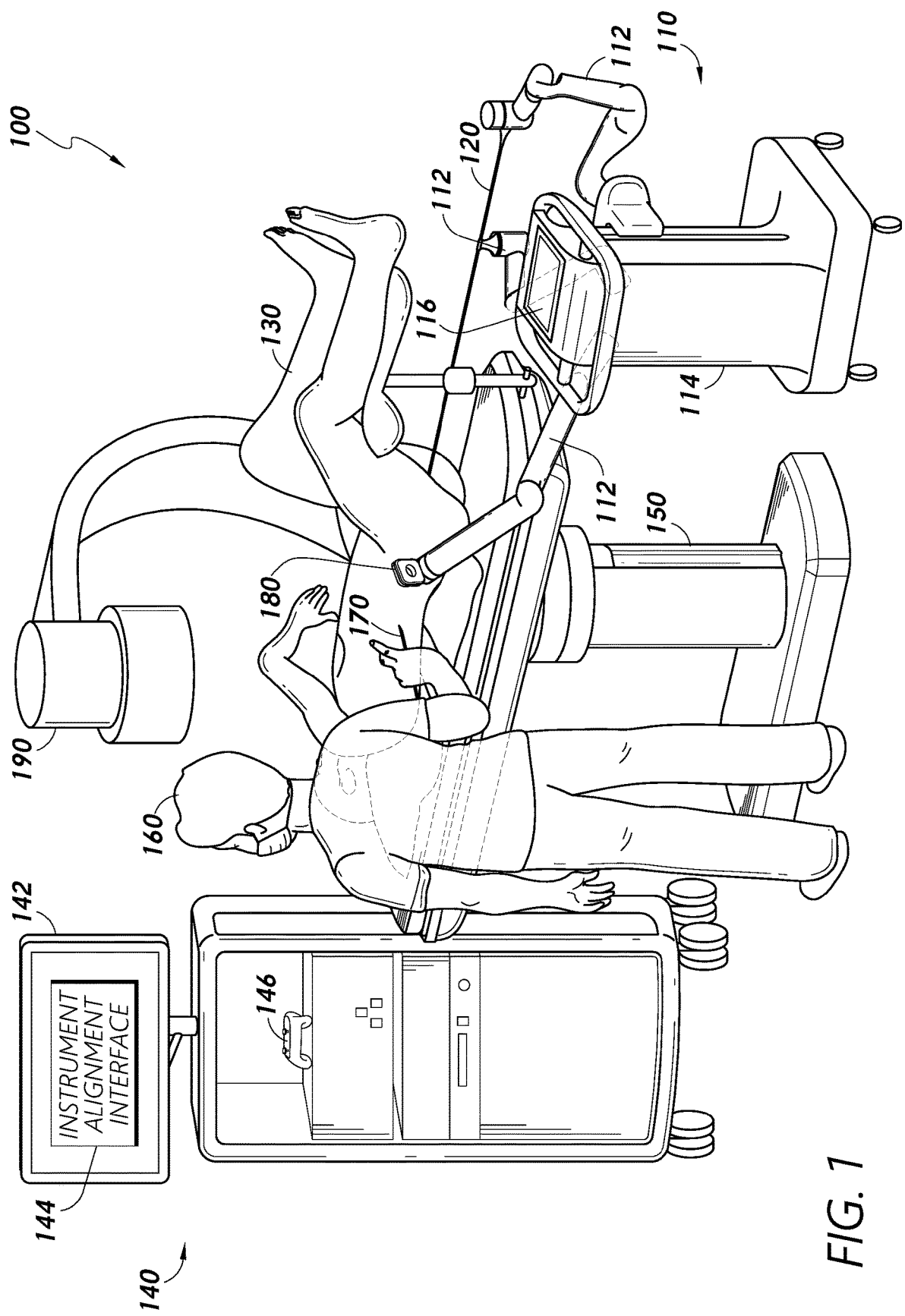
FIG. 1 illustrates an embodiment of a medical system configured to implement the techniques discussed herein in accordance with one or more embodiments.

The headings provided herein are for convenience only and do not necessarily affect the scope or meaning of disclosure. Although certain preferred embodiments and examples are disclosed below, the subject matter extends beyond the specifically disclosed embodiments to other alternative embodiments and/or uses and to modifications and equivalents thereof. Thus, the scope of the claims that may arise here from is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location may be used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Overview

The present disclosure relates to systems, devices, and methods for assisting a physician or other user in aligning a medical instrument for percutaneous access to a location within the human anatomy. Although certain aspects of the present disclosure are described in detail herein in the context of renal, urological, and/or nephrological procedures, such as kidney stone removal/treatment procedures, it should be understood that such context is provided for convenience and clarity, and the concepts disclosed herein are applicable to any suitable medical procedure. However, as mentioned, description of the renal/urinary anatomy and associated medical issues and procedures is presented below to aid in the description of the concepts disclosed herein.

Kidney stone disease, also known as urolithiasis, is a relatively common medical condition that involves the formation, in the urinary tract, of a solid piece of material, referred to as "kidney stones," "urinary stones," "renal calculi," "renal lithiasis," or "nephrolithiasis." Urinary stones can be formed and/or found in the kidneys, the ureters, and the bladder (referred to as "bladder stones"). Such urinary stones form as a result of concentrated minerals and can cause significant abdominal pain once they reach a size sufficient to impede urine flow through the ureter or urethra. Urinary stones can be formed from calcium, magnesium, ammonia, uric acid, cysteine, and/or other compounds.

To remove urinary stones from the bladder and ureter, surgeons can insert a ureteroscope into the urinary tract through the urethra. Typically, a ureteroscope includes an endoscope at its distal end configured to enable visualization of the urinary tract. The ureteroscope can also include a lithotomy mechanism to capture or break apart urinary stones. During a ureteroscopy procedure, one physician/technician can control the position of the ureteroscope, while another other physician/technician can control the lithotomy mechanism.

In order to remove relatively large stones from the kidneys (i.e., "kidney stones"), physicians can use a percutaneous nephrolithotomy ("PCNL") technique that includes inserting a nephroscope through the skin to break up and/or remove the stone(s). Locating the kidney stone(s) can be achieved using fluoroscopy to provide a target for insertion of the nephroscope. However, fluoroscopy increases the cost of the nephrolithotomy procedure due to the cost of the fluoroscope itself as well as the cost of a technician to operate the fluoroscope. Fluoroscopy also exposes the patient to radiation for a prolonged period of time. Even with fluoroscopy, accurately making a percutaneous incision to access the kidney stone can be difficult and undesirably imprecise. Furthermore, some nephrolithotomy techniques involve a two-day or three-day inpatient stay. In sum, certain nephrolithotomy techniques can be relatively costly and problematic for patients.

In some implementations, the present disclosure relates to techniques and systems to assist in aligning a medical instrument for percutaneous access to a target location within the human anatomy. For example, to perform a medical procedure, a physician or other user can use a medical instrument to access a target location within a patient, such as to remove a kidney stone located within the kidneys. The target location can represent a desired location for the medical instrument to access the anatomy of the patient, such as a desired papilla or other location within the kidney. The techniques and systems discussed herein can provide information regarding an orientation/position of the medical instrument to assist the physician or other user in aligning the medical instrument with the appropriate orientation and/or inserting the medical instrument into the patient to reach the target location. For example, the techniques and systems can provide a visual representation indicating a current orientation of the medical instrument relative to a target trajectory/pose, a visual representation indicating a proximity of the medical instrument to the target location, and/or other information regarding the medical instrument and/or procedure. The target trajectory can represent a desired path for accessing the target location from an entry point on the patient, such as from a position on the skin of the patient. By providing such information, the physician or other user can accurately maneuver/manipulate the medical instrument to reach the target location and perform the medical procedure in a manner that minimizes damage to the anatomy of the patient.

In many embodiments, the techniques and systems are discussed in the context of a percutaneous procedure, which can include any procedure where access is gained to a target location by making a puncture and/or incision in the skin, mucous membrane, and/or other body layer. However, it should be understood that the techniques and systems can be implemented in the context of any medical procedure including, for example, minimally invasive procedures (e.g., a laparoscopy), non-invasive procedures (e.g., an endoscopy), therapeutic procedures, diagnostic procedures, percutaneous procedures, non-percutaneous procedures, or other types of procedures. An endoscopic procedure can include a bronchoscopy, a ureteroscopy, a gastroscopy, nephroscopy, nephrolithotomy, and so on. In some embodiments, in the context of a laparoscopic procedure or another procedure, the techniques and systems can be used to align a first medical instrument to a second medical instrument/ anatomical position, such as to guide port placement (e.g., to align a first trocar to a second trocar/anatomical position). Further, in some embodiments, in the context of a diagnostic procedure, the techniques and systems can be used to align an ultrasound probe equipped with an Electromagnetic sensor to an anatomical target or to guide a user to a set of target orientations to reconstruct anatomy, such as three-dimensional (3D) kidney anatomy. Moreover, in some embodiments, in the context of an endoscopic procedure, the techniques and systems can be used to guide a position of a bronchoscope while performing a biopsy at a marked location, such as a location of a tumor.

Medical System

FIG. 1 illustrates an example medical system 100 for performing various medical procedures in accordance with aspects of the present disclosure. The medical system 100 includes a robotic system 110 configured to engage with and/or control a medical instrument 120 to perform a procedure on a patient 130. The medical system 100 also includes a control system 140 configured to interface with the robotic system 110, provide information regarding the procedure, and/or perform a variety of other operations. For example, the control system 140 can include a display(s) 142 to present certain information to assist the physician 160. The medical system 100 can include a table 150 configured to hold the patient 130. The system 100 can further include an electromagnetic (EM) field generator 180, which can be held by one or more robotic arms 112 of the robotic system 110 or can be a stand-alone device. In examples, the medical system 100 can also include an imaging device 190 which can be integrated into a C-arm and/or configured to provide imaging during a procedure, such as for a fluoroscopy-type procedure. Although shown in FIG. 1, in some embodiments the imaging device 190 is eliminated.

In some implementations, the medical system 100 can be used to perform a percutaneous procedure. For example, if the patient 130 has a kidney stone that is too large to be removed through a urinary tract, the physician 160 can perform a procedure to remove the kidney stone through a percutaneous access point on the patient 130. To illustrate, the physician 160 can interact with the control system 140 to control the robotic system 110 to advance and navigate the medical instrument 120 (e.g., a scope) from the urethra, through the bladder, up the ureter, and into the kidney where the stone is located. The control system 140 can provide information via the display(s) 142 regarding the medical instrument 120 to assist the physician 160 in navigating the medical instrument 120, such as real-time images captured therewith.

Once at the site of the kidney stone (e.g., within a calyx of the kidney), the medical instrument 120 can be used to designate/tag a target location for the medical instrument 170 to access the kidney percutaneously (e.g., a desired point to access the kidney). To minimize damage to the kidney and/or the surrounding anatomy, the physician 160 can designate a particular papilla as the target location for entering into the kidney with the medical instrument 170. However, other target locations can be designated or determined. To assist the physician in inserting the medical instrument 170 into the patient 130 through the particular papilla, the control system 140 can provide an instrument alignment interface 144, which can include a visualization to indicate an alignment of an orientation of the medical instrument 170 relative to a target trajectory (e.g., a desired access path), a visualization to indicate a progress of inserting the medical instrument 170 towards the target location, and/or other information. Once the medical instrument 170 has reached the target location, the physician 160 can use the medical instrument 170 and/or another medical instrument to extract the kidney stone from the patient 130, such as through the percutaneous access point.

Although the above percutaneous procedure and/or other procedures are discussed in the context of using the medical instrument 120, in some implementations a percutaneous procedure can be performed without the assistance of the medical instrument 120. Further, the medical system 100 can be used to perform a variety of other procedures.

Moreover, although many embodiments describe the physician 160 using the medical instrument 170, the medical instrument 170 can alternatively be used by a component of the medical system 100. For example, the medical instrument 170 can be held/manipulated by the robotic system 110 (e.g., the one or more robotic arms 112) and the techniques discussed herein can be implemented to control the robotic system 110 to insert the medical instrument 170 with the appropriate orientation to reach a target location.

In the example of FIG. 1, the medical instrument 120 is implemented as a scope and the medical instrument 170 is implemented as a needle. Thus, for ease of discussion, the medical instrument 120 is referred to as "the scope 120" or "the lumen-based medical instrument 120," and the medical instrument 170 is referred to as "the needle 170" or "the percutaneous medical instrument 170." However, the medical instrument 120 and the medical instrument 170 can each be implemented as an suitable type of medical instrument including, for example, a scope (sometimes referred to as an "endoscope"), a needle, a catheter, a guidewire, a lithotripter, a basket retrieval device, forceps, a vacuum, a needle, a scalpel, an imaging probe, jaws, scissors, graspers, needle holder, micro dissector, staple applier, tacker, suction/irrigation tool, clip applier, and so on. In some embodiments, a medical instrument is a steerable device, while other embodiments a medical instrument is a non-steerable device. In some embodiments, a surgical tool refers to a device that is configured to puncture or to be inserted through the human anatomy, such as a needle, a scalpel, a guidewire, and so on. However, a surgical tool can refer to other types of medical instruments.

In some embodiments, a medical instrument, such as the scope 120 and/or the needle 170, includes a sensor that is configured to generate sensor data, which can be sent to another device. In examples, sensor data can indicate a location/orientation of the medical instrument and/or can be used to determine a location/orientation of the medical instrument. For instance, a sensor can include an electromagnetic (EM) sensor with a coil of conductive material. Here, an EM field generator, such as the EM field generator 180, can provide an EM field that is detected by the EM sensor on the medical instrument. The magnetic field can induce small currents in coils of the EM sensor, which can be analyzed to determine a distance and/or angle/orientation between the EM sensor and the EM field generator. Further, a medical instrument can include other types of sensors configured to generate sensor data, such as a camera, a range sensor, a radar device, a shape sensing fiber, an accelerometer, a gyroscope, an accelerometer, a satellite-based positioning sensor (e.g., a global positioning system (GPS)), a radio-frequency transceiver, and so on. In some embodiments, a sensor is positioned on a distal end of a medical instrument, while in other embodiments a sensor is positioned at another location on the medical instrument. In some embodiments, a sensor on a medical instrument can provide sensor data to the control system 140 and the control system 140 can perform one or more localization techniques to determine/track a position and/or an orientation of a medical instrument.

The term "scope" or "endoscope" are used herein according to their broad and ordinary meanings and can refer to any type of elongate medical instrument having image generating, viewing, and/or capturing functionality and configured to be introduced into any type of organ, cavity, lumen, chamber, and/or space of a body. For example, references herein to scopes or endoscopes can refer to a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), a borescope, and so on.

A scope can comprise a tubular and/or flexible medical instrument that is configured to be inserted into the anatomy of a patient to capture images of the anatomy. In some embodiments, a scope can accommodate wires and/or optical fibers to transfer signals to/from an optical assembly and a distal end of the scope, which can include an imaging device, such as an optical camera. The camera/imaging device can be used to capture images of an internal anatomical space, such as a target calyx/papilla of a kidney. A scope can further be configured to accommodate optical fibers to carry light from proximately-located light sources, such as light-emitting diodes, to the distal end of the scope. The distal end of the scope can include ports for light sources to illuminate an anatomical space when using the camera/imaging device. In some embodiments, the scope is configured to be controlled by a robotic system, such as the robotic system 110. The imaging device can comprise an optical fiber, fiber array, and/or lens. The optical components can move along with the tip of the scope such that movement of the tip of the scope results in changes to the images captured by the imaging device.

A scope can be articulable, such as with respect to at least a distal portion of the scope, so that the scope can be steered within the human anatomy. In some embodiments, a scope is configured to be articulated with, for example, five or six degrees of freedom, including X, Y, Z coordinate movement, as well as pitch, yaw, and roll. A position sensor(s) of the scope can likewise have similar degrees of freedom with respect to the position information they produce/provide. A scope can include telescoping parts, such as an inner leader portion and an outer sheath portion, which can be manipulated to telescopically extend the scope. A scope, in some instances, can comprise a rigid or flexible tube, and can be dimensioned to be passed within an outer sheath, catheter, introducer, or other lumen-type device, or can be used without such devices. In some embodiments, a scope includes a working channel for deploying medical instruments (e.g., lithotripters, basketing devices, forceps, etc.), irrigation, and/or aspiration to an operative region at a distal end of the scope.

The robotic system 110 can be configured to at least partly facilitate execution of a medical procedure. The robotic system 110 can be arranged in a variety of ways depending on the particular procedure. The robotic system 110 can include the one or more robotic arms 112 configured to engage with and/or control the scope 120 to perform a procedure. As shown, each robotic arm 112 can include multiple arm segments coupled to joints, which can provide multiple degrees of movement. In the example of FIG. 1, the robotic system 110 is positioned proximate to the patient's 130 legs and the robotic arms 112 are actuated to engage with and position the scope 120 for access into an access point, such as the urethra of the patient 130. When the robotic system 110 is properly positioned, the scope 120 can be inserted into the patient 130 robotically using the robotic arms 112, manually by the physician 160, or a combination thereof. The robotic arms 112 can also be connected to the EM field generator 180, which can be positioned near a treatment site, such as within proximity to the kidneys of the patient 130.

The robotic system 110 can also include a support structure 114 coupled to the one or more robotic arms 112. The support structure 114 can include control electronics/circuitry, one or more power sources, one or more pneumatics, one or more optical sources, one or more actuators (e.g., motors to move the one or more robotic arms 112), memory/data storage, and/or one or more communication interfaces. In some embodiments, the support structure 114 includes an input/output (I/O) device(s) 116 configured to receive input, such as user input to control the robotic system 110, and/or provide output, such as a graphical user interface (GUI), information regarding the robotic system 110, information regarding a procedure, and so on. The I/O device(s) 116 can include a display, a touchscreen, a touchpad, a projector, a mouse, a keyboard, a microphone, a speaker, etc. In some embodiments, the robotic system 110 is movable (e.g., the support structure 114 includes wheels) so that the robotic system 110 can be positioned in a location that is appropriate or desired for a procedure. In other embodiments, the robotic system 110 is a stationary system. Further, in some embodiments, the robotic system 112 is integrated into the table 150.

The robotic system 110 can be coupled to any component of the medical system 100, such as the control system 140, the table 150, the EM field generator 180, the scope 120, and/or the needle 170. In some embodiments, the robotic system is communicatively coupled to the control system 140. In one example, the robotic system 110 can be configured to receive a control signal from the control system 140 to perform an operation, such as to position a robotic arm 112 in a particular manner, manipulate the scope 120, and so on. In response, the robotic system 110 can control a component of the robotic system 110 to perform the operation. In another example, the robotic system 110 is configured to receive an image from the scope 120 depicting internal anatomy of the patient 130 and/or send the image to the control system 140, which can then be displayed on the display(s) 142. Furthermore, in some embodiments, the robotic system 110 is coupled to a component of the medical system 100, such as the control system 140, in such a manner as to allow for fluids, optics, power, or the like to be received therefrom. Example details of the robotic system 110 are discussed in further detail below in reference to FIG. 11.

The control system 140 can be configured to provide various functionality to assist in performing a medical procedure. In some embodiments, the control system 140 can be coupled to the robotic system 110 and operate in cooperation with the robotic system 110 to perform a medical procedure on the patient 130. For example, the control system 140 can communicate with the robotic system 110 via a wireless or wired connection (e.g., to control the robotic system 110 and/or the scope 120, receive an image(s) captured by the scope 120, etc.), provide fluids to the robotic system 110 via one or more fluid channels, provide power to the robotic system 110 via one or more electrical connections, provide optics to the robotic system 110 via one or more optical fibers or other components, and so on. Further, in some embodiments, the control system 140 can communicate with the needle 170 and/or the scope 170 to receive sensor data from the needle 170 and/or the endoscope 120 (via the robotic system 110 and/or directly from the needle 170 and/or the endoscope 120). Moreover, in some embodiments, the control system 140 can communicate with the table 150 to position the table 150 in a particular orientation or otherwise control the table 150. Further, in some embodiments, the control system 140 can communicate with the EM field generator 180 to control generation of an EM field around the patient 130.

The control system 140 includes various I/O devices configured to assist the physician 160 or others in performing a medical procedure. In this example, the control system 140 includes an I/O device(s) 146 that is employed by the physician 160 or other user to control the scope 120, such as to navigate the scope 120 within the patient 130. For example, the physician 160 can provide input via the I/O device(s) 146 and, in response, the control system 140 can send control signals to the robotic system 110 to manipulate the scope 120. Although the I/O device(s) 146 is illustrated as a controller in the example of FIG. 1, the I/O device(s) 146 can be implemented as a variety of types of I/O devices, such as a touchscreen, a touch pad, a mouse, a keyboard, etc.

Figure 2:
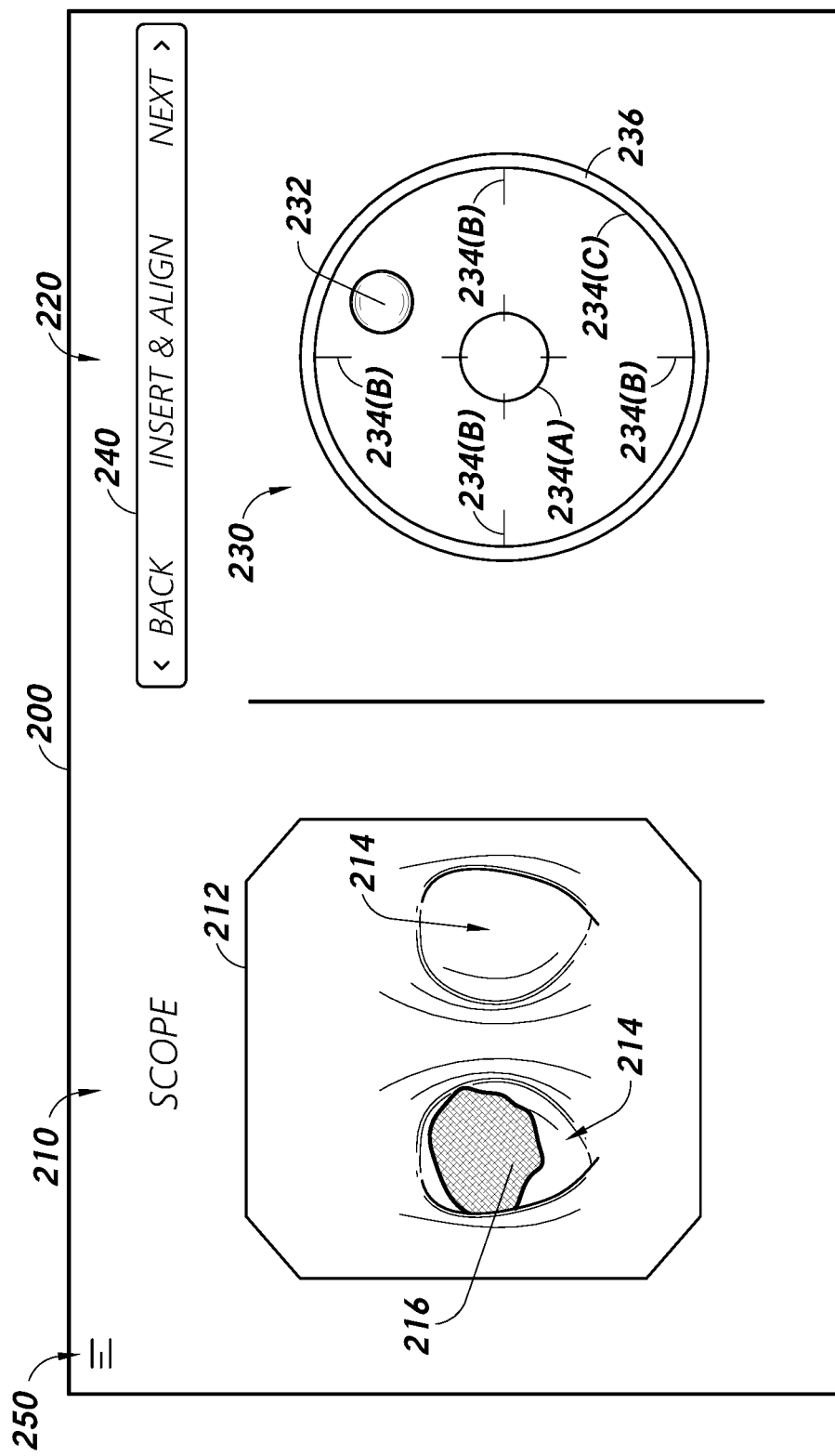
FIG. 2 illustrates an example interface to provide information regarding a position and/or an orientation of a medical instrument in accordance with one or more embodiments.

As also shown in FIG. 1, the control system 140 can include the display(s) 142 to provide various information regarding a procedure. As noted above, the display(s) 142 can present the instrument alignment interface 144 to assist the physician 160 in manipulating the needle 170. The display(s) 142 can also provide (e.g., via the instrument alignment interface 144 and/or another interface) information regarding the scope 120. For example, the control system 140 can receive real-time images that are captured by the scope 120 and display the real-time images via the display(s) 142. An example instrument alignment interface is illustrated in FIG. 2. Additionally or alternatively, the control system 140 can receive signals (e.g., analog, digital, electrical, acoustic/sonic, pneumatic, tactile, hydraulic, etc.) from a medical monitor and/or a sensor associated with the patient 130, and the display(s) 142 can present information regarding the health or environment of the patient 130. Such information can include information that is displayed via a medical monitor including, for example, a heart rate (e.g., ECG, HRV, etc.). blood pressure/rate, muscle bio-signals (e.g., EMG), body temperature, blood oxygen saturation (e.g., $SpO_2$), $CO_2$, brainwaves (e.g., EEG), environmental and/or local or core body temperature, and so on.

To facilitate the functionality of the control system 140, the control system 140 can include various components (sometimes referred to as "subsystems"). For example, the control system 140 can include control electronics/circuitry, as well as one or more power sources, pneumatics, optical sources, actuators, memory/data storage devices, and/or communication interfaces. In some embodiments, the control system 140 includes control circuitry comprising a computer-based control system that is configured to store executable instructions, that when executed, cause various operations to be implemented. In some embodiments, the control system 140 is movable, such as that shown in FIG. 1, while in other embodiments, the control system 140 is a stationary system. Although various functionality and components are discussed as being implemented by the control system 140, any of this functionality and/or components can be integrated into and/or performed by other systems and/or devices, such as the robotic system 110, the table 150, and/or the EM generator 180 (or even the scope 120 and/or the needle 170). Example details of the control system 140 are discussed in further detail below in reference to FIG. 12.

The imaging device 190 can be configured to capture/generate one or more images of the patient 130 during a procedure, such as one or more x-ray or CT images. In examples, images from the imaging device 190 can be provided in real-time to view anatomy and/or medical instruments, such as the scope 120 and/or the needle 170, within the patient 130 to assist the physician 160 in performing a procedure. The imaging device 190 can be used to perform a fluoroscopy (e.g., with a contrast dye within the patient 130) or another type of imaging technique. Although shown in FIG. 1, in many embodiments the imaging device 190 is not implemented for performing a procedure and/or the imaging device 190 (including the C-arm) is eliminated.

The various components of the medical system 100 can be communicatively coupled to each other over a network, which can include a wireless and/or wired network. Example networks include one or more personal area networks (PANs), local area networks (LANs), wide area networks (WANs), Internet area networks (IANs), cellular networks, the Internet, etc. Further, in some embodiments, the components of the medical system 100 are connected for data communication, fluid/gas exchange, power exchange, and so on, via one or more support cables, tubes, or the like.

The medical system 100 can provide a variety of benefits, such as providing guidance to assist a physician in performing a procedure (e.g., instrument tracking, instrument alignment information, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single-operative setting, providing continuous suction to remove an object more efficiently (e.g., to remove a kidney stone), and so on. For example, the medical system 100 can provide guidance information to assist a physician in using various medical instruments to access a target anatomical feature while minimizing bleeding and/or damage to anatomy (e.g., critical organs, blood vessels, etc.). Further, the medical system 100 can provide non-radiation-based navigational and/or localization techniques to reduce physician and patient exposure to radiation and/or reduce the amount of equipment in the operating room. Moreover, the medical system 100 can provide functionality that is distributed between at least the control system 140 and the robotic system 110, which can be independently movable. Such distribution of functionality and/or mobility can enable the control system 140 and/or the robotic system 110 to be placed at locations that are optimal for a particular medical procedure, which can maximize working area around the patient and/or provide an optimized location for a physician to perform a procedure.

Although various techniques and systems are discussed as being implemented as robotically-assisted procedures (e.g., procedures that at least partly use the medical system 100), the techniques and systems can be implemented in other procedures, such as in fully-robotic medical procedures, human-only procedures (e.g., free of robotic systems), and so on. For example, the medical system 100 can be used to perform a procedure without a physician holding/manipulating a medical instrument (e.g., a fully-robotic procedure). That is, medical instruments that are used during a procedure, such as the scope 120 and the needle 170, can each be held/controlled by components of the medical system 100, such as the robotic arm(s) 112 of the robotic system 110.

Example Interface

FIG. 2 illustrates an example instrument-alignment interface 200 to provide information regarding a position and/or an orientation of a medical instrument and/or other information regarding a medical procedure in accordance with one or more embodiments. As shown, the instrument-alignment interface 200 (sometimes referred to as "the instrument-alignment graphical user interface (GUI) 200") can include a scope section 210 to provide an image(s) 212 captured by a first medical instrument, such as a scope, and an alignment section 220 to provide information regarding an orientation of a second medical instrument, such as a needle. Although the scope section 210 and the alignment section 220 are illustrated as being included in the same instrument-alignment interface 200, in some embodiments the instrument-alignment interface 200 includes only one of the sections 210 and 220. For example, the alignment section 220 can be included as part of the instrument-alignment interface 200 and the scope section 210 can be included within an additional interface. Further, in some examples, the scope section 210 and/or the alignment section 220 can be implemented within an augmented or virtual reality interface, such as with the alignment section 220 overlaid onto at least a portion of the scope section 212, with the scope section 212 presented with alignment information in a different form than the alignment section 220, and so on. In the example of FIG. 2, the instrument-alignment interface 200 provides information for a procedure that uses a scope and another medical instrument. However, the instrument-alignment interface 200 can be used for other types of procedures, such as a procedure that is performed without a scope. In such cases, the image(s) 212 may not be presented and/or the scope section 210 may be eliminated.

As noted above, the scope section 212 provides the image(s) 212 for a scope that is configured to navigate within a lumen or other anatomy. In this example, the image(s) 212 depicts an interior portion of a kidney, including cavities 214 and the kidney stone 216 located within one of the cavities 214. Here, the kidney stone 216 is located within a calyx in proximity to a papilla. However, the image(s) 212 can depict any human anatomy depending on a location of the scope within a patient. The image(s) 212 can include a real-time image, such as a video.

The alignment section 220 includes an alignment-progress visualization 230 to indicate an alignment of an orientation of a medical instrument to a target trajectory and/or a proximity of the medical instrument to a target location. As shown, the alignment-progress visualization 230 includes an instrument-alignment element 232 (sometimes referred to as "the instrument-alignment icon 232" or "the needle-alignment icon 232") representing the orientation of the medical instrument and alignment markings 234 associated with the target trajectory. In this example, the instrument-alignment element 232 can move within an area defined by the alignment marking 234(C) (also referred to as "the boundary marking 234(C)") based on a change in the orientation of the medical instrument. For instance, as the medical instrument is tilted, the instrument-alignment element 232 can change position within the area. In examples, the alignment marking 234(A) can represent a target location/trajectory/pose.

In some embodiments, a tilt of the medical instrument in one direction will cause movement of the instrument-alignment element 232 in the opposite direction, similar to a bull's-eye spirit type of level. For example, if the medical instrument is tilted to the right, the instrument-alignment element 232 can move to the left. In other embodiments, a tilt of the medical instrument will cause movement of the instrument-alignment element 232 in the same direction of the tilt. For example, if the medical instrument is tilted to the right, the instrument-alignment element 232 can move to the right. In any event, when the orientation of the medical instrument is aligned with the target trajectory, the instrument alignment element 232 can be displayed in an aligned arrangement with the alignment markings 234 (e.g., centered with the alignment markings 234, such as within or centered on the alignment marking 234(A)).

In some embodiments, an amount of position change of the instrument-alignment element 232 for a unit of orientation change of a medical instrument (e.g., a sensitivity of the instrument-alignment element 232) is based on a proximity of the medical instrument to a target location. For example, as the medical instrument moves closer to the target location, the instrument alignment element 232 can be implemented with larger or smaller movements for a same amount of change in the orientation of the medical instrument. To illustrate, when the medical instrument is a first distance from the target location, the instrument-alignment interface 200 can change a position of the instrument-alignment element 232 by a first amount in response to a unit of change of an orientation of the medical instrument. When the medical instrument is a second distance from the target location (e.g., closer to the target location), the instrument-alignment interface 200 can change a position of the instrument-alignment element 232 by a second amount (e.g., a larger or smaller amount) in response to the same unit of change of the orientation of the medical instrument.

In some embodiments, changing the sensitivity of the instrument-alignment element 232 can further assist a physician in reaching a target location with a medical instrument. For example, in some cases, as a medical instrument is farther from a target, less precision can be needed to orient the medical instrument. While as the medical instrument moves closer to the target location, more precision can be required to orient the medical instrument. In other words, as the medical instrument moves closer to the target, the physician may need to adjust the orientation of the medical instrument more precisely to actually reach the target. As such, by changing the sensitivity of the instrument-alignment element 232, a physician can more accurately maneuver the medical instrument to reach a target location, which can be relatively small.

The alignment-progress visualization 230 can also include a progress bar 236 to indicate a proximity of a medical instrument to a target location. In the example of FIG. 2, the progress bar 236 is presented around the boundary marking 234(C). However, the progress bar 236 can be presented at any location within the instrument-alignment interface 200, such as to the side of the alignment-progress visualization 230. The progress bar 236 can provide current position information for the medical instrument relative to the target location. For example, the progress bar 236 can fill in as the medical instrument moves closer to the target location, as discussed in examples below. In some embodiments, if the medical instrument has reached the target location, the instrument-alignment interface 200 can provide an indication that the medical instrument has reached the target location, such as with an indication on the progress bar 236. In a similar manner, in some embodiments, if the medical instrument is inserted beyond the target location, the instrument-alignment interface 200 can provide an indication that the medical instrument has been inserted beyond the target location, such as with an indication on the progress bar 236. In the example of FIG. 2, the progress bar 236 indicates that the medical instrument has not yet been inserted into a patient (e.g., the medical instrument is on the skin of the patient or otherwise external to the patient).

In some embodiments, the alignment-progress visualization 230 includes a single visualization to view orientation and progress information regarding a medical instrument. For example, information regarding an orientation of the medical instrument and a progress of the instrument to a target location can be displayed in a combined visualization. Such combined visualization can allow a physician or other user to maintain visual contact with a single item while manipulating the medical instrument and avoid inadvertent movements of the medical instrument that can occur due to movement of the physician's eyes or body to view several displays, interfaces, visualizations, etc. As such, the combined visualization can allow the physician or other user to more accurately manipulate the medical instrument to reach a target location within the patient.

In the example of FIG. 2, various components of the alignment-progress visualization 230 are presented with circular shapes. However, any component of the alignment-progress visualization 230 can take a variety of forms, such as any other shape. For example, the alignment markings 234, the instrument-alignment element 232, and/or the progress bar 236 can be presented with a rectangular shape or any other shape. In some implementations, the instrument-alignment element 232 includes a bubble representation representing an air bubble.

As also shown in FIG. 2, the instrument-alignment interface 200 can include navigation representations 240 to navigate between different visualizations associated with different phases/steps of a procedure. For example, a procedure associated with removing a kidney stone can include a variety of phases/steps, with one of the phases/steps including aligning and inserting the medical instrument into the patient to reach a target location. For such phase/step, the instrument-alignment interface 200 can display the information shown in FIG. 2 to assist the physician in performing such phase/step. The physician can move to a different visualization or interface for a previous or next phase/step by selecting the "back" or "next" text within the navigation representations 240. Further, the instrument-alignment interface 200 can include a visual representation 250 to access a menu, which can enable access to interfaces/information associated with other types of procedures or other information.

Although many embodiments are discussed and illustrated in the context of an instrument-alignment interface including two-dimensional (2D) representations, an instrument-alignment interface can include three-dimensional (3D) representations in some embodiments. For example, an instrument-alignment interface can present a plane and distorted lines on the plane to indicate misalignment, present a plane with a shape/form of the plane being configured to distort/change to indicate misalignment, and so on.

In some embodiments, the instrument-alignment interface 200 and/or any other interface discussed herein is based on targeting data and/or interface data. For example, targeting/interface data can be generated that indicates a projected position of a medical instrument on a plane relative to a target location on the plane. The target/interface data can be used to display the alignment-progress visualization 230, such as to position the instrument-alignment element 232 representing the orientation of the medical instrument relative to the alignment markings 234 associated with the target trajectory.

Example Procedure Using a Medical System

Figure 3:
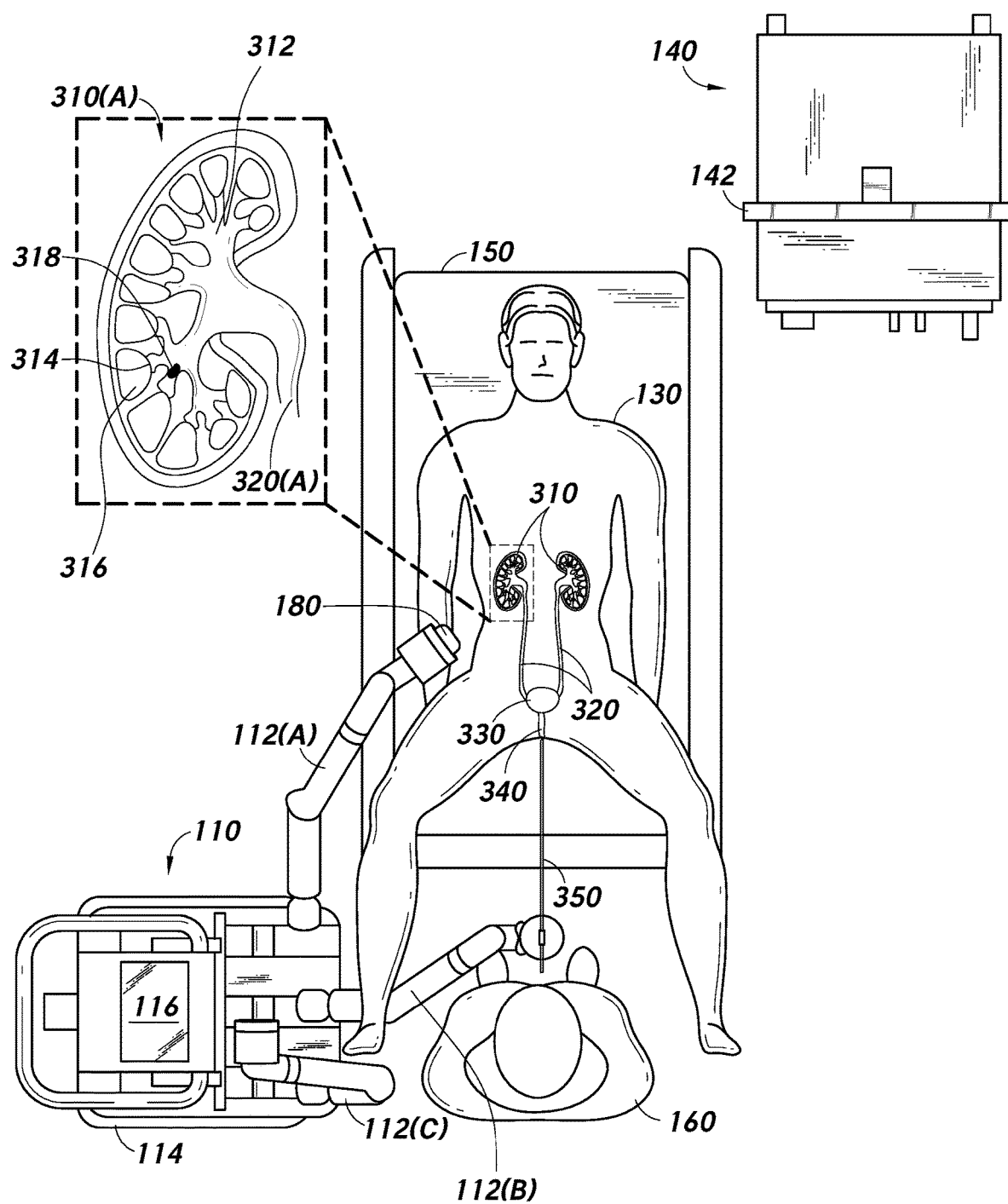
FIG. 3 illustrates a top view of the medical system of FIG. 1 arranged to assist in inserting a scope into a patient in accordance with one or more embodiments.
Figure 4:
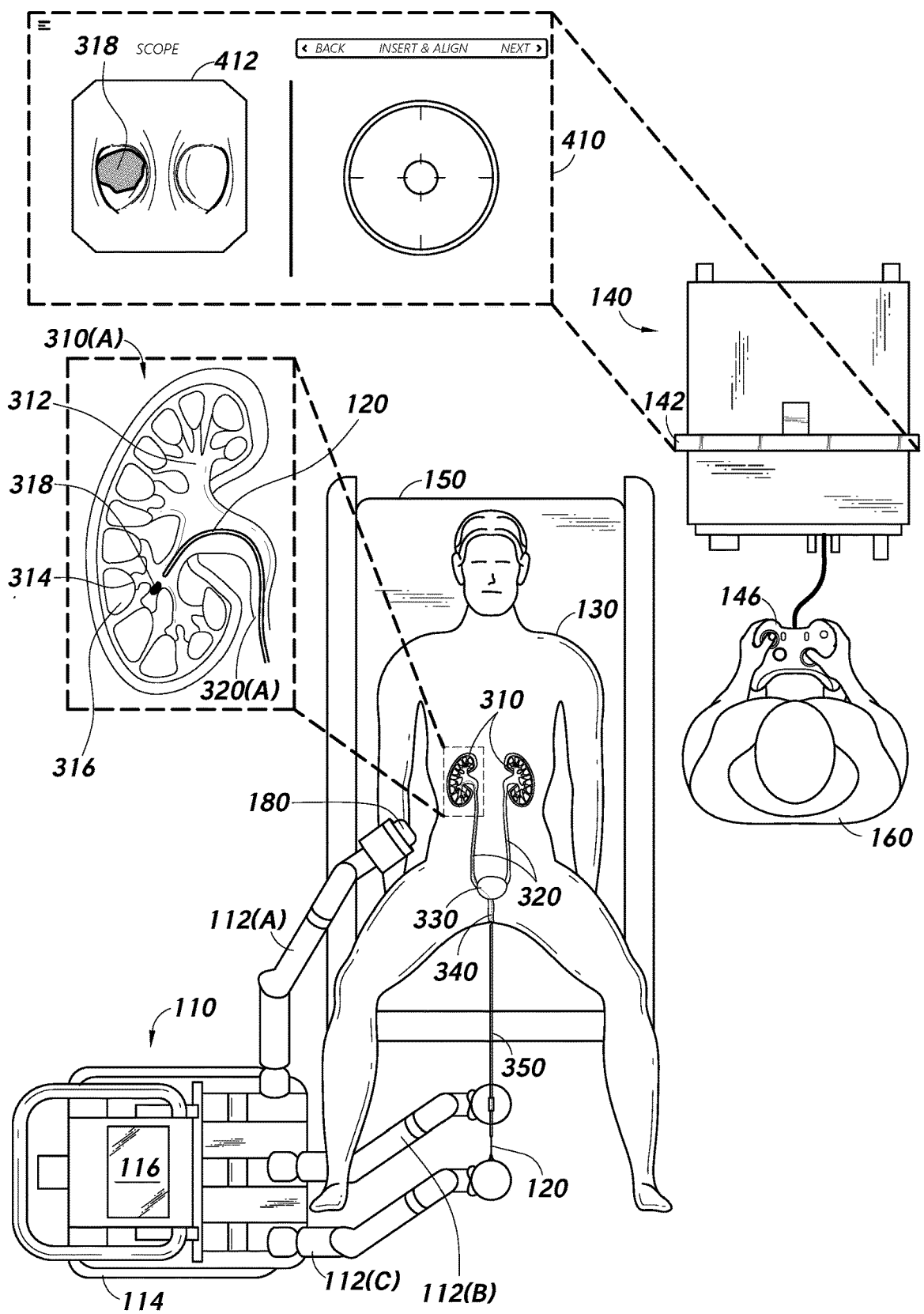
FIG. 4 illustrates a top view of the medical system of FIG. 1 arranged to navigate a scope within a patient in accordance with one or more embodiments.
Figure 5:
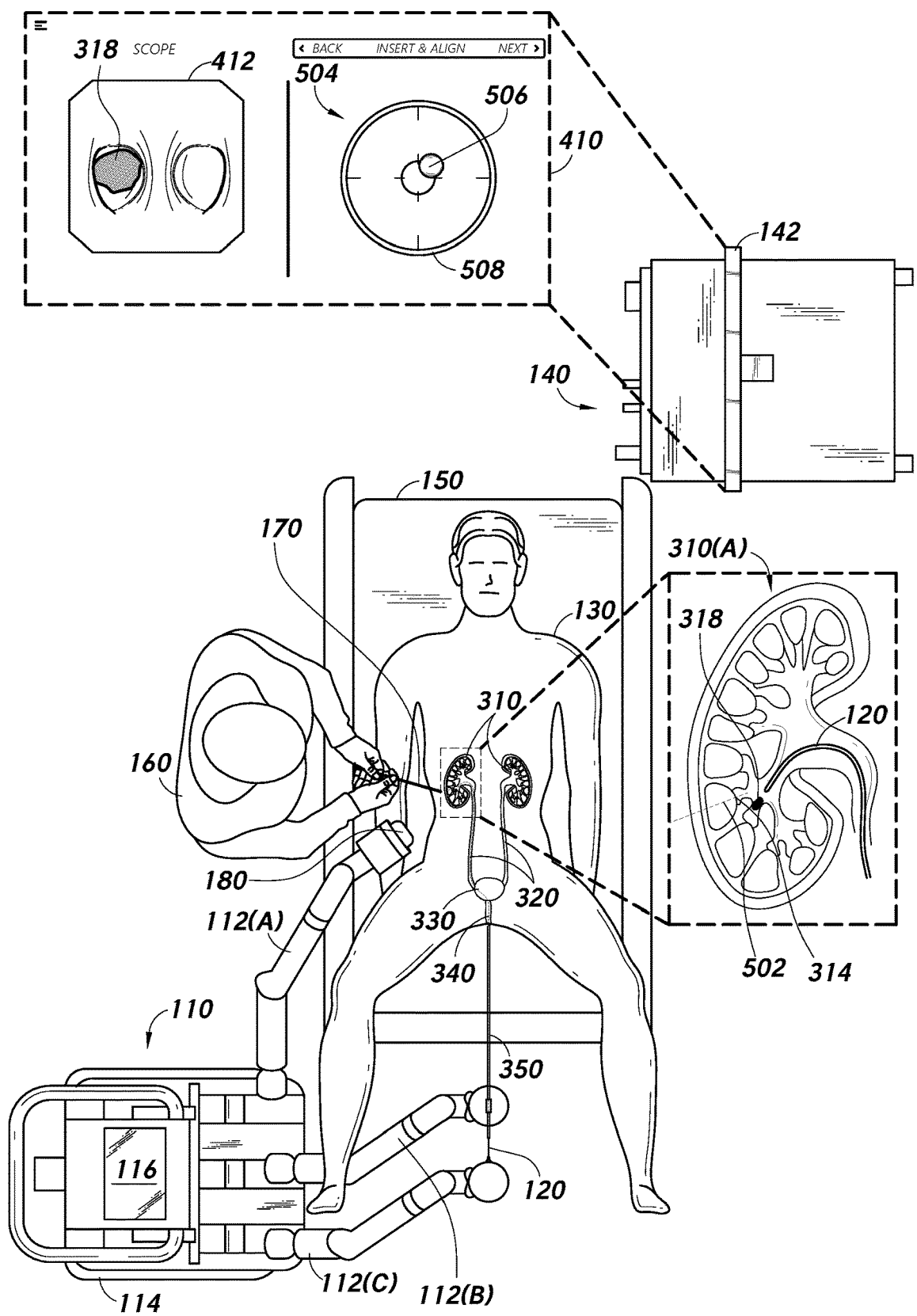
FIG. 5 illustrates a top view of the medical system of FIG. 1 arranged to assist in inserting a needle into a patient in accordance with one or more embodiments.

FIGS. 3-5 illustrate a top view the medical system 100 of FIG. 1 arranged to perform a percutaneous procedure in accordance with one or more embodiments. In these examples, the medical system 100 is arranged in an operating room to remove a kidney stone from the patient 130 with the assistance of the scope 120 and the needle 170. In many embodiments of such procedure, the patient 130 is positioned in a modified supine position with the patient 130 slightly tilted to the side to access the back or side of the patient 130, such as that illustrated in FIG. 1. However, the patient 130 can be positioned in other manners, such as a supine position, a prone position, and so on. For ease of illustration in viewing the anatomy of the patient 130, FIG. 3-5 illustrate the patient 130 in a supine position with the legs spread apart. Also, for ease of illustration, the imaging device 190 (including the C-arm) has been removed.

Although FIGS. 3-5 illustrate use of the medical system 100 to perform a percutaneous procedure to remove a kidney stone from the patient 130, the medical system 100 can be used to remove a kidney stone in other manners and/or to perform other procedures. Further, the patient 130 can be arranged in other positions as desired for a procedure. Various acts are described in FIGS. 3-5 and throughout this disclosure as being performed by the physician 160. It should be understood that these acts can be performed directly by the physician 160, a user under direction of the physician, another user (e.g., a technician), a combination thereof, and/or any other user.

The renal anatomy, as illustrated at least in part in FIGS. 3-5, is described here for reference with respect to certain medical procedures relating to aspects of the present concepts. The kidneys generally comprise two bean-shaped organs located on the left and right in the retroperitoneal space. In adult humans, the kidneys are generally about 11 cm in length. The kidneys receive blood from the paired renal arteries; blood exits into the paired renal veins. Each kidney is attached to a ureter, which is a tube that carries excreted urine from the kidney to the bladder. The bladder is attached to the urethra.

The kidneys are typically located relatively high in the abdominal cavity and lie in a retroperitoneal position at a slightly oblique angle. The asymmetry within the abdominal cavity, caused by the position of the liver, typically results in the right kidney being slightly lower and smaller than the left, and being placed slightly more to the middle than the left kidney. On top of each kidney is an adrenal gland. The upper parts of the kidneys are partially protected by the 11th and 12th ribs. Each kidney, with its adrenal gland is surrounded by two layers of fat: the perirenal fat present between renal fascia and renal capsule and pararenal fat superior to the renal fascia.

The kidney participates in the control of the volume of various body fluid compartments, fluid osmolality, acid-base balance, various electrolyte concentrations, and removal of toxins. The kidneys provide filtration functionality by secreting certain substances and reabsorbing others. Examples of substances secreted into the urine are hydrogen, ammonium, potassium, and uric acid. In addition, the kidneys also carry out various other functions, such as hormone synthesis, and others.

A recessed area on the concave border of the kidney is the renal hilum, where the renal artery enters the kidney and the renal vein and ureter leave. The kidney is surrounded by tough fibrous tissue, the renal capsule, which is itself surrounded by perirenal fat, renal fascia, and pararenal fat. The anterior (front) surface of these tissues is the peritoneum, while the posterior (rear) surface is the transversalis fascia.

The functional substance, or parenchyma, of the kidney is divided into two major structures: the outer renal cortex and the inner renal medulla. These structures take the shape of a plurality of cone-shaped renal lobes, each containing renal cortex surrounding a portion of medulla called a renal pyramid. Between the renal pyramids are projections of cortex called renal columns. Nephrons, the urine-producing functional structures of the kidney, span the cortex and medulla. The initial filtering portion of a nephron is the renal corpuscle, which is located in the cortex. This is followed by a renal tubule that passes from the cortex deep into the medullary pyramids. Part of the renal cortex, a medullary ray is a collection of renal tubules that drain into a single collecting duct.

The tip, or papilla, of each pyramid empties urine into a respective minor calyx; minor calyces empty into major calyces, and major calyces empty into the renal pelvis, which transitions to the ureter. At the hilum, the ureter and renal vein exit the kidney and the renal artery enters. Hilar fat and lymphatic tissue with lymph nodes surrounds these structures. The hilar fat is contiguous with a fat-filled cavity called the renal sinus. The renal sinus collectively contains the renal pelvis and calyces and separates these structures from the renal medullary tissue.

FIGS. 3-5 show various features of the anatomy of the patient 130. For example, the patient 130 includes kidneys 310 fluidly connected to a bladder 330 via ureters 320, and a urethra 340 fluidly connected to the bladder 330. As shown in the enlarged depiction of the kidney 310(A), the kidney 310(A) includes calyces (including calyx 312), renal papillae (including the renal papilla 314, also referred to as "the papilla 314"), and renal pyramids (including the renal pyramid 316). In these examples, a kidney stone 318 is located in proximity to the papilla 314. However, the kidney stone 318 can be located at other locations within the kidney 310(A) or elsewhere.

As shown in FIG. 3, to remove the kidney stone 318 in the example percutaneous procedure, the physician 160 can position the robotic system 110 at the side/foot of the table 150 to initiate delivery of the scope 120 (not illustrated in FIG. 3) into the patient 130. In particular, the robotic system 110 can be positioned at the side of the table 150 within proximity to the feet of the patient 130 and aligned for direct linear access to the urethra 340 of the patient 130. In examples, the hip of the patient 130 is used as a reference point to position the robotic system 110. Once positioned, one or more of the robotic arms 112, such as the robotic arms 112(B) and 112(C), can stretch outwards to reach in between the legs of the patient 130. For example, the robotic arm 112(B) can be controlled to extend and provide linear access to the urethra 340, as shown in FIG. 3. In this example, the physician 160 inserts a medical instrument 350 at least partially into the urethra 340 along this direct linear access path (sometimes referred to as "a virtual rail"). The medical instrument 350 can include a lumen-type device configured to receive the scope 130, thereby assisting in inserting the scope 120 into the anatomy of the patient 130. By aligning the robotic arm 112(B) to the urethra 340 of the patient 130 and/or using the medical instrument 350, friction and/or forces on the sensitive anatomy in the area can be reduced.

Although the medical instrument 350 is illustrated in FIG. 3, in some embodiments, the medical instrument 350 is not used (e.g., the scope 120 can be inserted directly into the urethra 340).

The physician 160 can also position the robotic arm 112(A) near a treatment site for the procedure. For example, the robotic arm 112(A) can be positioned within proximity to the incision site and/or the kidneys 310 of the patient 130. The robotic arm 112(A) can be connected to the EM field generator 180 to assist in tracking a location of the scope 120 and/or the needle 170 during the procedure. Although the robotic arm 112(A) is positioned relatively close to the patient 130, in some embodiments the robotic arm 112(A) is positioned elsewhere and/or the EM field generator 180 is integrated into the table 150 (which can allow the robotic arm 112(A) to be in a docked position). In this example, at this point in the procedure, the robotic arm 112(C) remains in a docked position, as shown in FIG. 3. However, the robotic arm 112(C) can be used in some embodiments to perform any of the functions discussed above of the robotic arms 112(A) and/or 112(C).

Once the robotic system 110 is properly positioned and/or the medical instrument 350 is inserted at least partially into the urethra 340, the scope 120 can be inserted into the patient 130 robotically, manually, or a combination thereof, as shown in FIG. 4. For example, the physician 160 can connect the scope 120 to the robotic arm 112(C) and/or position the scope 120 at least partially within the medical instrument 350 and/or the patient 130. The scope 120 can be connected to the robotic arm 112(C) at any time, such as before the procedure or during the procedure (e.g., after positioning the robotic system 110). The physician 160 can then interact with the control system 140, such as the I/O device(s) 146, to navigate the scope 120 within the patient 130. For example, the physician 160 can provide input via the I/O device(s) 146 to control the robotic arm 112(C) to navigate the scope 120 through the urethra 340, the bladder 330, the ureter 320(A), and up to the kidney 310(A).

As shown, the control system 140 can present an instrument-alignment interface 410, such as the instrument-alignment interface 200 of FIG. 2, via the display(s) 142 to view a real-time image 412 captured by the scope 120 to assist the physician 160 in controlling the scope 120. The physician 160 can navigate the scope 120 to locate the kidney stone 318, as depicted in the image 412. In some embodiment, the control system 140 can use localization techniques to determine a position and/or an orientation of the scope 120, which can be viewed by the physician 160 through the display(s) 142 (not illustrated on the display(s) 142 in FIG. 4) to also assist in controlling the scope 120. Further, in some embodiments, other types of information can be presented through the display(s) 142 to assist the physician 160 in controlling the scope 120, such as x-ray images of the internal anatomy of the patient 130.

Upon locating the kidney stone 318, the physician 160 can identify a location for the needle 170 to enter the kidney 310(A) for eventual extraction of the kidney stone 318. For example, to minimize bleeding and/or avoid hitting a blood vessel or other undesirable anatomy of the kidney 310(A) and/or anatomy surrounding the kidney 310(A), the physician 160 can seek to align the needle 170 with an axis of a calyx (e.g., can seek to reach the calyx head-on through the center of the calyx). To do so, the physician 160 can identify a papilla as a target location. In this example, the physician 160 uses the scope 120 to locate the papilla 314 that is near the kidney stone 318 and designate the papilla 314 as the target location. In some embodiments of designating the papilla 314 as the target location, the physician 160 can navigate the scope 120 to contact the papilla 314, the control system 140 can use localization techniques to determine a location of the scope 120 (e.g., a location of the end of the scope 120), and the control system 140 can associate the location of the scope 120 with the target location. In other embodiments, the physician 160 can navigate the scope 120 to be within a particular distance to the papilla 314 (e.g., park in front of the papilla 314) and provide input indicating that the target location is within a field-of-view of the scope 120. The control system 140 can perform image analysis and/or other localization techniques to determine a location of the target location. In yet other embodiments, the scope 120 can deliver a fiduciary to mark the papilla 314 as the target location.

As shown in FIG. 5, the physician 160 can proceed with the procedure by positioning the needle 170 for insertion into the target location. In some embodiments, the physician 160 can use his or her best judgment to place the needle 170 on the patient 130 at an incision site, such as based on knowledge regarding the anatomy of the patient 130, experience from previously performing the procedure, an analysis of CT/x-ray images or other pre-operative information of the patient 130, and so on. Further, in some embodiments, the control system 140 can provide information regarding a location to place the needle 170 on the patient 130. The physician 160 can attempt to avoid critical anatomy of the patient 130, such as the lungs, pleura, colon, paraspinal muscles, ribs, intercostal nerves, etc. In some examples, the control system 140 can use CT/x-ray/ultrasound images to provide information regarding a location to place the needle 170 on the patient 130.

In any event, the control system 140 can determine a target trajectory 502 for inserting the needle 170 to assist the physician 160 in reaching the target location (i.e., the papilla 314). The target trajectory 502 can represent a desired path for accessing to the target location. The target trajectory 502 can be determined based on a position of a medical instrument (e.g., the needle 170, the scope 120, etc.), a target location within the human anatomy, a position and/or orientation of a patient, the anatomy of the patient (e.g., the location of organs within the patient relative to the target location), and so on. In this example, the target trajectory 502 includes a straight line that passes through the papilla 314 and the needle 170 (e.g., extends from a tip of the needle 170 through the papilla 314, such as a point on an axis of the papilla 314). However, the target trajectory 502 can take other forms, such as a curved line, and/or can be defined in other manners. In some examples, the needle 170 is implemented a flexible bevel-tip needle that is configured to curve as the needle 170 is inserted in a straight manner. Such needle can be used to steer around particular anatomy, such as the ribs or other anatomy. Here, the control system 140 can provide information to guide a user, such as to compensate for deviation in the needle trajectory or to maintain the user on the target trajectory.

Although the example of FIG. 5 illustrates the target trajectory 502 extending coaxially through the papilla 314, the target trajectory 502 can have another position, angle, and/or form. For example, a target trajectory can be implemented with a lower pole access point, such as through a papilla located below the kidney stone 318 shown in FIG. 5, with a non-coaxial angle through the papilla, which can be used to avoid the hip.

The control system 140 can use the target trajectory 502 to provide an alignment-progress visualization 504 via the instrument-alignment interface 410. For example, the alignment-progress visualization 504 can include an instrument alignment element 506 indicative of an orientation of the needle 170 relative to the target trajectory 502. The physician 160 can view the alignment-progress visualization 504 and orient the needle 170 to the appropriate orientation (i.e., the target trajectory 502). When aligned, the physician 160 can insert the needle 170 into the patient 130 to reach the target location. The alignment-progress visualization 504 can provide a progress visualization 508 (also referred to as "the progress bar 508") indicative of a proximity of the needle 170 to the target location. As such, the instrument-alignment interface 410 can assist the physician 160 in aligning and/or inserting the needle 170 to reach the target location.

Once the target location has been reached with the needle 170, the physician 160 can insert another medical instrument, such as a power catheter, vacuum, nephroscope, etc., into the path created by the needle 170 and/or over the needle 170. The physician 160 can use the other medical instrument and/or the scope 120 to fragment and remove pieces of the kidney stone 318 from the kidney 310(A).

In some embodiments, a position of a medical instrument can be represented with a point/point set and/or an orientation of the medical instrument can be represented as an angle/offset relative to an axis/plane. For example, a position of a medical instrument can be represented with a coordinate(s) of a point/point set within a coordinate system (e.g., one or more X, Y, Z coordinates) and/or an orientation of the medical instrument can be represented with an angle relative to an axis/plane for the coordinate system (e.g., angle with respect to the X-axis/plane, Y-axis/plane, and/or Z-axis/plane). Here, a change in orientation of the medical instrument can correspond to a change in an angle of the medical instrument relative to the axis/plane. Further, in some embodiments, an orientation of a medical instrument is represented with yaw, pitch, and/or roll information.

In some embodiments, a trajectory refers as a pose. For example, a trajectory of a medical instrument can refer to a pose of the medical instrument, including/indicating both a position and orientation of the medical instrument. Similarly, a target trajectory can refer to a target pose, including/indicating both a position and orientation of a desired path. However, in other embodiments, a trajectory refers to either an orientation or a position.

Although particular robotic arms of the robotic system 110 are illustrated as performing particular functions in the context of FIGS. 3-5, any of the robotic arms 112 can be used to perform the functions. Further, any additional robotic arms and/or systems can be used to perform the procedure. Moreover, the robotic system 110 can be used to perform other parts of the procedure. For example, the robotic system 110 can be controlled to align and/or insert the needle into the patient 130. To illustrate, one of the robotic arms 112 can engage with and/or control the needle 170 to position the needle 170 at the appropriate location, align the needle 170 with the target trajectory, and/or insert the needle 170 to the target location. The control system 140 can use localization techniques to perform such processing. As such, in some embodiments, a percutaneous procedure can be performed entirely or partially with the medical system 100 (e.g., with or without the assistance of the physician 160).

Example Instrument Visualizations

FIGS. 6-1 through 6-11 illustrate example interfaces to provide information regarding an alignment and/or a progress of a medical instrument during a procedure in accordance with one or more embodiments. The example interfaces are illustrated in the context of using the medical system 100 to remove a kidney stone 662 from the patient 130. In particular, visualizations can be provided to assist the physician 160 in inserting the needle 170 into the patient 130 to extract the kidney stone 662. However, the visualizations can be displayed for use with other medical systems and/or to perform other medical procedures. For ease of illustration, some features of the interfaces are not illustrated in each of FIGS. 6-1 through 6-11. For example, alignment markings 634(B) are not illustrated in FIGS. 6-2 through 6-11.

Figures 1, 6:
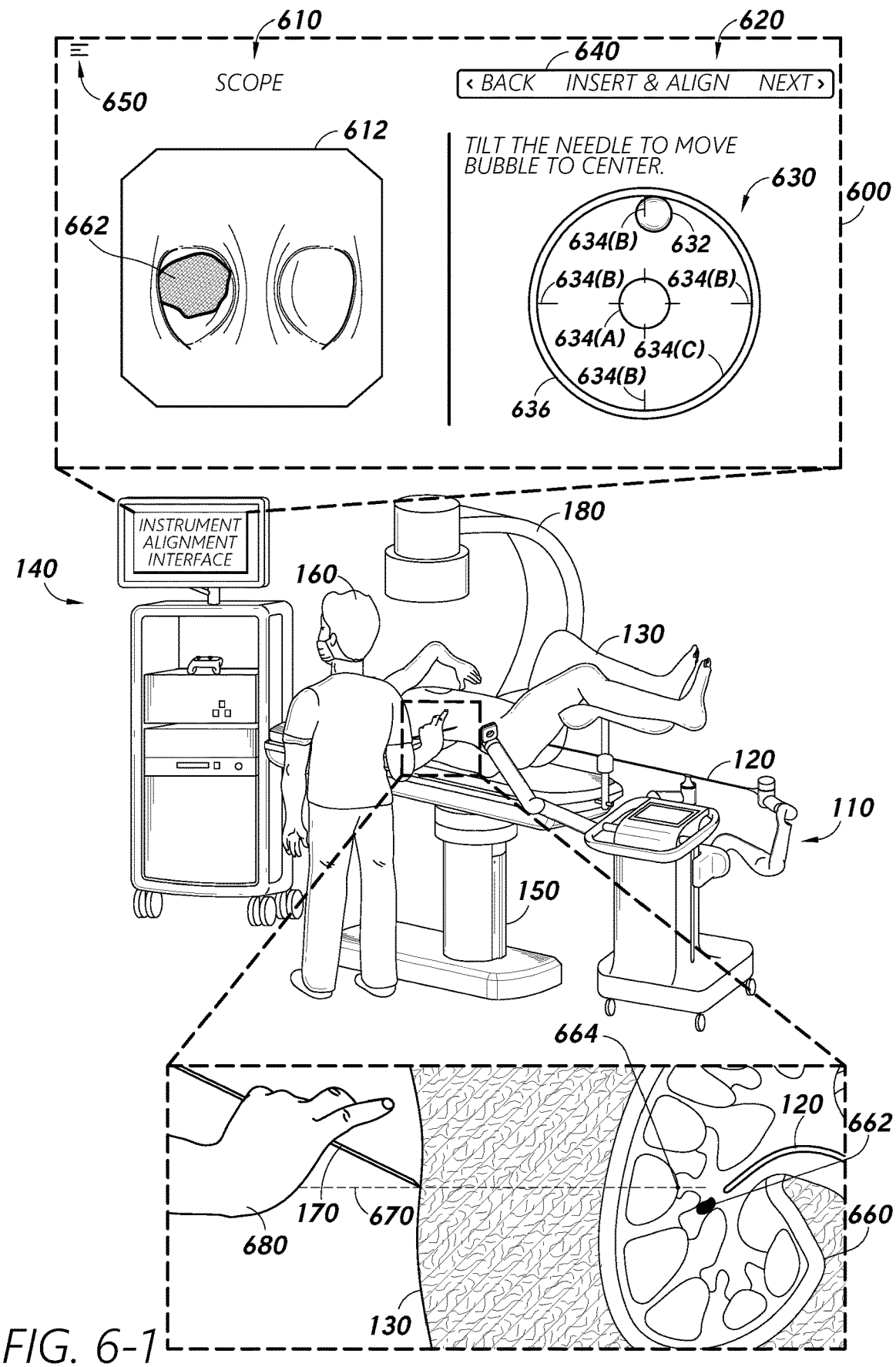
Figures 2, 6:
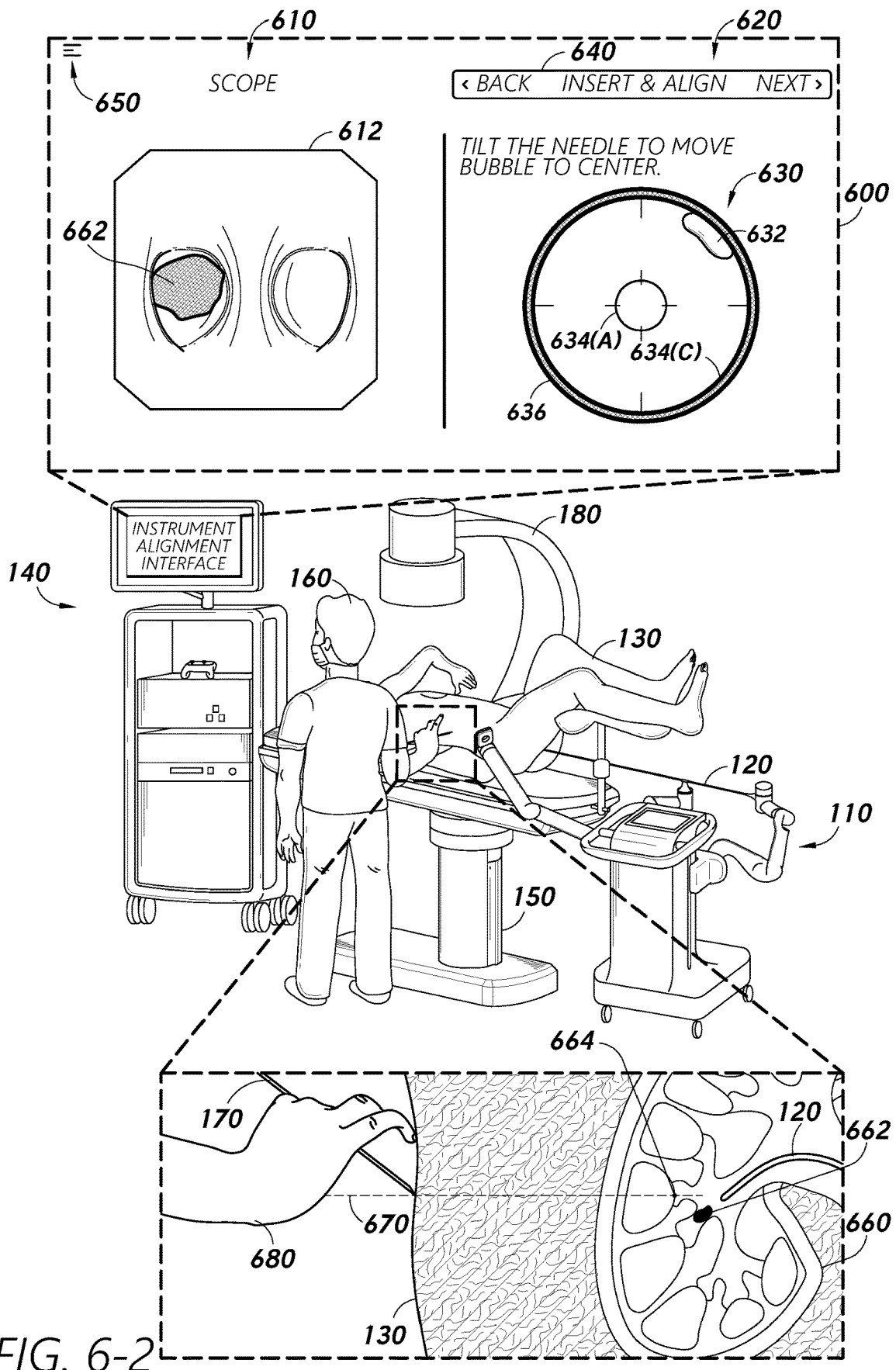
Figures 3, 6:
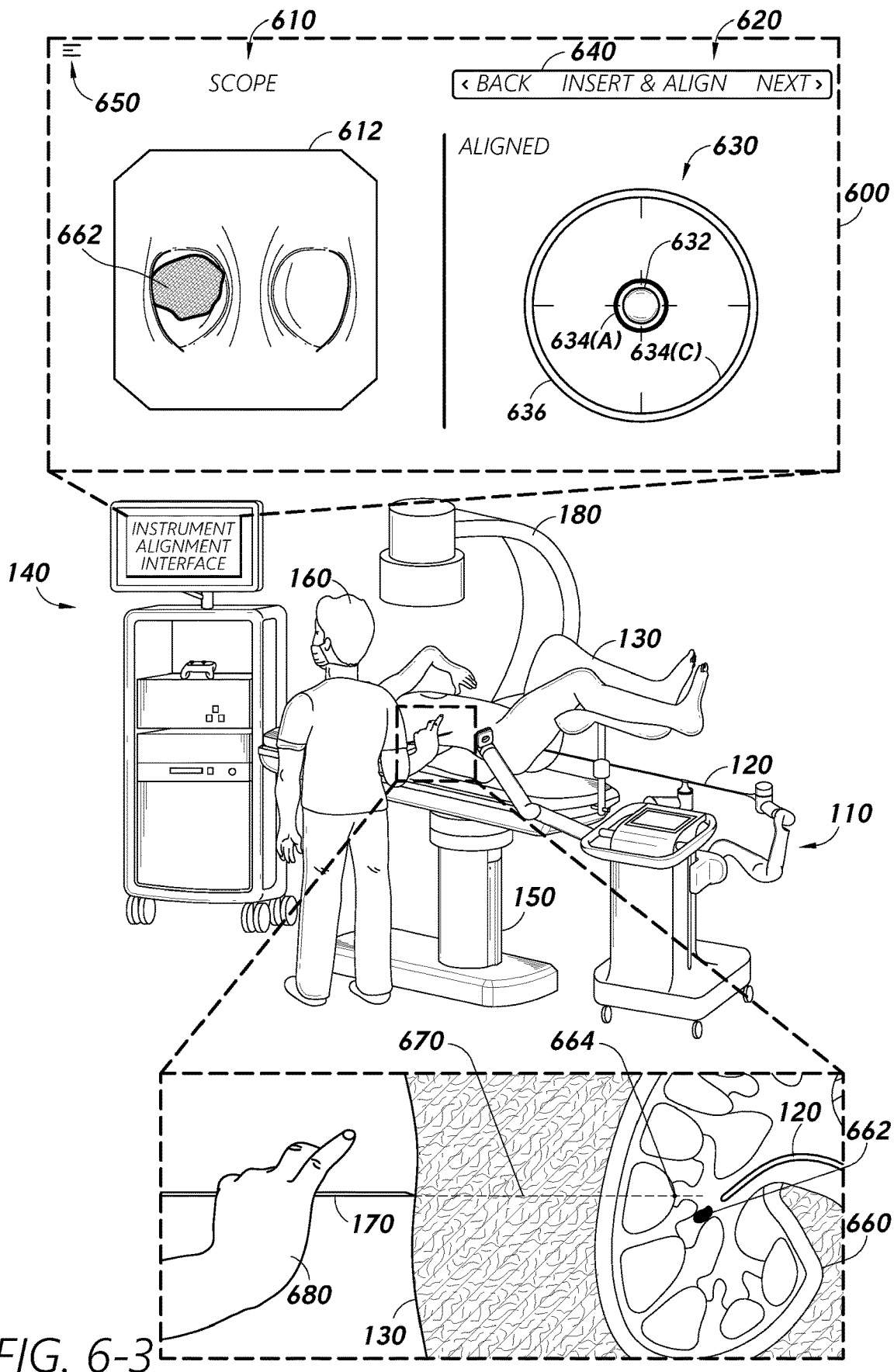
Figures 4, 6:
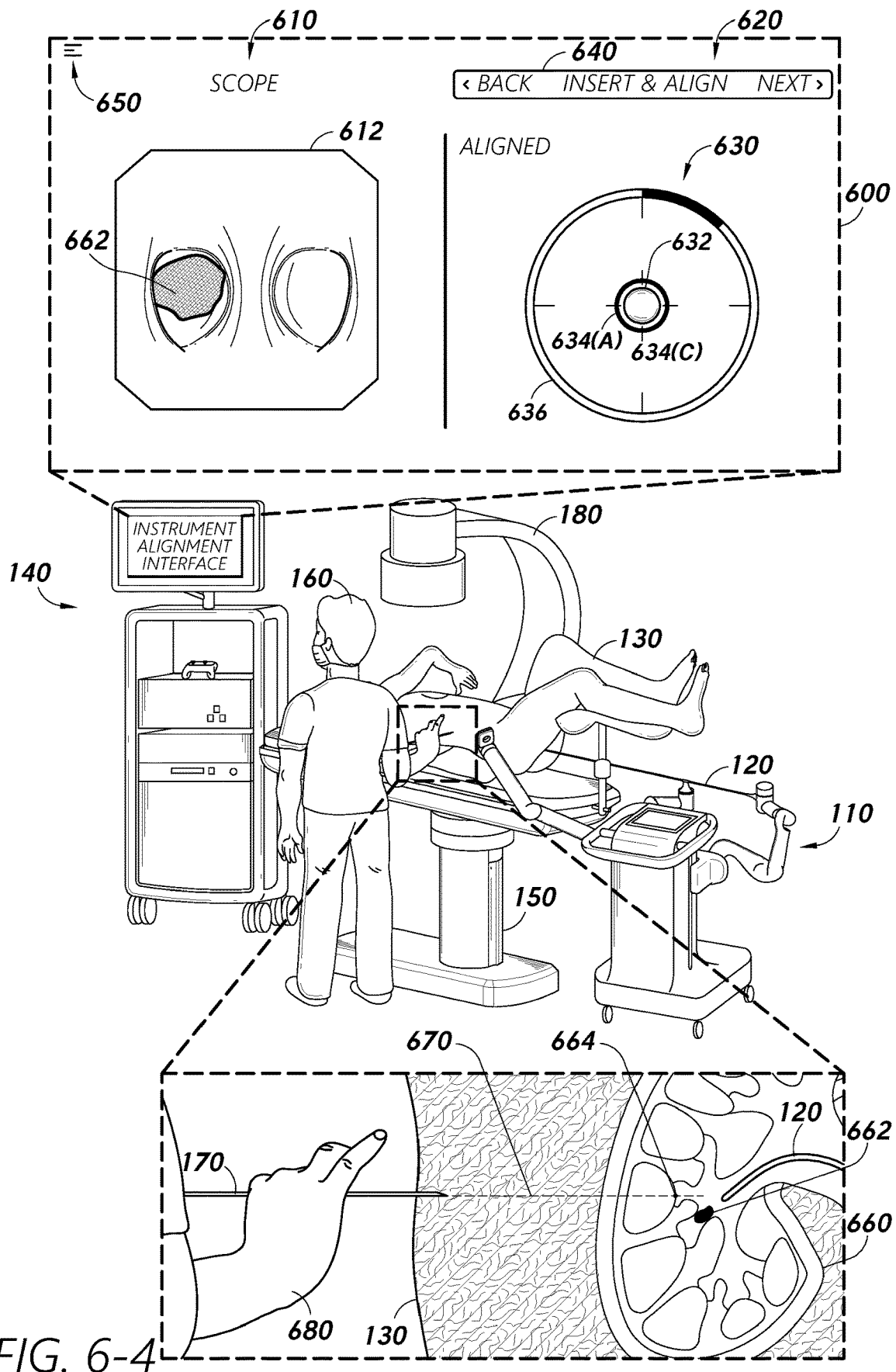
Figures 5, 6:
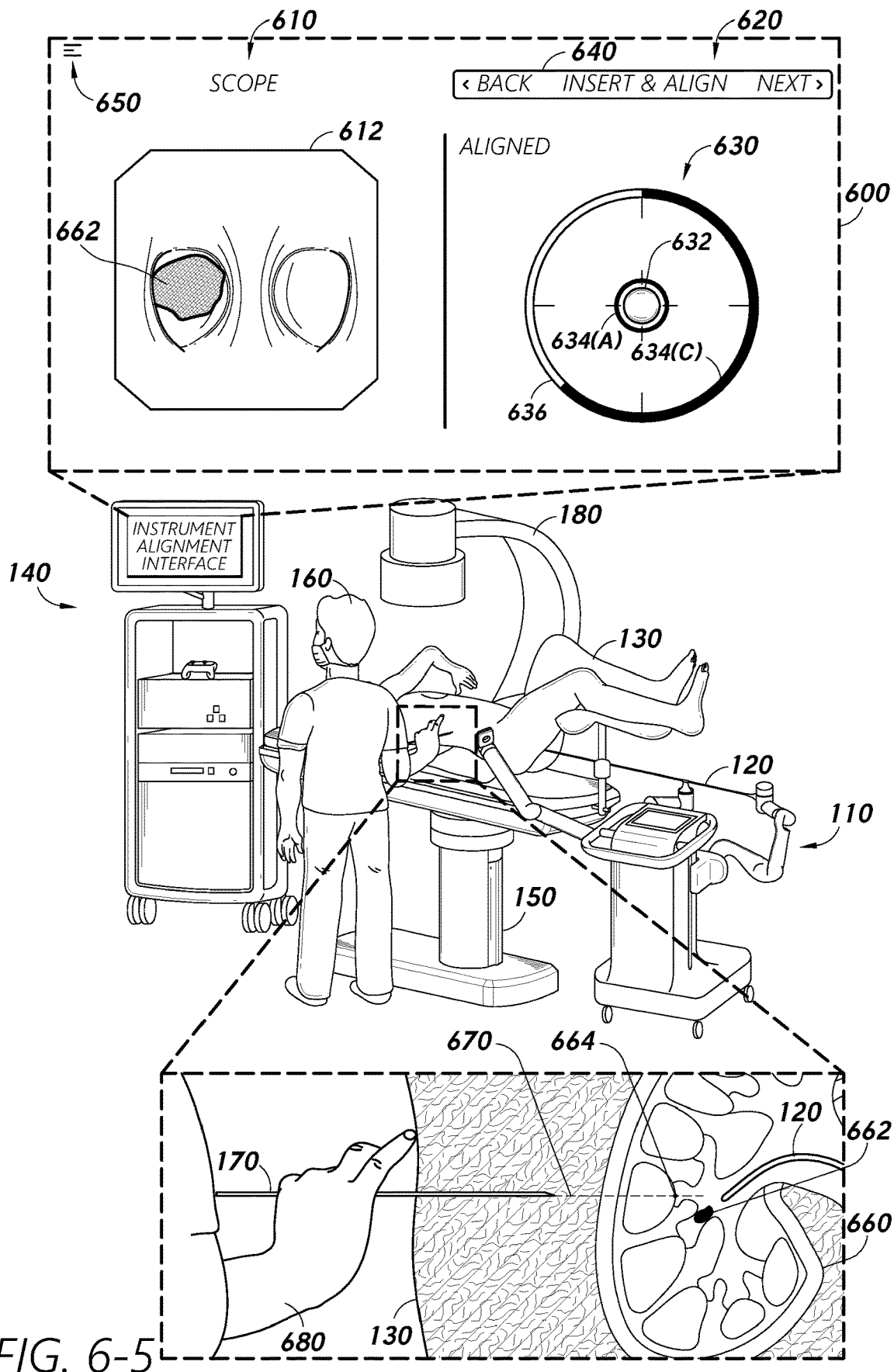
Figure 6:
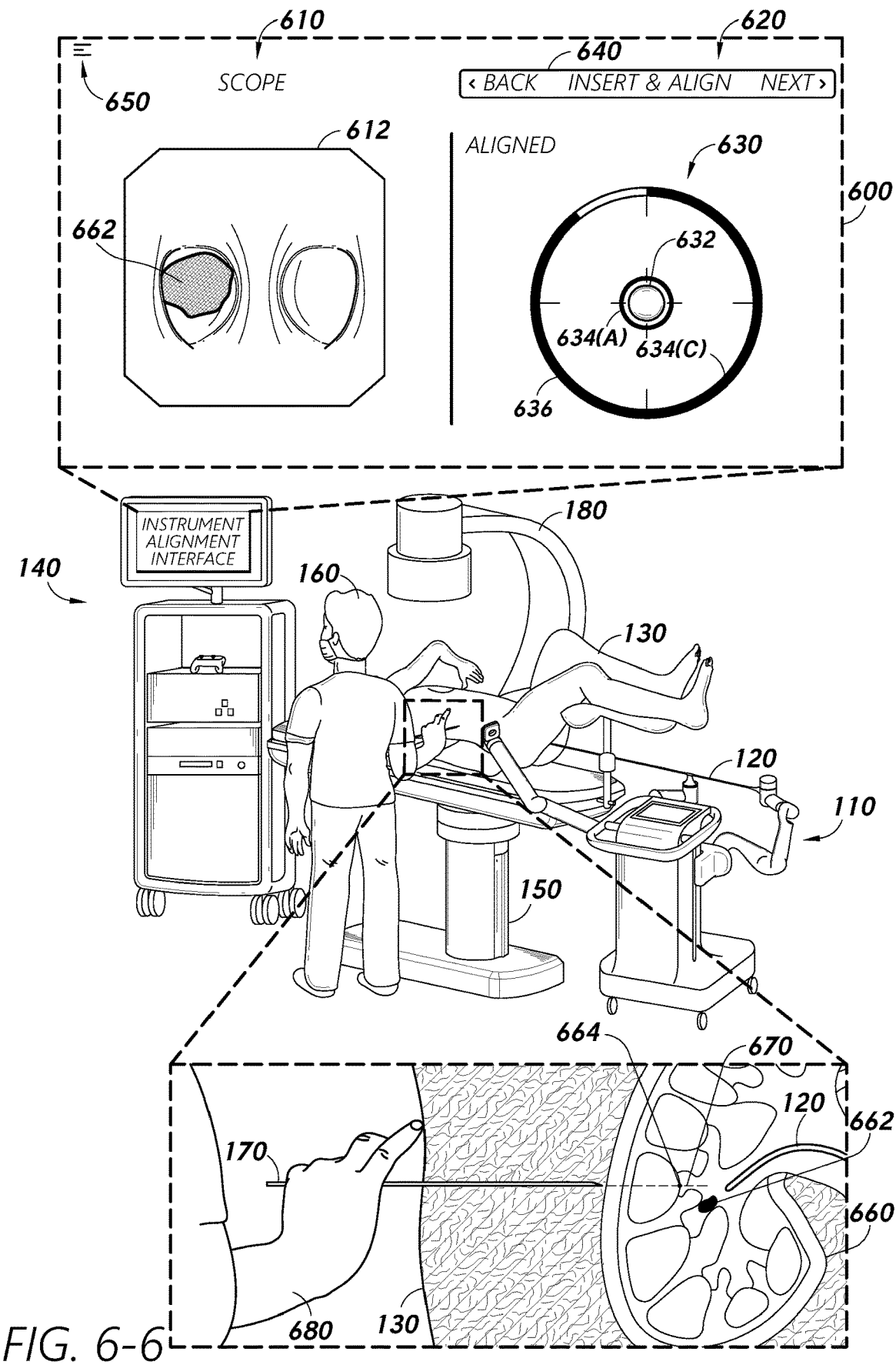

FIG. 6-1 illustrates the example instrument-alignment interface 600 with visualizations to assist the physician 160 in aligning the needle 170 with a target trajectory 670. As shown, the instrument-alignment interface 600 can include a scope section 610 to provide an image(s) 612 captured by the scope 120 that is located within a kidney 660 of the patient 130, and an alignment section 620 to provide information regarding an orientation and/or position of the needle 170. Here, the image(s) 612 depicts an internal portion of the kidney 660 and the kidney stone 662 located within the kidney 660. The alignment section 620 includes an alignment-progress visualization 630 to indicate an alignment of an orientation of the needle 170 to the target trajectory 670 and/or a proximity of the needle 170 to a target location 664 (e.g., a location on a papilla). As shown, the alignment-progress visualization 630 includes an instrument-alignment element 632 representing the orientation of the needle 170 relative to the target trajectory 670 and alignment markings 634 representing the target trajectory 670, and a progress bar 636 (also referred to as "the progress representation 636") indicating a proximity of the needle 170 to the target location 664. The instrument-alignment interface 600 can also include navigation representations 640 to navigate between different visualizations associated with different phases/steps of a procedure and/or a visual representation 650 to access a menu and/or other options. Although the instrument-alignment element 632 and the alignment markings 634 are illustrated with particular shapes and sizes, the instrument-alignment element 632 and the alignment markings 634 can have other shapes and/or sizes.

In the example of FIG. 6-1, the physician positions the needle 170 on the patient 130 and attempts to align the needle 170 with the target trajectory 670 using the instrument-alignment interface 600. In particular, the physician 160 can use one or more hands 680 to hold the needle 170 and adjust an orientation of the needle 170 (e.g., a tilt of the needle 170) while viewing the instrument-alignment interface 600 via the control system 140. Here, the orientation of the needle 170 is out of alignment with the target trajectory 670. As such, the instrument-alignment interface 600 illustrates the instrument-alignment element 632 as being out of alignment with the center alignment marking 634(A) (e.g., the instrument-alignment element 632 is not located within the center alignment marking 634(A)).

In some embodiments, the instrument-alignment element 632 can move within the area of the boundary alignment marking 634(C) (e.g., within the constraints of the boundary alignment marking 634(C)). The instrument alignment element 632 can move closer to the boundary alignment marking 634(C) as the needle 170 is less aligned with the target trajectory 670 and move closer to the center alignment marking 634(A) as the needle 170 is more aligned with the target trajectory 670. In the example of FIG. 6-1, the instrument-alignment interface 600 also provides text "Tilt the needle to move bubble to center" indicating that the needle 170 is out of alignment with the target trajectory 670. The visualizations of the instrument-alignment interface 600 can assist the physician 160 in tilting the needle 170 to align the needle 170 with the appropriate orientation for insertion of the needle 170 to the target location 664.

In some embodiments, if the needle 170 is substantially out of alignment with the target trajectory 670, the instrument-alignment element 632 can provide an indication of such out-of-alignment configuration, as shown in FIG. 6-2. For example, if the needle 170 is out of alignment with the target trajectory 670 by more than a threshold amount (e.g., misalignment threshold), the progress bar 636 can be highlighted, outlined, and/or partially/completely filled-in with a particular color/fill pattern to provide such out-of-alignment indication, as shown. To illustrate, the progress bar 636 can be filled-in with a red color (e.g., a closed red ring). Additionally or alternatively, in some embodiments, the instrument-alignment element 632 can be displayed in contact with the boundary marking 634(C) with a deformed shape, as also shown in FIG. 6-2. Here, the instrument-alignment element 632 can be displayed in its initial circular form as the instrument-alignment element 632 moves within proximity to the boundary marking 634(C) and transition to the deformed shape as the needle 170 moves more out of alignment and beyond the misalignment threshold. Such transition visualization can appear similar to an air bubble within a liquid that comes into contact with a surface. Further, in some embodiments, text or another indication can be provided within the instrument-alignment interface 600 to indicate that the needle 170 is out of alignment with the target trajectory by more than the threshold amount. In any case, such out-of-alignment indication can assist the physician 160 in viewing that the needle 170 is substantially off axis with the target trajectory 670. Although the progress bar 636 is illustrated with particular highlighting, outlining, and/or a fill pattern to provide the substantially out-of-alignment indication in FIG. 6-2, in some embodiments the progress bar 636 can be implemented without such changes. Here, the instrument-alignment element 632 can be displayed with a deformed shape to provide the substantially out-of-alignment indication.

When the needle 170 is aligned with the target trajectory 670, the instrument-alignment element 632 can be displayed in an aligned manner with the alignment markings 634, as shown in FIG. 6-3. For example, the instrument-alignment element 632 can be displayed within and/or concentric with the center alignment marking 634(A). Additionally or alternatively, the center alignment marking 634(A) can be highlighted (e.g., with a glow visualization, particular color, etc.) to indicate that the needle 170 is aligned with the target trajectory 670. Further, the instrument-alignment interface 600 can display text to indicate the alignment, such as text "Aligned," as shown in FIG. 6-3. Although the highlighted alignment marking 634(A) and the text are presented in FIG. 6-3, in some embodiments just one of such visualizations is presented. Further, other visualizations can be used to indicate such alignment.

In in this example, the physician 160 inserts the needle 170 when the needle 170 is aligned with the target trajectory 670, as shown in FIGS. 6-4 through 6-6. Here, the progress bar 636 provides an indication of the proximity (e.g., a distance) of the needle 170 relative to the target location 664. In particular, the progress bar 636 can fill-in in a clockwise manner around the boundary marking 634(C). The control system 140 can determine the proximity of the needle 170 to the target location 664 by using localization techniques to track a position of the needle 170 and/or a position of the target location 664/the scope 120.

In some embodiments, as the needle 170 moves closer to the target location 664, an amount of movement of the instrument-alignment element 632 can change (e.g., a sensitivity of the instrument-alignment element 632 can change). For example, the control system 140 can set a position change parameter for the instrument-alignment element 632 to a first value initially when the needle 170 is relatively far from the target location 664 (e.g., outside a distance to the target location 664). The position change parameter can be indicative of an amount of position change of the instrument-alignment element 632 with respect to a unit of movement of the needle 170. As the needle 170 moves closer to the target location 664, the position change parameter can be updated to a second value, such as a value that is associated with a greater or lesser amount of position change for the same unit of movement of the needle 170 than the first value.

In one illustration of updating a position change parameter, when the needle 170 is located on the skin of the patient 130, the position change parameter can be set to an initial value. The initial value can cause the instrument-alignment element 632 to move by a first number of pixels in response to an orientation change of the needle 170 by 5 degrees, for example. As the needle 170 moves closer to the target location 664, the position change parameter can be updated to a larger value that causes the instrument-alignment element 632 to move by a second number of pixels in response to an orientation change of the needle 170 by 5 degrees, where the second number of pixels is greater than the first number of pixels. The position change parameter can be updated any number of times as the needle 170 moves closer to the target location 664. In some embodiments, this can assist the physician in aligning the needle 170 to reach a relatively small target, such as a calyx that can be 4 to 8 mm in diameter.

Figures 6, 7:
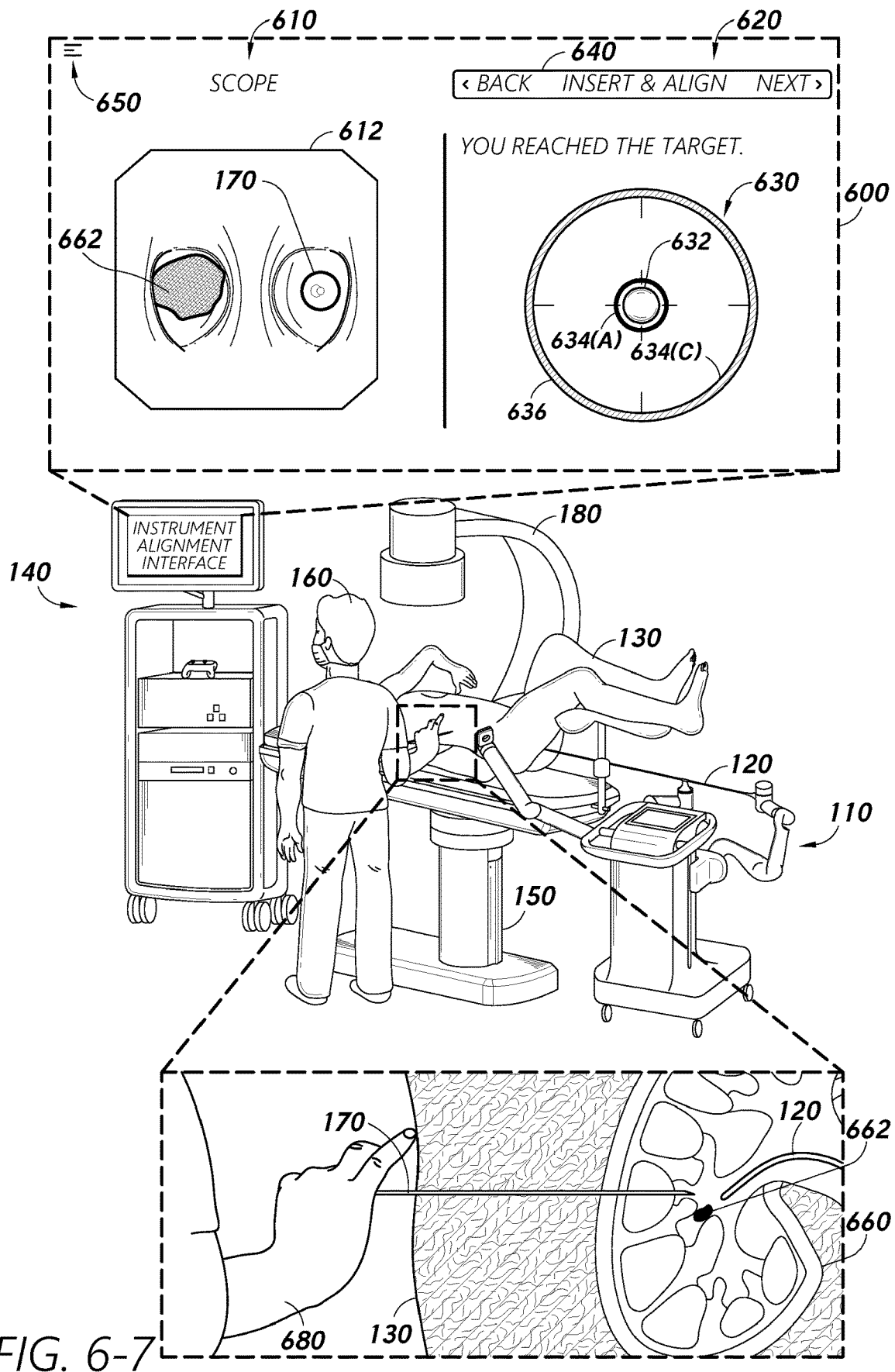

When the needle 170 has reached the target location 664, the instrument-alignment interface 600 can display an indication that the target location 664 has been reached, as illustrated in FIG. 6-7. For example, the progress bar 636 can fill-in completely around the perimeter of the boundary marking 634(C). In some embodiments, the progress bar 636 can be highlighted, outlined, and/or completely filled-in with a particular color/fill pattern to indicate that the target location 664 has been reached. For example, the progress bar 636 can be filled-in with a green color (e.g., a closed green ring). Additionally or alternatively, the instrument-alignment interface 600 can provide text that the target location 664 has been reached, such as providing the text "You reached the target," as also shown. In some embodiments, as shown in FIG. 6-7, the image 612 depicting the interior portion of the kidney 660 can also provide a visual confirmation that the needle 170 has reached the target location 664.

Figures 6, 7, 8:
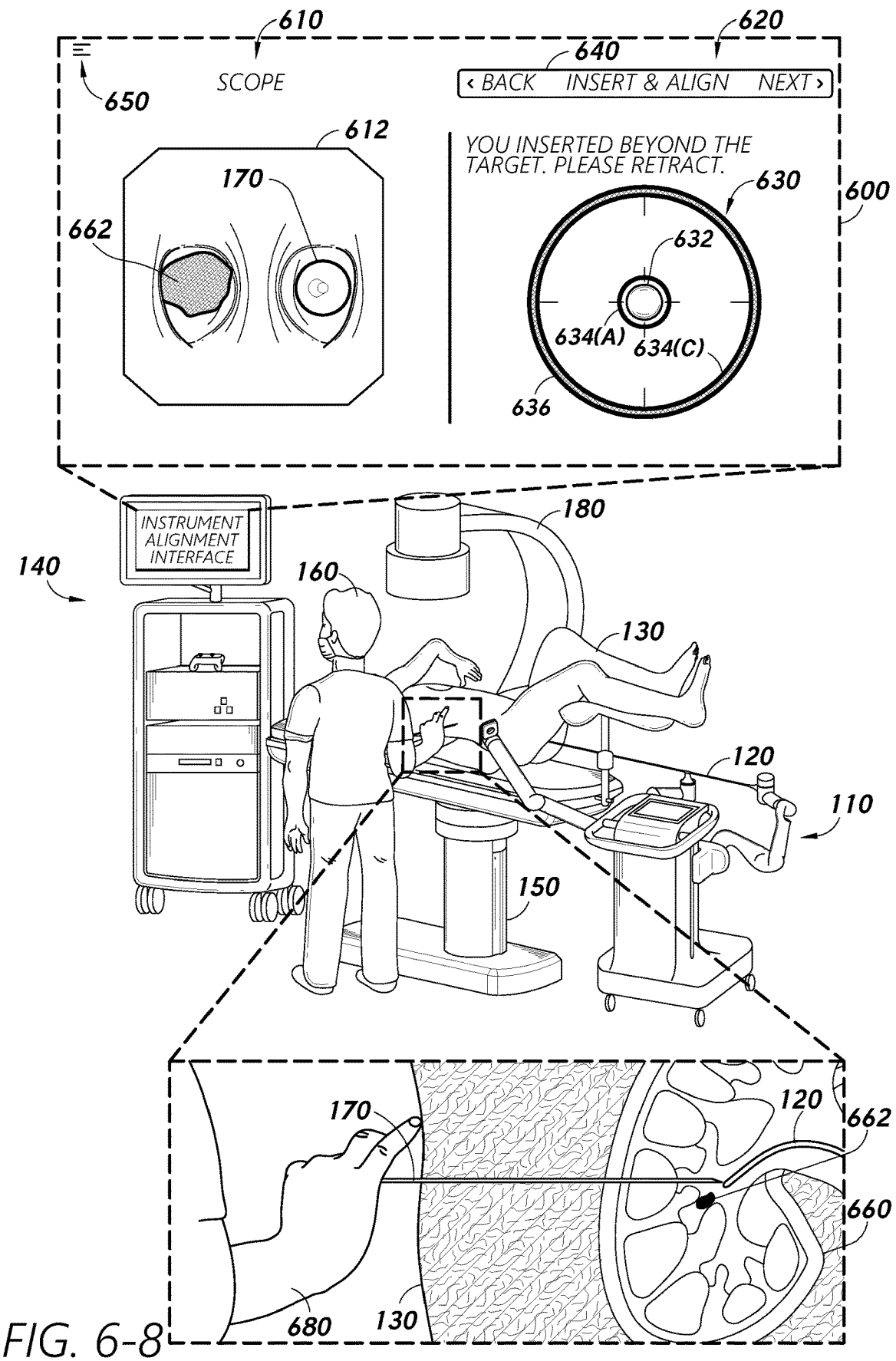

In some implementations, if the needle 170 is inserted beyond the target location 664, the instrument-alignment interface 600 can provide an indication that the needle 170 is inserted beyond the target location 664, as shown in FIG. 6-8. For example, the progress bar 636 can be highlighted, outlined, and/or partially/completely filled-in with a particular color/fill pattern to indicate that the needle 170 is inserted beyond the target location 664. To illustrate, the progress bar 636 can be filled-in with a red color (e.g., a closed red ring) and/or a different color than in the case of the needle 170 being substantially out of alignment (e.g., the case of FIG. 6-2). Additionally or alternatively, the instrument-alignment interface 600 can provide text that the needle 170 is inserted beyond the target location 664, such as providing the text "You inserted beyond the target. Please retract." In some embodiments, the control system 140 can determine that the needle 170 is inserted beyond the target location 664 when the needle 170 is more than a threshold distance beyond the target location 664 and/or when the needle 170 is within a particular distance to the scope 120.

In some embodiments, as shown in FIG. 6-8, the image 612 depicting the interior portion of the kidney 660 can also provide a visual confirmation that the needle 170 has been inserted beyond the target location 664. In other embodiments, a field-of-view of the scope 120 may not include a location where the needle 170 enters the kidney 660 (e.g., the needle 170 can be inserted above or below a field-of-view of the scope 120). Here, the progress bar 636 can be particularly helpful in informing the physician 160 that the needle 170 is inserted beyond the target location 664.

In some procedures, once the needle 170 has reached the target location 664, a medical instrument 638 can be inserted over the needle 170 and/or in the place of the needle 170, as shown in FIG. 6-9. The medical instrument 638 can include a device to assist in extracting the kidney stone 662 from the kidney 660. For example, the medical instrument 638 can include a catheter (e.g., a power catheter), a vacuum tube, a nephroscope, or any other medical instrument. In some embodiments, one or more dilation instruments (e.g., wires, tubes, sheaths, etc.) can be used to dilate a path to the target location 664 to provide sufficient space for insertion of the medical instrument 638.

The medical instrument 638 and/or the scope 120 (and/or the needle 170, in some cases) can facilitate extraction of the kidney stone 662 from the kidney 660. For example, the scope 120 can deploy a tool (e.g., a laser, a cutting instrument, etc.) to fragment the kidney stone 662 into pieces and the medical instrument 638 can suck out the pieces from the kidney 660, as shown in FIG. 6-10. In some implementations, the scope 120 (and/or the medical instrument 638) can provide irrigation to assist in removing the pieces from the kidney 660. In the example of FIG. 6-10, the image 612 provides visual confirmation that the kidney stone 662 is being removed from the kidney 660.

In some embodiments, in returning to alignment of the needle 170 on the skin of the patient 130 (e.g., FIG. 6-2), if the needle 170 is inserted when it is substantially out of alignment with the target trajectory 670, the instrument-alignment interface 600 can provide an indication to retract the needle 170, as shown in FIG. 6-11. For example, the control system 140 can determine that the needle is out of alignment with the target trajectory 670 by more than a threshold amount (similar to that discussed in reference to FIG. 6-2). Further, the control system 140 can determine that the needle 170 is inserted into the patient 130 beyond a particular distance when the needle 170 is substantially out of alignment with the target trajectory 670. In some embodiments, the progress bar 636 can be highlighted, outlined, and/or partially/completely filled-in with a particular color/fill pattern to indicate that the needle 170 is inserted and is substantially out of alignment. To illustrate, the progress bar 636 can be filled-in with a red color (e.g., a closed red ring) and/or a different color than the case of the needle 170 just being substantially out of alignment (e.g., the case of FIG. 6-2). Additionally or alternatively, in some embodiments, the instrument-alignment interface 600 can provide text that the needle 170 is substantially out of alignment and needs to be retracted, such as providing the text "Retract and reinsert the needle with the appropriate orientation." In some embodiments, the indication of FIG. 6-11 can be presented when it is determined that there is no adjustment that can be made to the needle 170 to reach the target location 664.

Although alignment and progress information are illustrated with specific indications in FIGS. 6-1 through 6-11, other indications can be provided including audible, visual, haptic, etc. For example, the control system 140 can provide sounds and/or haptic feedback via an I/O device associated with the control system 140 to indicate alignment and/or progress of the needle 170 (e.g., a first sound when the needle 170 is aligned with the target trajectory 670, a second sound when the needle 170 is initially inserted, a third sound when the needle 170 is halfway to the target trajectory 664, a third sound when the needle 170 has reached the target location 664, etc.). Further, any of the indications discussed can be illustrated in different forms (e.g., different shapes, sizes, colors, and so on) and/or presented at different locations within the instrument-alignment interface 600.

In some implementations, the progress bar 636 can include a straight progress bar, instead of the circular bar illustrated around the boundary marking 634, which can be positioned at any location within the instrument-alignment interface 600. Further, in some embodiments, instead of filling in the progress bar 636 to indicate a proximity of the needle 170 to the target location 664, a current position of the needle 170 can be displayed on the progress bar 636 with an icon (e.g., with the icon at a top position indicating that the needle 170 is not yet inserted into the patient 130 and/or has reached the target location 664). Moreover, in some embodiments, a percentage of progress to the target location 664 can be presented via the instrument-alignment interface 600.

Furthermore, in some embodiments, a size of the center alignment marking 634(A), the boundary marking 634(C), and/or the instrument-alignment element 632 can change to indicate a progress of inserting the needle 170 to the target location 664. For example, a diameter of the center alignment marking 634(A) can decrease as the needle 170 is inserted until the center alignment marking 634(A) reaches the same diameter as the instrument-alignment element 632.

Example Flow Diagrams

FIGS. 7-10 illustrate example flow diagrams of processes for performing one or more techniques discussed herein. The various operations associated with the processes can be performed by control circuitry implemented in any of the devices/systems discussed herein, or a combination thereof, such as the control system 140, the robotic system 110, the table 150, the EM field generator 180, the scope 120, and/or the needle 170.

FIG. 7 illustrates an example flow diagram of a process 700 for determining an alignment of a medical instrument relative to a target trajectory and presenting information regarding the alignment of the medical instrument to the target trajectory in accordance with one or more embodiments. At block 702, the process 700 can include receiving sensor data from one or more medical instruments. For example, according to certain use cases, control circuitry of a device/system, such as a control system, can receive sensor data via a communication interface from one or more medical instruments, such as a scope, a needle, or any other medical instrument. The sensor data can be indicative of a position and/or an orientation of the one or more medical instruments.

At block 704, the process 700 can include determining a target location within human anatomy. For example, according to certain use cases, control circuitry can determine a target location within a patient, such as an anatomical landmark, a location of a medical instrument, or any other location/target. In some embodiments, the control circuitry can determine the target location based at least in part on sensor data from a medical instrument that is disposed at least partially within the patient.

At block 706, the process 700 can include determining a position and/or an orientation of the one or more medical instruments. For example, according to certain use cases, control circuitry can determine a position and/or an orientation of one or more medical instruments based at least in part on sensor data from the one or more medical instruments. In some embodiments, the control circuitry can use one or more localization techniques to determine the position and/or the orientation of the one or more medical instruments.

At block 708, the process 700 can include determining a target trajectory for accessing the target location. For example, according to certain use cases, control circuitry can determine a target trajectory for accessing a target location within a patient percutaneously. In some embodiments, the control circuitry can determine the target trajectory based at least in part on sensor data from a medical instrument that is disposed at least partially within the patient, sensor data from a medical instrument that is located externally to the patient (or partially inserted), a position of the target location, and so on. Additionally or alternatively, a target trajectory can be determined based on a user providing input through an interface to designate a target trajectory. In examples, a target trajectory can be defined with respect to one or more anatomical planes/axes.

At block 710, the process 700 can include generating user interface data representing an interface that includes an instrument-alignment element indicative of an alignment of an orientation of a medical instrument to the target trajectory. For example, according to certain use cases, control circuitry can generate user interface data representing an interface (e.g., an instrument-alignment interface) that includes an instrument-alignment element representing an orientation of a medical instrument, such as a needle-alignment icon representing an orientation of a needle. In some embodiments, a positioning of the instrument-alignment element within the interface can indicate an alignment of the orientation of the medical instrument to a target trajectory.

At block 712, the process 700 can include causing display of the interface. For example, according to certain use cases, control circuitry can cause display of an interface via a display device, such as by sending user interface data to a display device associated with a control system. Further, according to certain use cases, a display device can display of an interface based at least in part on user interface data. In any case, the interface can include an instrument-alignment element representing an orientation of a medical instrument.

At block 714, the process 700 can include updating a position of the instrument-alignment element based at least in part on a change in the orientation of the medical instrument. For example, according to certain use cases, control circuitry can determine a change to an orientation of a medical instrument and update a position of an instrument-alignment element that is associated with the medical instrument based at least in part on the change in orientation of the medical instrument.

In some embodiments of block 714, control circuitry can update the position of an instrument-alignment element based at least in part on a proximity of a medical instrument to a target location. For example, in response to determining that the orientation of the medical instrument has changed by a unit of measurement and determining that the medical instrument is outside a predetermined proximity to the target location, the control circuitry can update a position of the instrument-alignment element within an interface by a first amount. Further, in response to determining that the orientation of the medical instrument has changed by the unit of measurement and determining that the medical instrument is within the predetermined proximity to the target location, the control circuitry can update the position of the instrument-alignment element within the interface by a second amount.

FIG. 8 illustrates an example flow diagram of a process 800 for presenting information regarding an orientation of a medical instrument in accordance with one or more embodiments. At block 802, the process 800 can include determining an orientation of a medical instrument. For example, according to certain use cases, control circuitry can determine an orientation of a medical instrument that is configured to access a human anatomy percutaneously based at least in part on sensor data from the medical instrument. In some embodiments, the control circuitry can use one or more localization techniques to determine the orientation of the medical instrument.

At block 804, the process 800 can include determining if the orientation of the medical instrument is aligned with a target trajectory. For example, according to certain use cases, control circuitry can determine, based at least in part on sensor data of a medical instrument, whether or not an orientation of the medical instrument is aligned with a target trajectory that is determined for accessing a target location percutaneously. In some embodiments, the control circuitry can compare one or more coordinates and/or angles of the orientation of the medical instrument with one or more coordinates and/or angles of the target trajectory and determine if one or more thresholds are satisfied (e.g., the one or more coordinates and/or angles of the orientation of the medical instrument are within a particular number of coordinates and/or degrees to the one or more coordinates and/or angles of the target trajectory). In examples, alignment can be determined with respect to positional error and/or angular error (e.g., X, Y, Z, yaw, pitch, roll) and/or with respect to any coordinate frame.

If it is determined that the orientation of the medical instrument is aligned with the target trajectory, the process 800 can proceed to block 806. In contrast, if it is determined that the orientation of the medical instrument is not aligned with the target trajectory, the process 800 can proceed to block 808.

At block 806, the process 800 can include causing display of an indication that the orientation of the medical instrument is aligned with the target trajectory. For example, according to certain use cases, control circuitry can cause display of an indication, within an interface, that an orientation of a medical instrument is aligned with a target trajectory, such as by sending data to a display device associated with a control system. Further, according to certain use cases, a display device can display, within an interface, an indication that an orientation of a medical instrument is aligned with a target trajectory. In some embodiments, an instrument-alignment element is displayed in an aligned arrangement with one or more alignment markings (e.g., centered on a marking) to indicate that the orientation of the medical instrument is aligned with the target trajectory.

At block 808, the process 800 can include determining if the orientation of the medical instrument is out of alignment with the target trajectory by more than a threshold amount. For example, according to certain use cases, control circuitry can determine, based at least in part on sensor data of a medical instrument, whether or not the orientation of the medical instrument is out of alignment with a target trajectory by more than a threshold amount. In some embodiments, the control circuitry can compare one or more coordinates and/or angles of the orientation of the medical instrument with one or more coordinates and/or angles of the target trajectory.

If it is determined that the orientation of the medical instrument out of alignment with the target trajectory by more than the threshold amount, the process 800 can proceed to block 810. In contrast, if it is determined that the orientation of the medical instrument not out of alignment with the target trajectory by more than the threshold amount, the process 800 can proceed to block 812.

At block 810, the process 800 can include causing display of an instrument-alignment element at a boundary marking and/or with a deformed form. For example, according to certain use cases, control circuitry can cause display of an instrument-alignment element within a predetermined proximity to a boundary marking and/or with a deformed shape, such as by sending data to a display device associated with a control system. Further, according to certain use cases, a display device can display, within an interface, an instrument-alignment element within a predetermined proximity to a boundary marking and/or with a deformed shape.

At block 812, the process 800 can include causing display of an instrument-alignment element with a position that is out of alignment. For example, according to certain use cases, control circuitry can cause display of an instrument-alignment element at a location that is not aligned with an alignment marking, such as by sending data to a display device associated with a control system. Further, according to certain use cases, a display device can display an instrument-alignment element at a location that is not aligned with an alignment marking.

At block 814, the process 800 can include determining if the medical instrument is inserted into the human anatomy. For example, according to certain use cases, control circuitry can determine whether or not a medical instrument is disposed at least partially within a patient based at least in part on sensor data from the medical instrument and/or information regarding a position and/or orientation of the patient. In some embodiments, the control circuitry can determine whether or not the medical instrument is inserted into the patient by a particular amount.

If it is determined that the medical instrument is inserted into the human anatomy, the process 800 can proceed to block 816. In contrast, if it is determined that the medical instrument is not inserted into the human anatomy, the process 800 can proceed to block 818.

At block 816, the process 800 can include causing display of an indication to retract the medical instrument. For example, according to certain use cases, control circuitry can cause display of an indication to retract a medical instrument, such as by sending data to a display device associated with a control system. Further, according to certain use cases, a display device can display an indication to retract a medical instrument. In some embodiments, control circuitry can maintain display of information associated with blocks 810 and/or 812 (e.g., instrument-alignment elements), as well as provide the indication to retract the medical instrument.

At block 818, the process 800 can include maintaining display of information. For example, according to certain use cases, control circuitry can maintain display of text or other visualizations regarding a current orientation and/or position of a medical instrument (e.g., information presented at blocks 810 and/or 812). Although block 818 is illustrated, in some embodiments, another operation or process can be performed.

Figures 6, 7, 8, 9:
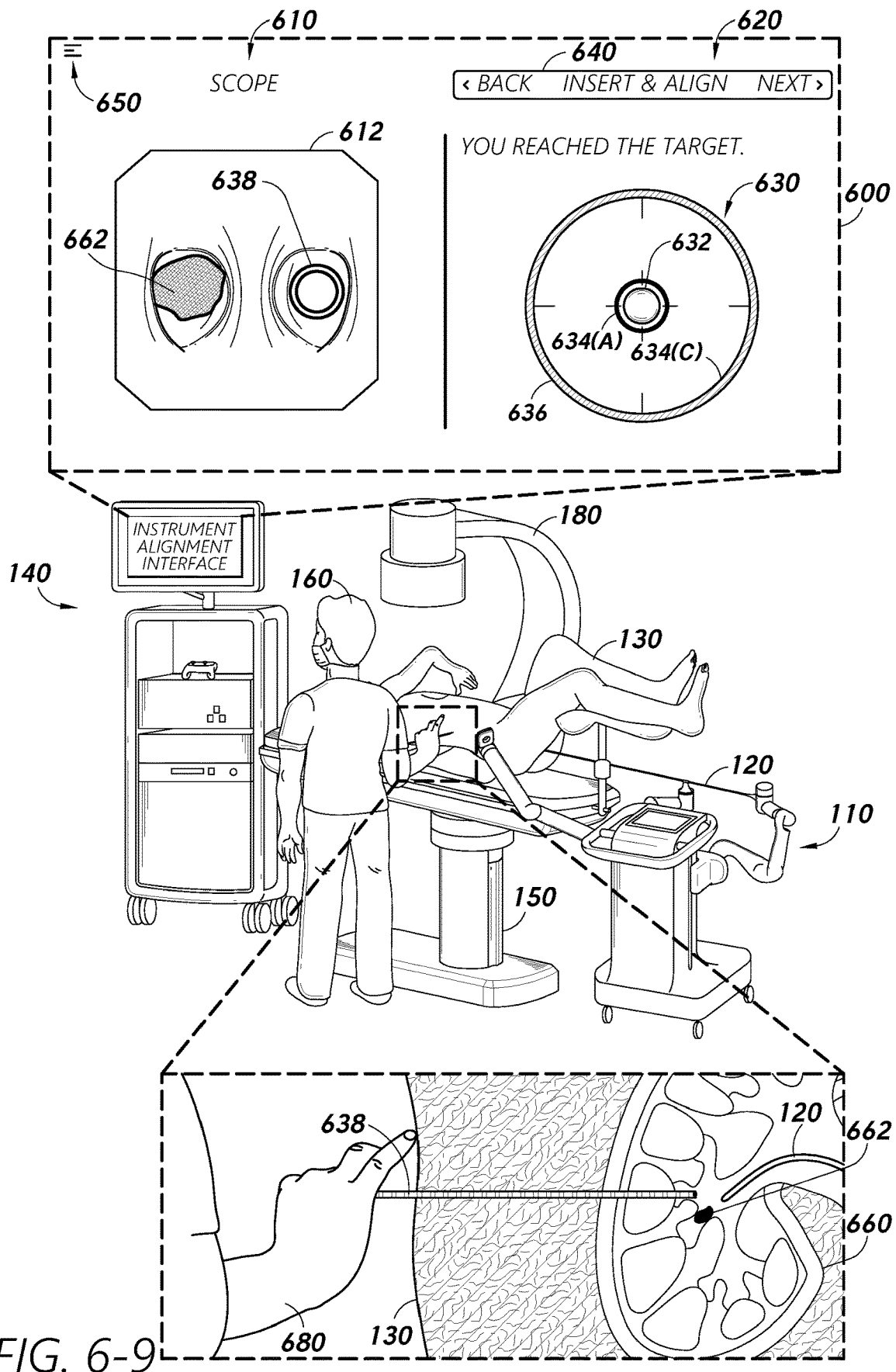

FIG. 9 illustrates an example flow diagram of a process 900 for presenting information regarding a proximity of a medical instrument to a target location in accordance with one or more embodiments. At block 902, the process 900 can include determining a proximity of a medical instrument to a target location. For example, according to certain use cases, control circuitry can determine a proximity of a medical instrument to a target location within a patient based at least in part on sensor data from the medical instrument. In some embodiments, the control circuitry can use one or more localization techniques to determine the position of the medical instrument.

At block 904, the process 900 can include causing display of an indication of the proximity of the medical instrument to the target location. For example, according to certain use cases, control circuitry can cause display of an indication, within an interface, of a proximity of a medical instrument to a target location, such as by sending data to a display device associated with a control system. Further, according to certain use cases, a display device can display an indication, within an interface, of a proximity of a medical instrument to a target location.

At block 906, the process 900 can include determining if the medical instrument has reached the target location. For example, according to certain use cases, control circuitry can determine whether or not a medical instrument has reached a target location within a patient based at least in part on sensor data from the medical instrument.

If it is determined that the medical instrument has reached the target location, the process 900 can proceed to block 908. In contrast, if it is determined that the medical instrument as not reached the target location, the process 900 can proceed back to block 902.

At block 908, the process 900 can include causing display of an indication of that the medical instrument has reached the target location. For example, according to certain use cases, control circuitry can cause display of an indication, within an interface, that a medical instrument has reached a target location, such as by sending data to a display device associated with a control system. Further, according to certain use cases, a display device can display an indication, within an interface, that a medical instrument has reached a target location.

At block 910, the process 900 can include determining if the medical instrument is inserted beyond the target location. For example, according to certain use cases, control circuitry can determine, whether or not a medical instrument is inserted beyond the target location based at least in part on sensor data from the medical instrument.

If it is determined that the medical instrument is inserted beyond the target location, the process 900 can proceed to block 912. In contrast, if it is determined that the medical instrument is not inserted beyond the target location, the process 900 can proceed back to block 902. Although the process 900 is illustrated as proceeding back to block 902 in the example of FIG. 9, in some embodiments, the process 900 can proceed back to block 906, block 908, or another block.

At block 912, the process 900 can include causing display of an indication of that the medical instrument is inserted beyond the target location. For example, according to certain use cases, control circuitry can cause display of an indication, within an interface, that a medical instrument is inserted beyond the target location, such as by sending data to a display device associated with a control system. Further, according to certain use cases, a display device can display an indication, within an interface, that a medical instrument is inserted beyond the target location. The process 900 can then proceed back to block 902.

Figures 6, 7, 8, 9, 10:
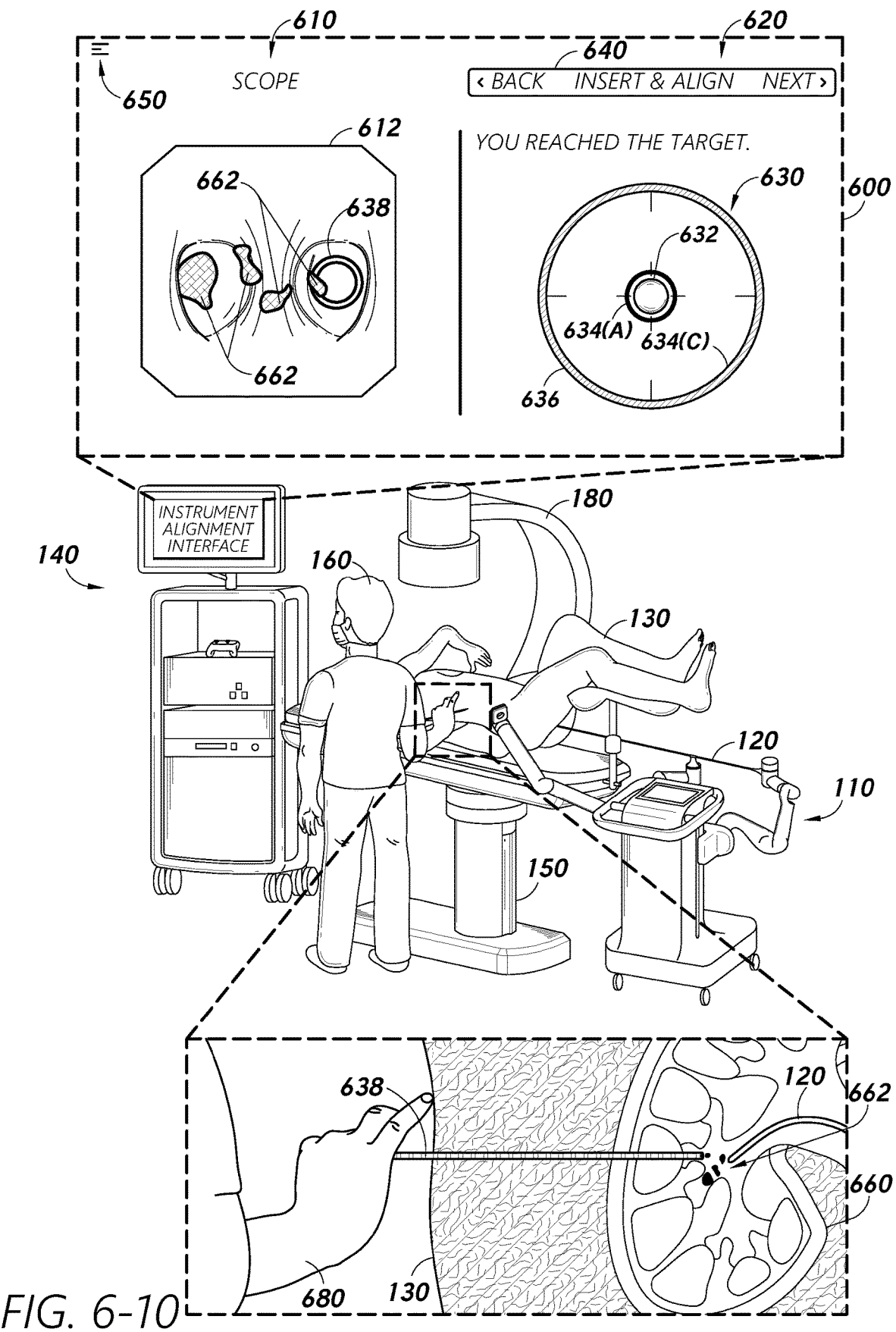

FIG. 10 illustrates an example flow diagram of a process 1000 for setting and/or updating a position change parameter associated with an instrument-alignment element in accordance with one or more embodiments. At block 1002, the process 1000 can include setting a position change parameter associated with a unit of movement of a medical instrument. For example, according to certain use cases, control circuitry can set a position change parameter to an initial value that is indicative of a particular amount of position change of the instrument-alignment element. The position change parameter can be indicative of an amount of position change of the instrument-alignment element within the interface with respect to a unit of movement of the medical instrument (e.g., a unit of orientation change). In some embodiments, the initial value includes a predetermined or default value that is associated with the medical instrument being located externally to a patient and/or outside a predetermined proximity to a target location. For example, the position change parameter can be set to the initial value when the medical instrument is being aligned before insertion of the medical instrument into the patient.

At block 1004, the process 1000 can include using the position change parameter to change a position of an instrument-alignment element based at least in part on a change in an orientation of the medical instrument. For example, according to certain use cases, control circuitry can determine that an orientation of a medical instrument has changed and, in response, use a position change parameter to change a position of an instrument-alignment element (e.g., use a value of the position change parameter to identify an amount of position change to apply to the instrument-alignment element).

At block 1006, the process 1000 can include determining if the medical instrument is closer to a target location. For example, according to certain use cases, control circuitry can determine whether or not a medical instrument is closer to a target location in comparison to a last position of the medical instrument. Such determination can be based at least in part on sensor data from the medical instrument. In some embodiments, the control circuitry can determine if the medical instrument is within a predetermined proximity to the target location.

If it is determined that the medical instrument it is closer to the target location, the process 1000 can proceed to block 1008. In contrast, if it is determined that the medical instrument it is not closer to the target location, the process 1000 can proceed back to block 1004 and continue to use the previously set position change parameter.

At block 1008, the process 1000 can include updating the position change parameter. For example, according to certain use cases, control circuitry can update a position change parameter to another value that is associated with more or less position change for a unit of movement of a medical instrument. In some embodiments, block 1008 can be implemented in any number of times to update the position change parameter one or more times as the medical instrument moves closer to the target location. Further, in some embodiments, block 1008 can be implemented once when the medical instrument is within a predetermined proximity to the target location. Here, the process 1000 may not return to block 1004 after implementing block 1008.

Example Robotic System

Figures 6, 7, 8, 9, 10, 11:
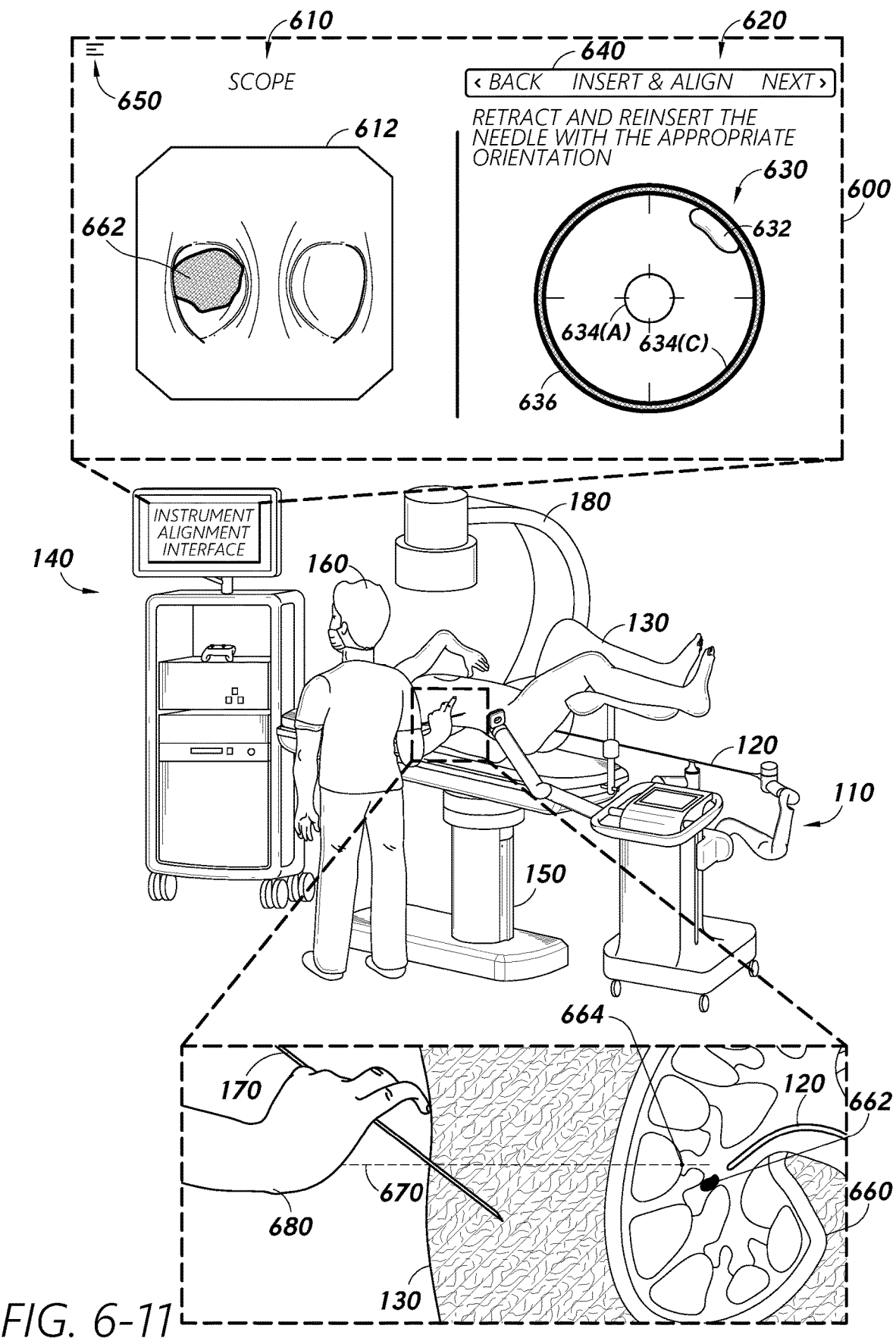
Figure 7:
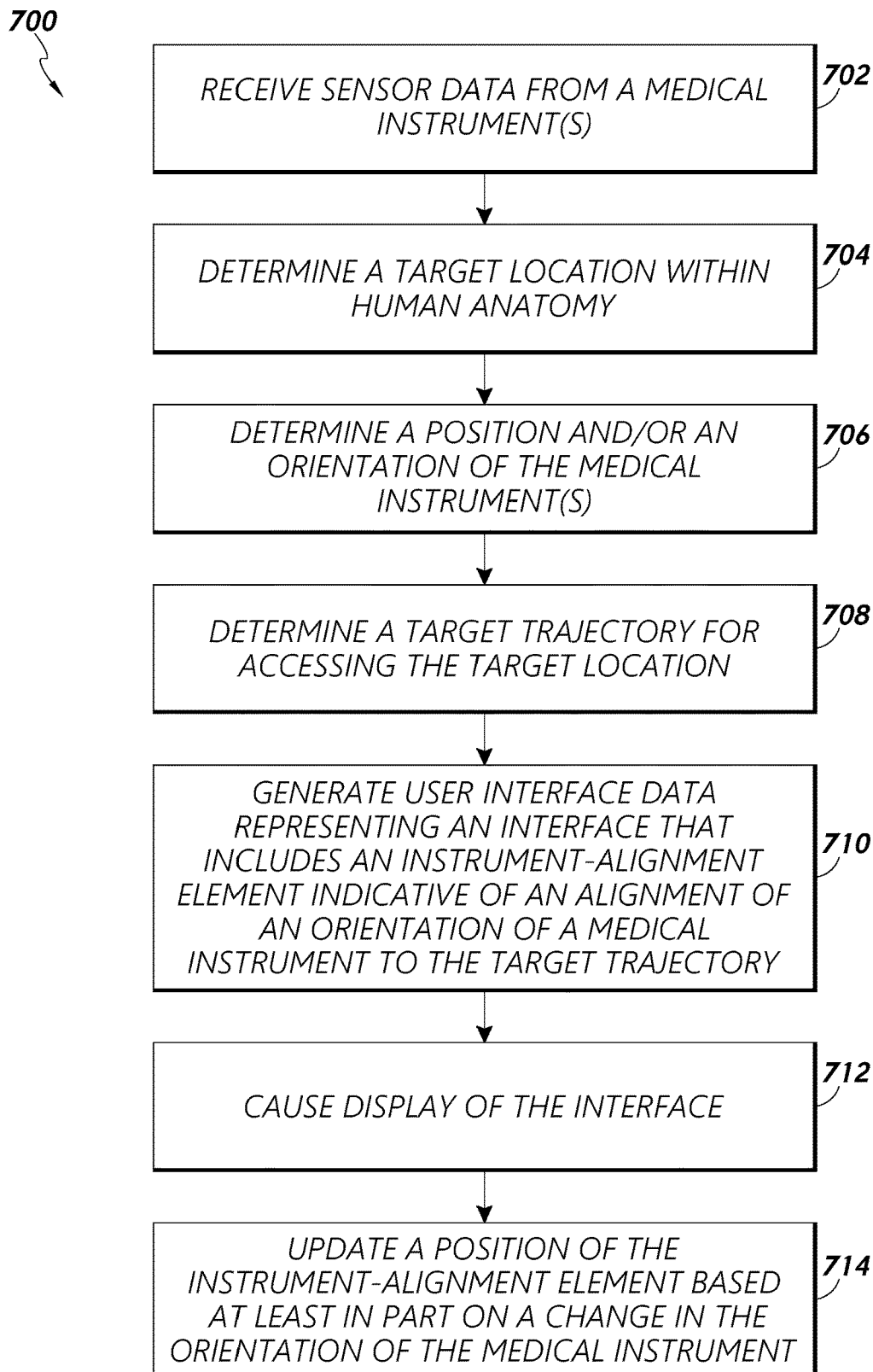
Figure 8:
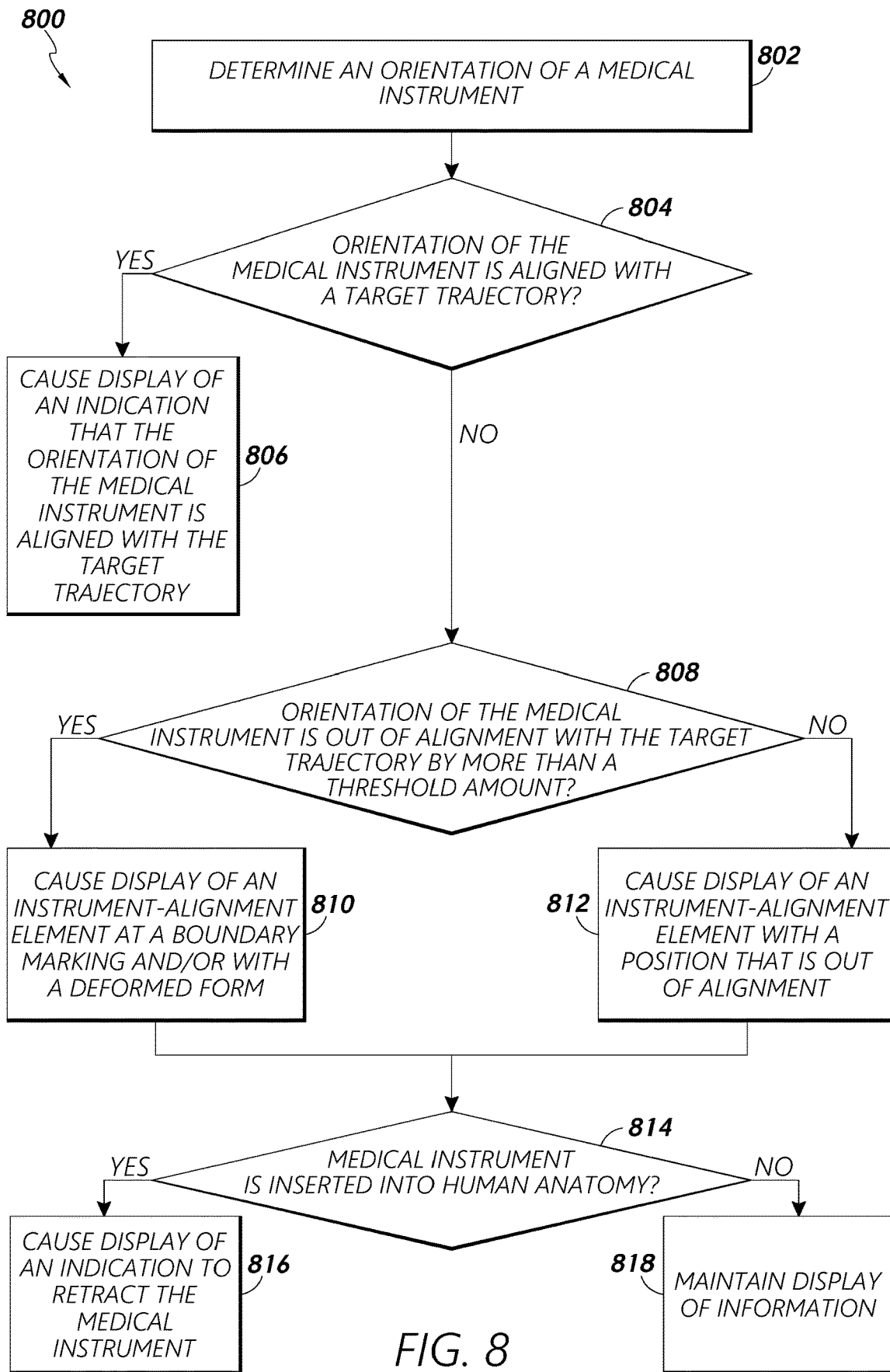
Figure 9:
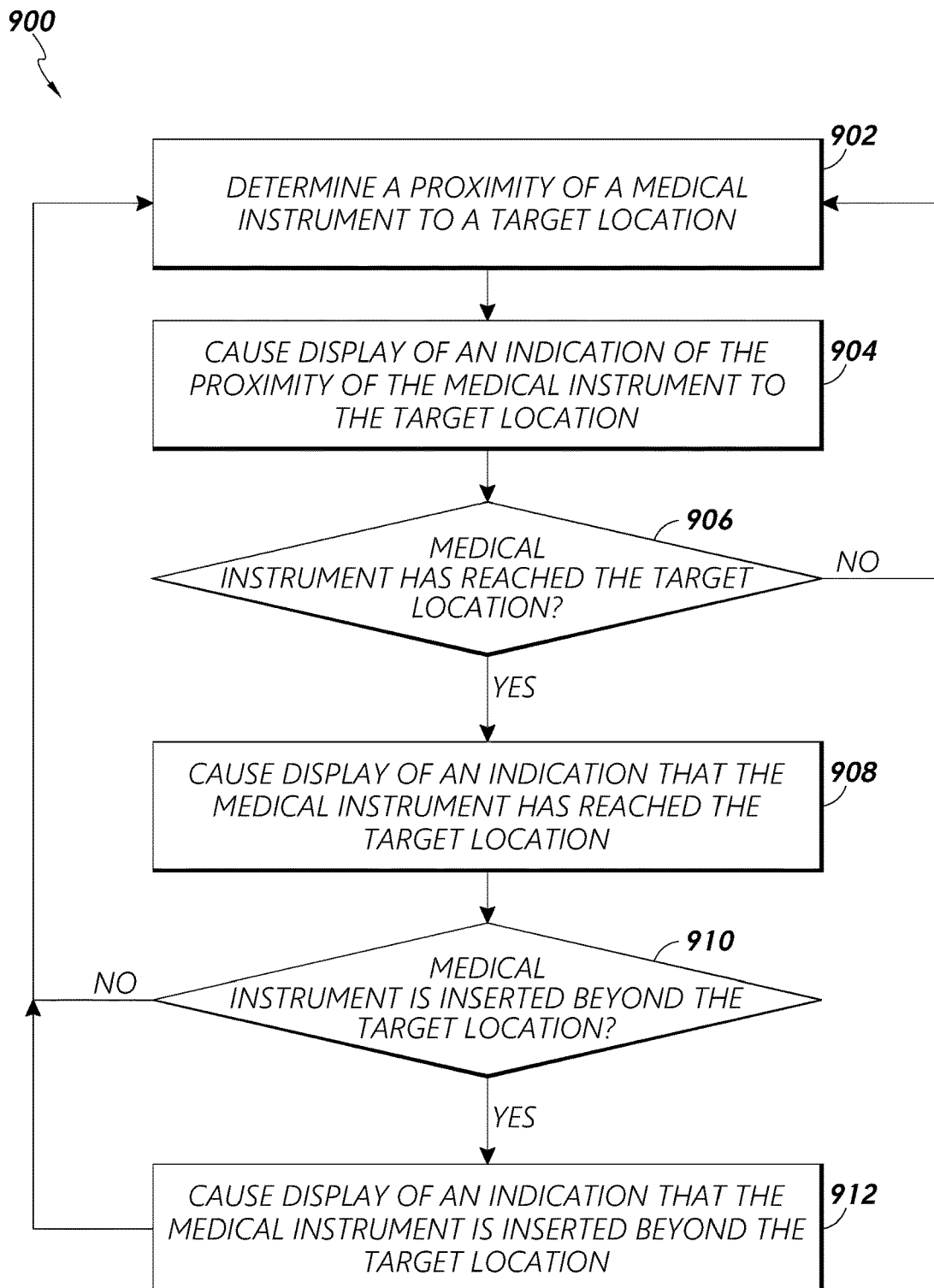
Figure 10:
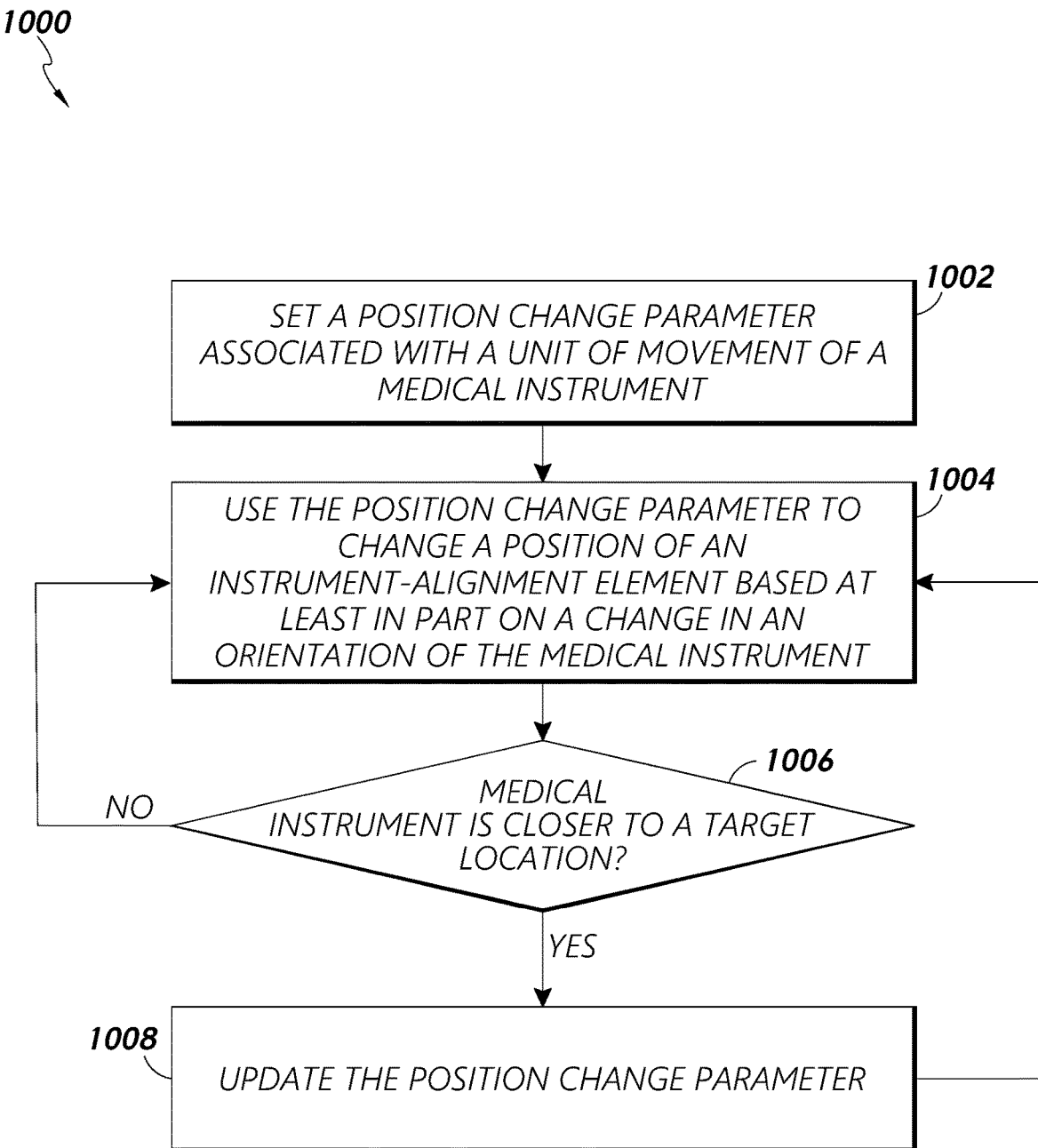
Figure 11:
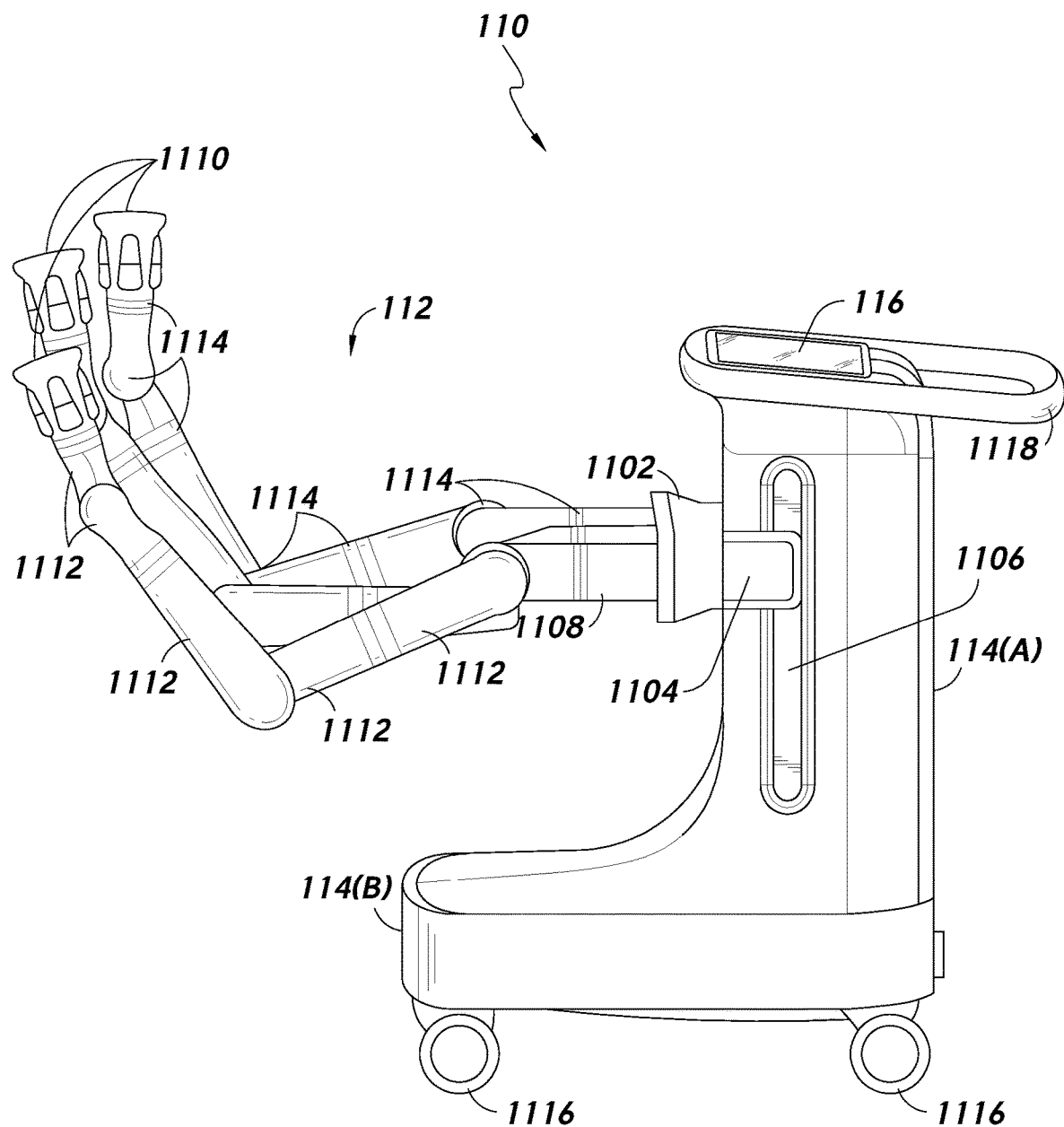

FIG. 11 illustrates example details of the robotic system 110 in accordance with one or more embodiments. In this example, the robotic system 110 is illustrated as a cart-based robotically-enabled system that is movable. However, the robotic system 110 can be implemented as a stationary system, integrated into a table, and so on.

The robotic system 110 can include the support structure 114 including an elongated section 114(A) (sometimes referred to as "the column 114(A)") and a base 114(B). The column 114(A) can include one or more carriages, such as a carriage 1102 (alternatively referred to as "the arm support 1102") for supporting the deployment of one or more the robotic arms 112 (three shown in FIG. 11). The carriage 1102 can include individually configurable arm mounts that rotate along a perpendicular axis to adjust the base of the robotic arms 112 for positioning relative to a patient. The carriage 1102 also includes a carriage interface 1104 that allows the carriage 1102 to vertically translate along the column 114(A). The carriage interface 1104 is connected to the column 114(A) through slots, such as slot 1106, that are positioned on opposite sides of the column 114(A) to guide the vertical translation of the carriage 1102. The slot 1106 includes a vertical translation interface to position and hold the carriage 1102 at various vertical heights relative to the base 114(B). Vertical translation of the carriage 1102 allows the robotic system 110 to adjust the reach of the robotic arms 112 to meet a variety of table heights, patient sizes, physician preferences. etc. Similarly, the individually configurable arm mounts on the carriage 1102 allow a robotic arm base 1108 of the robotic arms 112 to be angled in a variety of configurations. The column 114(A) can internally comprise mechanisms, such as gears and/or motors, that are designed to use a vertically aligned lead screw to translate the carriage 1102 in a mechanized fashion in response to control signals generated in response to user inputs, such as inputs from the I/O device(s) 116.

In some embodiments, the slot 1106 can be supplemented with a slot cover(s) that is flush and/or parallel to the slot surface to prevent dirt and/or fluid ingress into the internal chambers of the column 114(A) and/or the vertical translation interface as the carriage 1102 vertically translates. The slot covers can be deployed through pairs of spring spools positioned near the vertical top and bottom of the slot 1106. The covers can be coiled within the spools until deployed to extend and retract from their coiled state as the carriage 1102 vertically translates up and down. The spring-loading of the spools can provide force to retract the cover into a spool when the carriage 1102 translates towards the spool, while also maintaining a tight seal when the carriage 1102 translates away from the spool. The covers can be connected to the carriage 1102 using, for example, brackets in the carriage interface 1104 to ensure proper extension and retraction of the covers as the carriage 1102 translates.

The base 114(B) can balance the weight of the column 114(A), the carriage 1102, and/or arms 112 over a surface, such as the floor. Accordingly, the base 114(B) can house heavier components, such as one or more electronics, motors, power supply, etc., as well as components that enable movement and/or immobilize the robotic system 110. For example, the base 114(B) can include rollable wheels 1116 (also referred to as "the casters 1116") that allow for the robotic system 110 to move around the room for a procedure. After reaching an appropriate position, the casters 1116 can be immobilized using wheel locks to hold the robotic system 110 in place during the procedure. As shown, the robotic system 110 also includes a handle 1118 to assist with maneuvering and/or stabilizing the robotic system 110.

The robotic arms 112 can generally comprise robotic arm bases 1108 and end effectors 1110, separated by a series of linkages 1112 that are connected by a series of joints 1114. Each joint 1114 can comprise an independent actuator and each actuator can comprise an independently controllable motor. Each independently controllable joint 1114 represents an independent degree of freedom available to the robotic arm 112. For example, each of the arms 112 can have seven joints, and thus, provide seven degrees of freedom. However, any number of can be implemented with any degrees of freedom. In examples, a multitude of can result in a multitude of degrees of freedom, allowing for "redundant" degrees of freedom. Redundant degrees of freedom allow the robotic arms 112 to position their respective end effectors 1110 at a specific position, orientation, and/or trajectory in space using different linkage positions and/or joint angles. In some embodiments, the end effectors 1110 can be configured to engage with and/or control a medical instrument, a device, an object, and so on. The freedom of movement of the arms 112 can allow the robotic system 110 to position and/or direct a medical instrument from a desired point in space and/or allow a physician to move the arms 112 into a clinically advantageous position away from the patient to create access, while avoiding arm collisions.

As shown in FIG. 11, the robotic system 110 can also include the I/O device(s) 116. The I/O device(s) 116 can include a display, a touchscreen, a touchpad, a projector, a mouse, a keyboard, a microphone, a speaker, a controller, a camera (e.g., to receive gesture input), or another I/O device to receive input and/or provide output. The I/O device(s) 116 can be configured to receive touch, speech, gesture, or any other type of input. The I/O device(s) 116 can be positioned at the vertical end of column 114(A) (e.g., the top of the column 114(A)) and/or provide a user interface for receiving user input and/or for providing output. For example, the I/O device(s) 116 can include a touchscreen (e.g., a dual-purpose device) to receive input and provide a physician with pre-operative and/or intra-operative data. Example pre-operative data can include pre-operative plans, navigation, and/or mapping data derived from pre-operative computerized tomography (CT) scans, and/or notes from pre-operative patient interviews. Example intra-operative data can include optical information provided from a tool/instrument, sensor, and/or coordinate information from sensors, as well as vital patient statistics, such as respiration, heart rate, and/or pulse. The I/O device(s) 116 can be positioned and/or tilted to allow a physician to access the I/O device(s) 116 from a variety of positions, such as the side of the column 114(A) opposite the carriage 1102. From this position, the physician can view the I/O device(s) 116, the robotic arms 112, and/or a patient while operating the I/O device(s) 116 from behind the robotic system 110.

The robotic system 110 can include a variety of other components. For example, the robotic system 110 can include one or more control electronics/circuitry, power sources, pneumatics, optical sources, actuators (e.g., motors to move the robotic arms 112), memory, and/or communication interfaces (e.g. to communicate with another device). In some embodiments, the memory can store computer-executable instructions that, when executed by the control circuitry, cause the control circuitry to perform any of the operations discussed herein. For example, the memory can store computer-executable instructions that, when executed by the control circuitry, cause the control circuitry to receive input and/or a control signal regarding manipulation of the robotic arms 112 and, in response, control the robotic arms 112 to be positioned in a particular arrangement and/or to navigate a medical instrument connected to the end effectors 1110.

In some embodiments, robotic system 110 is configured to engage with and/or control a medical instrument, such as the scope 120. For example, the robotic arms 112 can be configured to control a position, orientation, and/or tip articulation of a scope (e.g., a sheath and/or a leader of the scope). In some embodiments, the robotic arms 112 can be configured/configurable to manipulate the scope 120 using elongate movement members. The elongate movement members can include one or more pull wires (e.g., pull or push wires), cables, fibers, and/or flexible shafts. To illustrate, the robotic arms 112 can be configured to actuate multiple pull wires coupled to the scope 120 to deflect the tip of the scope 120. Pull wires can include any suitable or desirable materials, such as metallic and/or non-metallic materials such as stainless steel, Kevlar, tungsten, carbon fiber, and the like. In some embodiments, the scope 120 is configured to exhibit nonlinear behavior in response to forces applied by the elongate movement members. The nonlinear behavior can be based on stiffness and compressibility of the scope 120, as well as variability in slack or stiffness between different elongate movement members.

Example Control System

Figure 12:
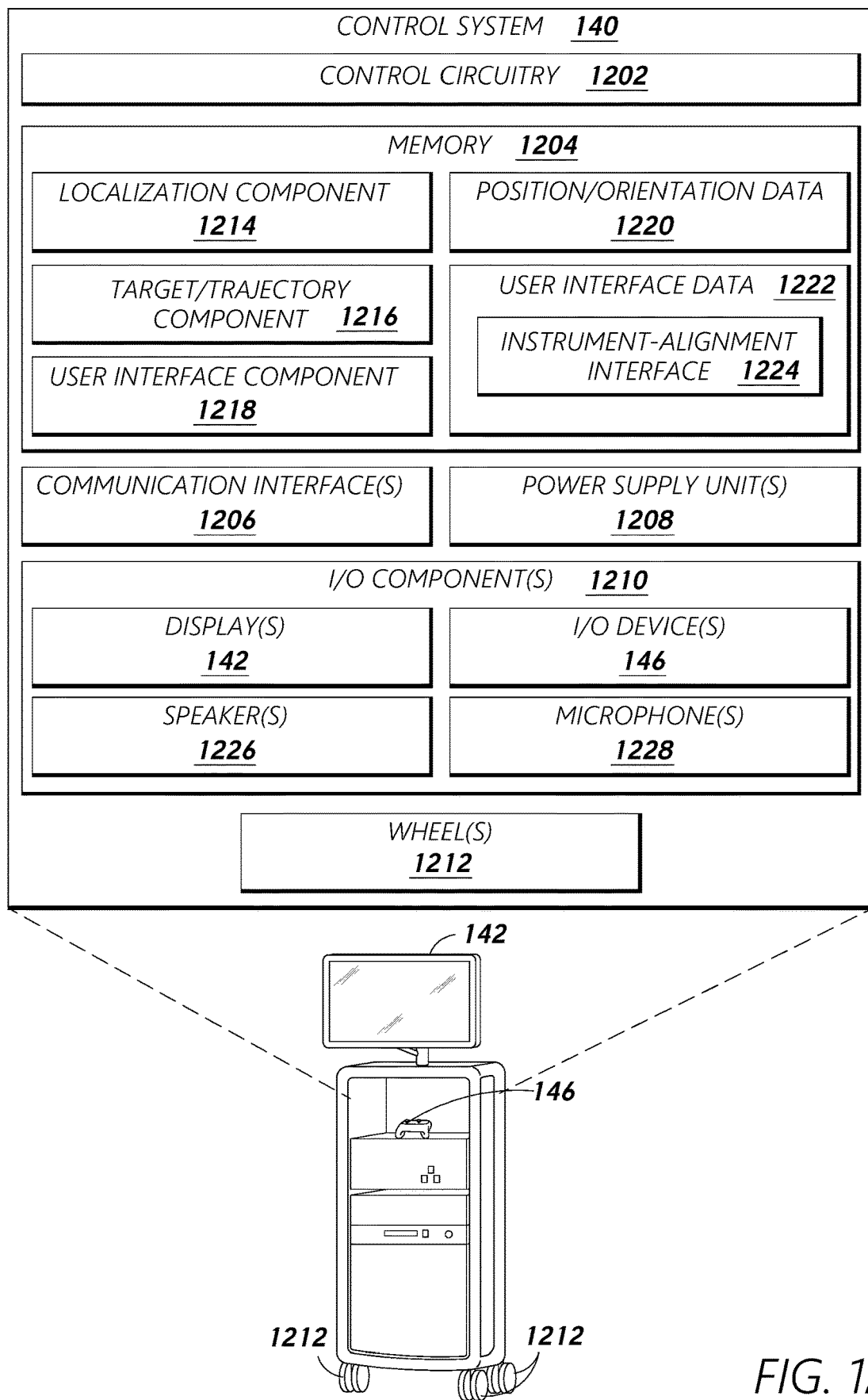
FIG. 12 illustrates example details of the control system of FIG. 1 in accordance with one or more embodiments.

FIG. 12 illustrates example details of the control system 140 in accordance with one or more embodiments. As illustrated, the control system 140 can include one or more of the following components, devices, modules, and/or units (referred to herein as "components"), either separately/individually and/or in combination/collectively: control circuitry 1202, data storage/memory 1204, one or more communication interfaces 1206, one or more power supply units 1208, one or more I/O components 1210, and/or one or more wheels 1212 (e.g., casters or other types of wheels). In some embodiments, the control system 140 can comprise a housing/enclosure configured and/or dimensioned to house or contain at least part of one or more of the components of the control system 140. In this example, the control system 140 is illustrated as a cart-based system that is movable with the one or more wheels 1212. In some cases, after reaching the appropriate position, the one or more wheels 1212 can be immobilized using wheel locks to hold the control system 140 in place. However, the control system 140 can be implemented as a stationary system, integrated into another system/device, and so on.

Although certain components of the control system 140 are illustrated in FIG. 12, it should be understood that additional components not shown can be included in embodiments in accordance with the present disclosure. Furthermore, certain of the illustrated components can be omitted in some embodiments. Although the control circuitry 1202 is illustrated as a separate component in the diagram of FIG. 12, it should be understood that any or all of the remaining components of the control system 140 can be embodied at least in part in the control circuitry 1202. That is, the control circuitry 1202 can include various devices (active and/or passive), semiconductor materials and/or areas, layers, regions, and/or portions thereof, conductors, leads, vias, connections, and/or the like, wherein one or more of the other components of the control system 140 and/or portion(s) thereof can be formed and/or embodied at least in part in/by such circuitry components/devices.

The various components of the control system 140 can be electrically and/or communicatively coupled using certain connectivity circuitry/devices/features, which can or may not be part of the control circuitry 1202. For example, the connectivity feature(s) can include one or more printed circuit boards configured to facilitate mounting and/or interconnectivity of at least some of the various components/circuitry of the control system 140. In some embodiments, two or more of the control circuitry 1202, the data storage/memory 1204, the communication interface(s) 1206, the power supply unit(s) 1208, and/or the input/output (I/O) component(s) 1210, can be electrically and/or communicatively coupled to each other.

As illustrated, the memory 1204 can include a localization component 1214, a target/trajectory component 1216, and a user interface component 1218 configured to facilitate various functionality discussed herein. In some embodiments, the localization component 1214, the target/trajectory component 1216, and/or the user interface component 1218 can include one or more instructions that are executable by the control circuitry 1202 to perform one or more operations. Although many embodiments are discussed in the context of the components 1214-1218 including one or more instructions that are executable by the control circuitry 1202, any of the components 1214-1218 can be implemented at least in part as one or more hardware logic components, such as one or more application specific integrated circuits (ASIC), one or more field-programmable gate arrays (FPGAs), one or more program-specific standard products (ASSPs), one or more complex programmable logic devices (CPLDs), and/or the like. Furthermore, although the components 1214-1218 are illustrated as being included within the control system 140, any of the components 1214-1218 can be implemented at least in part within another device/system, such as the robotic system 110, the table 150, or another device/system. Similarly, any of the other components of the control system 140 can be implemented at least in part within another device/system.

The localization component 1214 can be configured to perform one or more localization techniques to determine and/or track a position and/or an orientation of an object, such as a medical instrument. For example, the localization component 1214 can process input data (e.g., sensor data from a medical instrument, model data regarding anatomy of a patient, position data of a patient, pre-operative data, robotic command and/or kinematics data, etc.) to generate position/orientation data 1220 for one or more medical instruments. The position/orientation data 1220 can indicate a location and/or an orientation of one or more medical instruments relative to a frame of reference. The frame of reference can be a frame of reference relative to anatomy of a patient, a known object (e.g., an EM field generator), a coordinate system/space, and so on. In some implementations, the position/orientation data 1220 can indicate a location and/or an orientation of a distal end of a medical instrument (and/or proximal end, in some cases).

In some embodiments, the localization component 1214 can process pre-operative data to determine a position and/or an orientation of an object. The pre-operative data (sometimes referred to as "mapping data") can be generated by performing computed tomography (CT) scans, such as low dose CT scans. The pre-operative CT images from the scans can be reconstructed into three-dimensional images, which are visualized, e.g. as "slices" of a cutaway view of a patient's internal anatomy. When analyzed in the aggregate, image-based models for anatomical cavities, spaces, and/or structures of the patient's anatomy, such as a patient lung network, can be generated. A center-line geometry can be determined and/or approximated from the CT images to develop a three-dimensional volume of the patient's anatomy, referred to as model data (also referred to as "pre-operative model data" when generated using only pre-operative CT scans). Example uses of center-line geometry are discussed in U.S. patent application Ser. No. 14/523,760, the contents of which are herein incorporated by reference in its entirety. Network topological models can also be derived from CT-images.

Further, in some embodiments, the localization component 1214 can perform vision-based techniques to determine a position and/or an orientation of an object. For example, a medical instrument can be equipped with a camera, a range sensor (sometimes referred to as "a depth sensor"), a radar device, etc., to provide sensor data in the form of vision data. The localization component 1214 can process the vision data to facilitate vision-based location tracking of the medical instrument. For example, a pre-operative model data can be used in conjunction with vision data to enable computer vision-based tracking of a medical instrument (e.g., an endoscope). In examples, using pre-operative model data, the control system 140 can generate a library of expected endoscopic images based on the expected path of travel of a scope, with each image being linked to a location within the model. Intra-operatively, this library can be referenced by the control system 140 in order to compare real-time images and/or other vision data captured at a scope (e.g., a camera at a distal end of an endoscope) to those in the image library to assist with localization.

Moreover, in some embodiments, other types of vision-based techniques can be performed to determine a position and/or an orientation of an object. For example, the localization component 1214 can use feature tracking to determine motion of an image sensor (e.g., a camera or other sensor), and thus, a medical instrument associated with the image sensor. In some cases, the localization component 1214 can identify circular geometries in pre-operative model data that correspond to anatomical lumens and track the change of those geometries to determine which anatomical lumen was selected, as well as the relative rotational and/or translational motion of the medical instrument. Use of a topological map can also enhance vision-based algorithms or techniques. Furthermore, the localization component 1214 can use optical flow, another computer vision-based technique, to analyze displacement and/or translation of image pixels in a video sequence in vision data to infer camera movement. Examples of optical flow techniques can include motion detection, object segmentation calculations, luminance, motion compensated encoding, stereo disparity measurement, etc. By comparing multiple frames over multiple iterations, the localization component 1214 can determine movement and a location of an image sensor (and thus an endoscope).

Furthermore, in some embodiments, the localization component 1214 can use electromagnetic tracking to determine a position and/or an orientation of an object. For example, the localization component 1214 can use real-time EM tracking to determine a real-time location of a medical instrument in a coordinate system/space that can be registered to the patient's anatomy, which can be represented by a pre-operative model or other model. In EM tracking, an EM sensor (or tracker) including one or more sensor coils can be embedded in one or more locations and/or orientations in a medical instrument (e.g., a scope, a needle, etc.). The EM sensor can measure a variation in an EM field created by one or more static EM field generators positioned at a known location. The location information detected by the EM sensors can be stored as EM data. The localization component 1214 can process the EM data to determine a position and/or orientation of an object, such as a medical instrument. An EM field generator (or transmitter) can be placed close to the patient (e.g., within a predetermined distance) to create a low intensity magnetic field that an EM sensor can detect. The magnetic field can induce small currents in the sensor coils of the EM sensor, which can be analyzed to determine a distance and/or angle between the EM sensor and the EM field generator. These distances and/or orientations can be intra-operatively "registered" to patient anatomy (e.g., a pre-operative model) in order to determine a geometric transformation that aligns a single location in a coordinate system with a position in the pre-operative model of the patient's anatomy. Once registered, an EM sensor (e.g., an embedded EM tracker) in one or more positions of a medical instrument (e.g., the distal tip of an endoscope, a needle, etc.) can provide real-time indications of a position and/or an orientation the medical instrument through the patient's anatomy.

Additionally or alternatively, in some embodiments, the localization component 1214 can use robotic command and/or kinematics data to determine a position and/or an orientation of an object. Robotic command and/or kinematics data can be indicative of pitch and/or yaw (e.g., of a robotic arm) resulting from an articulation command, such as those used during pre-operative calibration and/or during a procedure. Intra-operatively, calibration measurements can be used in combination with known insertion depth information to estimate a position and/or an orientation of a medical instrument. Alternatively or additionally, these calculations can be analyzed in combination with EM, vision, and/or topological modeling to estimate a position and/or orientation of a medical instrument.

Further, in some embodiments, the localization component 1214 can use other types of data to determine a position and/or an orientation of an object. For example, the localization component 1214 can analyze sensor data from a shape sensing fiber (e.g., which can provide shape data regarding a location/shape of a medical instrument), an accelerometer, a gyroscope, a satellite-based positioning sensor (e.g., a global positioning system (GPS)), a radio-frequency transceiver, and so on, embedded on a medical instrument. Such data can be indicative of a position and/or an orientation of the medical instrument.

In some embodiments, the localization component 1214 can use input data in combination. For example, the localization component 1214 can use a probabilistic approach where a confidence weight is assigned to a position/orientation determined from multiple forms of input data. To illustrate, if EM data is not as reliable (as may be the case where there is EM interference), the EM data can be associated with a relatively low confidence value and other forms of input data can be relied on, such as vision data, robotic command and kinematics data, and so on.

The target/trajectory component 1216 can be configured to determine a position of a target location within the human anatomy and/or a coordinate space/system. A target location can represent a point/point set within the human anatomy and/or a coordinate space/system. For example, the target/trajectory component 1216 can identify one or more points for a target location within a coordinate system, identify coordinates for the one or more points (e.g., X, Y, Z coordinates for each point), and associate the coordinates with the target location. In some embodiments, the target/trajectory component 1216 can use a position and/or orientation of a medical instrument to determine a position of a target location. For example, a scope can be navigated to contact or be within proximity to a target location (e.g., parked in-front of the target location). The localization component 1214 can use localization techniques to determine a position of the scope (e.g., a location of the end of the scope) and/or a position of an object within a field-of-view of the scope. The target/trajectory component 1216 can associate the position of the scope (e.g., the coordinates of the scope) with the target location. Additionally or alternatively, in some embodiments, a scope can deliver a fiducial to mark a target location and a position of the fiducial can be determined.

A target location can represent a fixed or movable point(s) within the human anatomy and/or a coordinate space/system. For example, if a papilla is initially designated as a target location, coordinates for the target location can be determined and updated as the procedure proceeds and the papilla moves (e.g., due to insertion of a medical instrument). Here, a location of a scope (which can be within proximity to the papilla) can be tracked over time and used to update the coordinates of the target location. In some embodiments, the target/trajectory component 1216 can estimate/predict a position of a target location. Here, the target location can be represented with the predicted position. For example, the target/trajectory component 1216 can use an algorithm to predict coordinates of the target location as the human anatomy moves. The predicted coordinates can be used to determine a target trajectory.

The target/trajectory component 1216 can also be configured to determine a target trajectory for a medical instrument or another object. A target trajectory can represent a desired path for accessing a target location. A target trajectory can be determined based on a variety of information, such as a position of a medical instrument(s) (e.g., a needle, a scope, etc.), a target location within the human anatomy, a position and/or orientation of a patient, the anatomy of the patient (e.g., the location of organs within the patient relative to the target location), and so on. For example, a target trajectory can include a line that extends from a position of a medical instrument and/or a location on the skin of a patient to/through a position of a target location within the patient. In examples, a physician can analyze images or models of the human anatomy and provide input to designate a target trajectory, such as by drawing a line on an image of the internal anatomy of a patient. In some embodiments, the target/trajectory component 1216 can calculate a target trajectory initially and/or update the target trajectory throughout the procedure. For example, as a target location moves during the procedure, a target trajectory can be updated due to the change in position of the target location. In examples where a target location is estimated, a target trajectory can represent an estimated path to reach the target location.

In some embodiments, a target trajectory and/or a trajectory of a medical instrument can be defined/represented with respect to one or more anatomical planes/axes. For example, a trajectory can be defined/represented as an angle with respect to the coronal/sagittal/transverse plane(s) or another plane/axis (e.g., a 20 degree cranial-caudal angle, 10 degree medial-lateral angle, etc.). To illustrate, the control system 140 can determine a pose of a medical instrument with respect to an EM field generator and/or a location of a target with respect to the EM field generator. The control system 140 can also determine, based on robotic kinematics, a pose of the EM field generator with respect to a robotic system. In some cases, the control system 140 can infer/determine that the robotics system is parallel to the bed. Based on such information, the control system 140 can determine a target trajectory and/or a trajectory of the medical instrument within respect to an anatomical plane, such as an angle with respect to an anatomical plane for the patient on the bed.

The user interface component 1218 can be configured to facilitate one or more user interfaces (also referred to as "one or more graphical user interfaces (GUI)"). For example, the user interface component 1218 can generate user interface data 1222 representing an instrument-alignment interface 1224 that includes one or more visualizations to indicate an orientation and/or position of a medical instrument. The user interface component 1228 can use the position/orientation data 1220 regarding a medical instrument, information regarding a target location, and/or information regarding a target trajectory to present, within the instrument-alignment interface 1224, one or more visualizations indicative of an alignment of an orientation of the medical instrument relative to the target trajectory and/or a proximity of the medical instrument to the target location. Further, the user interface component 1228 can use vision data, such as images captured by a scope, to present information within the instrument-alignment interface 1224. In examples, information can be overlaid on images from a scope (e.g., augmented image view). The user interface component 1228 can provide the user interface data 1222 or other data to the one or more displays 142 and/or another display(s) for display of the instrument-alignment interface 1224.

The one or more communication interfaces 1206 can be configured to communicate with one or more device/sensors/systems. For example, the one or more communication interfaces 1206 can send/receive data in a wireless and/or wired manner over a network. A network in accordance with embodiments of the present disclosure can include a local area network (LAN), wide area network (WAN) (e.g., the Internet), personal area network (PAN), body area network (BAN), etc. In some embodiments, the one or more communication interfaces 1206 can implement a wireless technology such as Bluetooth, Wi-Fi, near field communication (NFC), or the like.

The one or more power supply units 1208 can be configured to manage power for the control system 140 (and/or the robotic system 110, in some cases). In some embodiments, the one or more power supply units 1208 include one or more batteries, such as a lithium-based battery, a lead-acid battery, an alkaline battery, and/or another type of battery. That is, the one or more power supply units 1208 can comprise one or more devices and/or circuitry configured to provide a source of power and/or provide power management functionality. Moreover, in some embodiments the one or more power supply units 1208 include a mains power connector that is configured to couple to an alternating current (AC) or direct current (DC) mains power source.

The one or more I/O components 1210 can include a variety of components to receive input and/or provide output, such as to interface with a user. The one or more I/O components 1210 can be configured to receive touch, speech, gesture, or any other type of input. In examples, the one or more I/O components 1210 can be used to provide input regarding control of a device/system, such as to control the robotic system 110, navigate the scope or other medical instrument attached to the robotic system 110, control the table 150, control the fluoroscopy device 190, and so on. As shown, the one or more I/O components 1210 can include the one or more displays 142 (sometimes referred to as "the one or more display devices 142") configured to display data. The one or more displays 142 can include one or more liquid-crystal displays (LCD), light-emitting diode (LED) displays, organic LED displays, plasma displays, electronic paper displays, and/or any other type(s) of technology. In some embodiments, the one or more displays 142 include one or more touchscreens configured to receive input and/or display data. Further, the one or more I/O components 1210 can include the one or more I/O devices 146, which can include a touchscreen, touch pad, controller, mouse, keyboard, wearable device (e.g., optical head-mounted display), virtual or augmented reality device (e.g., head-mounted display), etc. Additionally, the one or more I/O components 1210 can include one or more speakers 1226 configured to output sounds based on audio signals and/or one or more microphones 1228 configured to receive sounds and generate audio signals. In some embodiments, the one or more I/O components 1210 include or are implemented as a console.

Although not shown in FIG. 12, the control system 140 can include and/or control other components, such as one or more pumps, flow meters, valve controls, and/or fluid access components in order to provide controlled irrigation and/or aspiration capabilities to a medical instrument (e.g., a scope), a device that can be deployed through a medical instrument, and so on. In some embodiments, irrigation and aspiration capabilities can be delivered directly to a medical instrument through separate cable(s). Further, the control system 140 can include a voltage and/or surge protector designed to provide filtered and/or protected electrical power to another device, such as the robotic system 110, thereby avoiding placement of a power transformer and other auxiliary power components in robotic system 110, resulting in a smaller, more moveable robotic system 110.

The control system 140 can also include support equipment for sensors deployed throughout the medical system 100. For example, the control system 140 can include opto-electronics equipment for detecting, receiving, and/or processing data received from optical sensors and/or cameras. Such opto-electronics equipment can be used to generate real-time images for display in any number of devices/systems, including in the control system 140. Similarly, the control system 140 can include an electronic subsystem for receiving and/or processing signals received from deployed electromagnetic (EM) sensors. In some embodiments, the control system 140 can also be used to house and position an EM field generator for detection by EM sensors in or on a medical instrument.

In some embodiments, the control system 140 can be coupled to the robotic system 110, the table 150, and/or a medical instrument, such as the scope 120 and/or the needle 170, through one or more cables or connections (not shown). In some implementations, support functionality from the control system 140 can be provided through a single cable, simplifying and de-cluttering an operating room. In other implementations, specific functionality can be coupled in separate cabling and connections. For example, while power can be provided through a single power cable, the support for controls, optics, fluidics, and/or navigation can be provided through a separate cable.

The term "control circuitry" is used herein according to its broad and ordinary meaning, and can refer to any collection of one or more processors, processing circuitry, processing modules/units, chips, dies (e.g., semiconductor dies including come or more active and/or passive devices and/or connectivity circuitry), microprocessors, micro-controllers, digital signal processors, microcomputers, central processing units, graphics processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

The term "memory" is used herein according to its broad and ordinary meaning and can refer to any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

Computer-readable media that can be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

Example Target Planes and Projected Locations

Various techniques herein provide/generate information about an orientation/position of a medical instrument and/or a target trajectory/location. In many examples, such techniques are discussed in the context of a scope that rendezvous with another medical device, such as a needle, catheter, etc., to facilitate removal of a kidney stone or another object from a patient. However, the techniques can be implemented in other contexts. For ease of discussion, many examples will refer to a needle; although other medical instruments can be implemented, as noted above.

In one illustration, as similarly discussed in examples above, a physician can navigate a scope to a location within a kidney where a kidney stone is located. The scope can be navigated to contact a papilla and/or otherwise be positioned in proximity to the papilla. The physician can then provide input to register the position of the scope as a target location for a needle to enter the kidney percutaneously. The needle can be equipped with an EM sensor or another type of sensor to provide sensor data, which can be used to determine an orientation/position of the needle. The position/orientation of the needle and/or the position of the target (i.e., the papilla) can be mapped to/projected onto a representation, such as a 2D representation/plane, 3D representation, etc.

The mapping can be used to estimate/determine an error/difference between the current needle pose and the target location (sometimes referred to as "targeting error" or "trajectory alignment error"). Targeting error can include angular targeting error that represents an angular error with respect to a target trajectory/pose (e.g., a desired/ideal trajectory/pose for a medical instrument) and/or positional targeting error that represents a positional error with respect to a target location. In examples, angular targeting error and/or positional targeting error can be represented/indicated in targeting data. The targeting data can be used to generate/provide information regarding an alignment/progress of the needle relative to the target location. This can assist a user in inserting the needle to reach the target location. For example, targeting data can be used to present any of the user interfaces discussed herein.

In some embodiments, one or more of the techniques discussed herein can be implemented for a moving target (sometimes referred to as a "live target"), such as a target location that can experience movement during a procedure. In examples, a target location that is set to and/or based on a position of a scope and/or anatomy of a patient can move due to anatomical motion and/or tissue deformation when a needle is inserted. In some instances, the location of the target (e.g., papilla) can be updated as the needle is inserted, such as in real-time using the tracked scope pose and/or performing other localization techniques.

Figure 13:
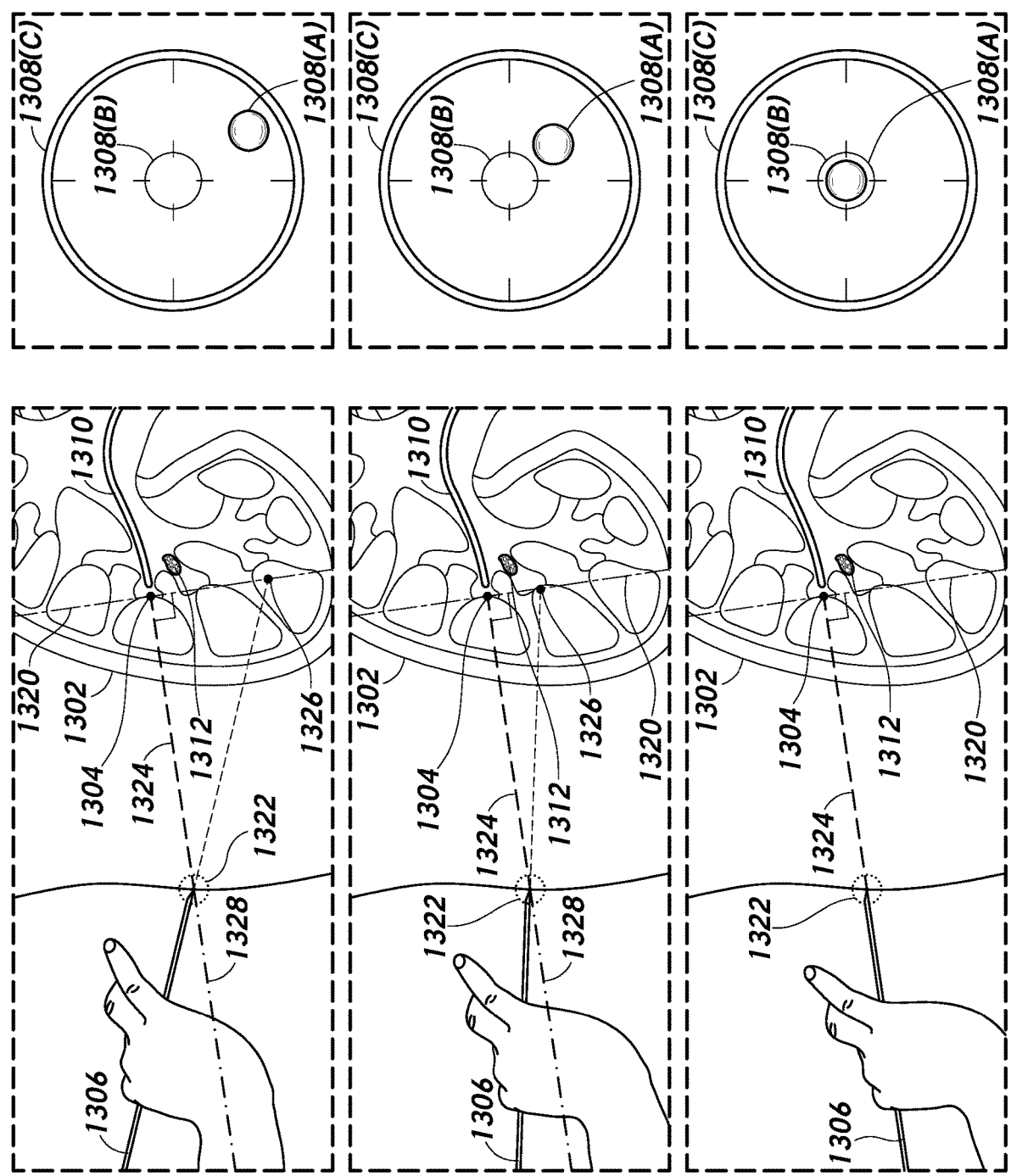

FIGS. 13-16 illustrate examples techniques of mapping a needle pose onto a representation and using such mapping to provide interface data in accordance with one or more embodiments. In these examples, images on the left depict anatomy of a patient (including a kidney 1302/1402/1502/1602), as well as a target location 1304/1404/1504/1604 and a pose of a needle 1306/1406/1506/1606. Meanwhile, images on the right depict one or more interface elements 1308/1408/1508/1608 that can be provided via an interface to indicate the pose of the needle 1302/1402/1502/1602 relative to the target location 1304/1404/1504/1604. For example, as shown in FIGS. 13-1 through 13-3, the one or more interface elements 1308 can include an instrument alignment element 1308(A) representing the needle 1306 and an alignment marking 1308(B) representing the target location 1304. In general, when the needle 1306 is aligned with the target location 1304, the instrument alignment element 1308(A) can be displayed in an aligned arrangement with the alignment markings 1308(B)/1308(C) (e.g., centered within the alignment marking 1308(B)). In FIGS. 13-16, the target location 1304/1404/1504/1604 can be designated by a scope 1310/1410/1510/1610, which can be used to remove a kidney stone 1312/1412/1512/1612.

FIGS. 13-1 through 13-3 illustrate example techniques of mapping the pose of the needle 1306 onto a representation/plane 1320 (sometimes referred to as "the target plane 1320") that remains fixed as the pose of the needle 1306 changes. As shown in FIG. 13-1, the user can position the needle at an initial location 1322, such as on an insertion site on the skin of the patient or otherwise fix the distal end of the needle 1306 to a position. A line 1324 can then be determined between a distal end of the needle 1306 (e.g., needle tip) and the target location 1304. The plane 1320 can be determined such that the line 1324 is normal to the plane 1320 and the plane 1320 includes the target location 1304. A projected position 1326 can be then determined for the needle 1306 on the plane 1320. For example, a position of the needle 1306 can be projected onto the plane 1320 based on the current orientation/heading of the needle 1306. The projected position 1326 can represent an intersection of the needle 1306 with the plane 1320 if the needle 1306 were to be inserted to the plane 1320 with the current orientation/heading. As shown, a target trajectory/pose for the needle 1306 can include the line 1324 and/or a line 1328. The target trajectory/pose can represent a trajectory/pose that should be followed to successfully reach/align with the target location 1304. Further, in some instances, a target trajectory can include a heading of the scope 1310, which may or may not be the same as the line 1324.

The projected position 1326 can be used to present the one or more interface elements 1308, so that the user can view an alignment of the needle 1306 relative to the target location 1304. For example, the alignment marking 1308(B) can represent the target location 1304 on the plane 1320 and the instrument alignment element 1308(A) can represent the projected position 1326 of the needle 1306 on the plane 1320. The position of the instrument alignment element 1308(A) relative to the alignment marking 1308(B) can indicate an alignment of the needle 1306 to the target location 1304. For instance, as shown in FIGS. 13-1 through 13-3, as the orientation of the needle 1306 is changed (e.g., the user tilts the needle 1306) to align with the target pose 1328, the instrument alignment element 1308(A) moves closer to/within the alignment marking 1308(B). FIG. 13-3 illustrates the needle 1306 aligned with the target pose 1328 (i.e., the projected position 1326 aligned with the target location 1304). In some examples, the positioning of the one or more interface elements 1308 represents an angular targeting error; namely, a difference between the orientation of the needle 1306 and the target pose 1328.

In some cases, to facilitate the position of one or more interface elements 1308 within the interfaces of FIGS. 13-1 through 13-3, the plane 1320 can be mapped to the interface. That is, a location on the plane 1320 can be mapped to a location within the interface. For example, a particular location on the plane 1320 can be associated with the outer alignment marking 1308(C), such that the instrument alignment element 1308(A) can be positioned near the alignment marking 1308(C) if the projected position 1326 is positioned within proximity to the particular location on the plane 1320.

As noted above, the orientation of the plane 1320 can remain fixed as the pose of the needle 1306 changes. For example, during the needle-insertion phase of the procedure (e.g., while inserting the needle 1306 in an attempt to reach the target location 1304), the orientation of the plane 1320 can remain the same, even if the orientation/position of the needle 1306 changes. As such, the plane 1320 generally represents a fixed plane that is formulated based on an initial fixed position of the needle 1306. In some cases, the plane 1320 can be determined when the distal end of the needle 1306 is initially positioned at a relatively fixed position, such as on the skin of the patient. The fixed position can be detected based on user input indicating that the position is fixed (e.g., switching to a needle alignment interface, selecting a particular icon, etc.), less than a threshold amount of orientation movement of the needle 1320 with the needle tip at a relatively stationary position, and so on. However, in instances, the plane 1320 can be updated based on detecting a new fixed position of the needle 1306 (e.g., orientation movement about a fixed tip point), input provided by a user indicating a new fixed needle position, and so on.

Figure 14:
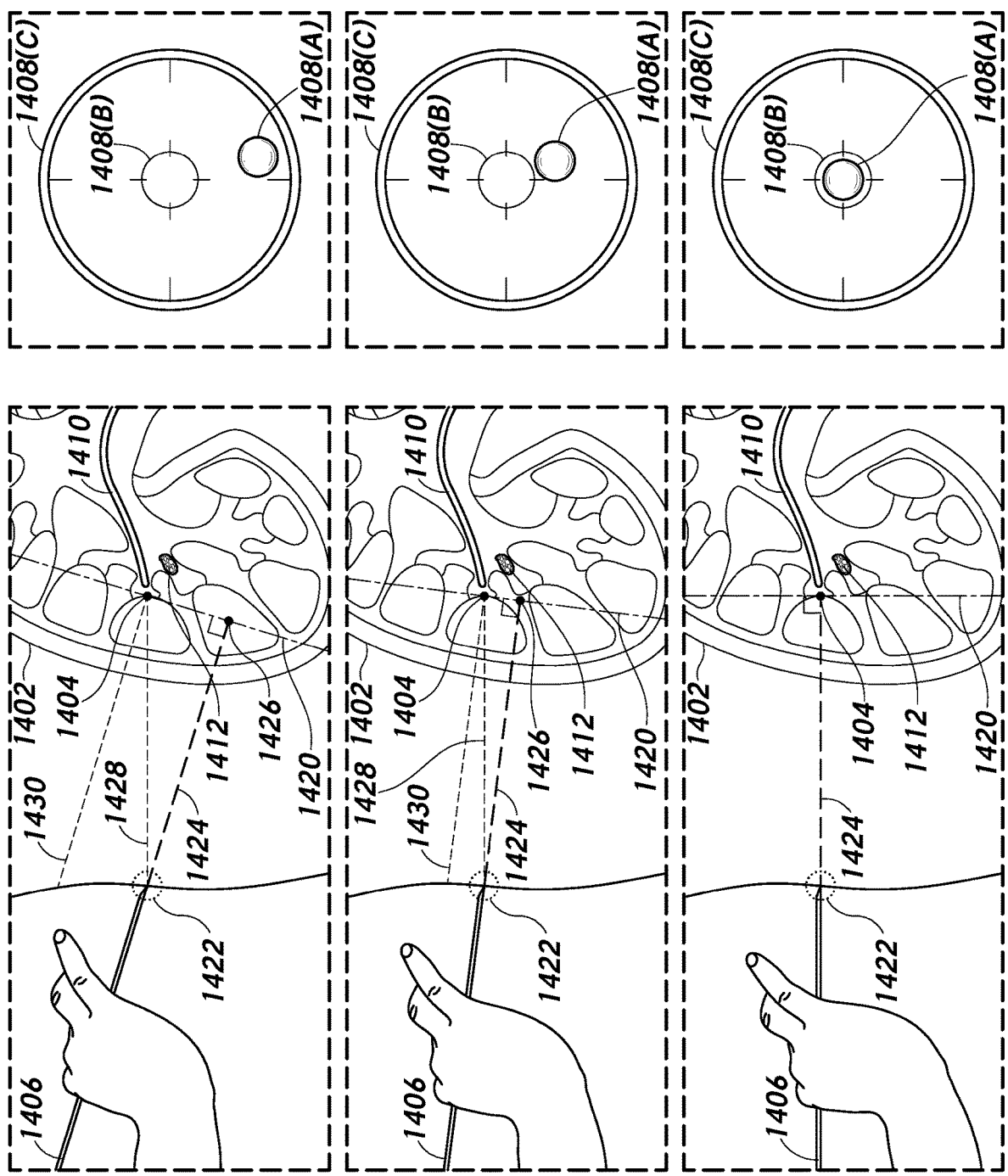

FIGS. 14-1 through 14-3 illustrate example techniques of mapping the pose of the needle 1406 onto a representation/plane 1420 that updates as the pose of the needle 1406 changes in accordance with one or more embodiments. In this example, the user changes the orientation of the needle 1406 without changing the position of the tip of the needle 1406. As shown in FIG. 14-1, the user can position the needle at an initial location 1422. The plane 1420 can be determined such that a heading 1424 of the needle 1406 is normal to the plane 1420 and the plane 1420 includes the target location 1404. A projected position 1426 can be then determined for the needle 1406 on the plane 1420 based on the current orientation/heading of the needle 1406.

A target trajectory/pose for the needle 1406 can be determined in a variety of manners. In one illustration, a target trajectory/pose can be/include a line 1428 between a distal end of the needle 1406 and the target location 1404. When the line 1428 is used as a reference, the one or more interface elements 1408 can represent an angular error for the needle 1406 (e.g., an angular difference between the pose of the needle 1406 and the line 1428). In another illustration, a target trajectory/pose can be/include a line 1430 that is parallel to the initial heading of the needle 1406 and passes through the target location 1404 (e.g., the line 1430 can be normal to the plane 1420). When the line 1430 is used as a reference, the one or more interface elements 1408 can represent a positional error for the needle 1406 (e.g., a positional difference on the plane 1420 between the projected position 1426 of the needle 1406 and the target location). In examples, a target trajectory/pose includes/aligns with a heading of the scope 1410. In any event, a target trajectory can update as the pose of the needle 1406 changes.

The projected position 1426 can be used to present the one or more interface elements 1408, so that the user can view an alignment of the needle 1406 relative to the target location 1404. For example, the alignment marking 1408(B) can represent the target location 1404 and the instrument alignment element 1408(A) can represent the projected position 1426 of the needle 1406. The position of the instrument alignment element 1408(A) relative to the alignment marking 1408(B) can indicate an alignment of the needle 1406 to the target location 1404. In this example, the user leaves the tip of the needle 1406 fixed at the initial location 1422 and changes the orientation of the needle 1406. As shown in FIGS. 14-1 through 14-3, as the orientation of the needle 1406 changes to align with the target trajectory 1428/1430 (which changes as the needle 1406 moves), the instrument alignment element 1408(A) moves closer to/within the alignment marking 1408(B). FIG. 14-3 illustrates the needle 1406 aligned with the target pose 1428/1430 (i.e., the projected position 1426 is aligned with the target location 1404). As such, although the interface generally provides both angular and positional error of the needle 1406 relative to the target trajectory, the user is using the interface to view angular error, since the user is changing the orientation of the needle 1406 without changing the tip position.

As similarly discussed above in reference to FIGS. 13-1 through 13-3, the plane 1420 can be mapped to the interface to display the one or more interface elements 1408 at the appropriate position within the interface and/or relative to each other.

Figures 1, 2, 3, 15:
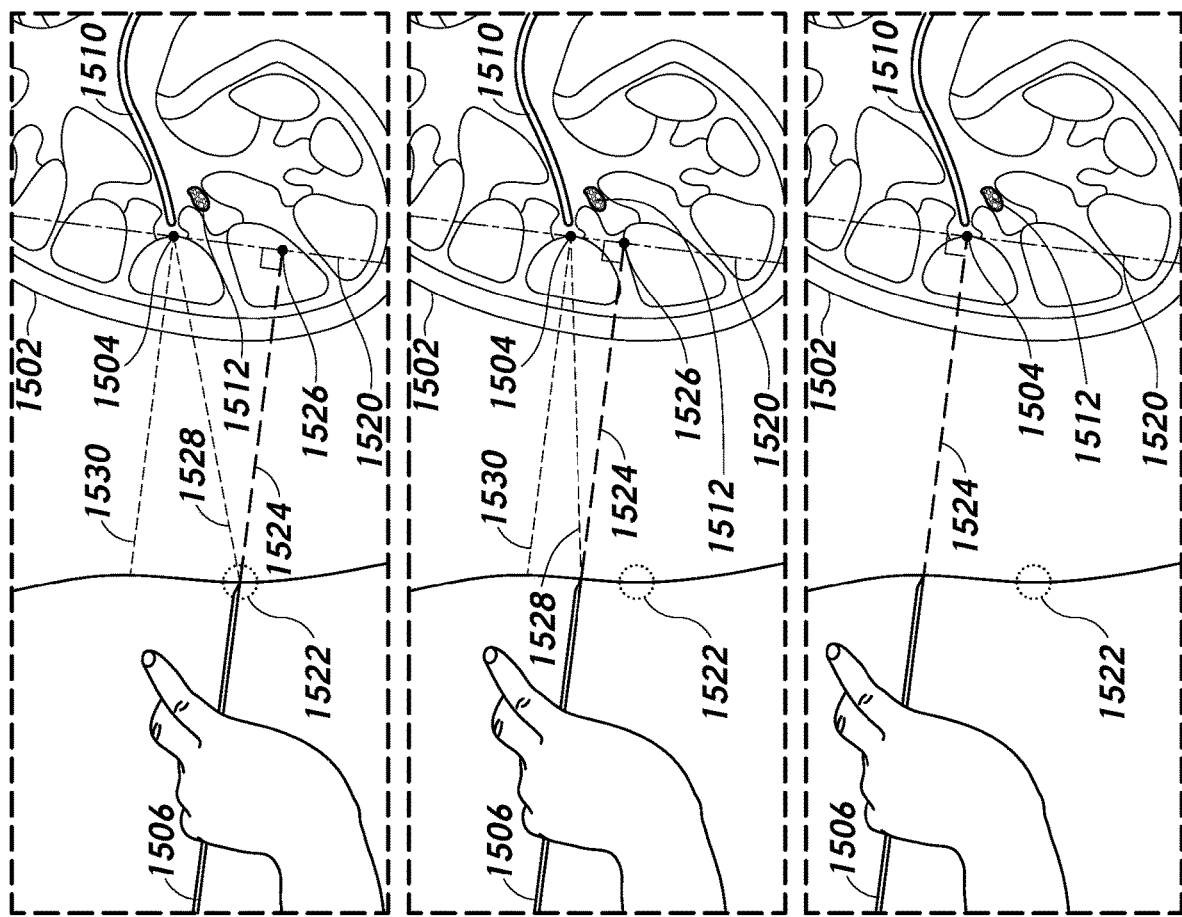

FIGS. 15-1 through 15-3 illustrate another example of mapping the pose of the needle 1506 onto a representation/plane 1520 that updates as the pose of the needle 1506 changes. In this example, the user changes the position of the tip of the needle 1506 without changing the orientation of the needle 1506. As shown in FIG. 15-1, the plane 1520 can be determined in a similar manner as that discussed in reference to FIGS. 14-1 through 14-3. In particular, the user can position the needle at an initial location 1522. The plane 1520 can then be determined such that a heading 1524 of the needle 1506 is normal to the plane 1520 and the plane 1520 includes the target location 1504. A projected position 1526 can be determined for the needle 1506 on the plane 1520 based on the current orientation/heading of the needle 1506.

As similarly discussed above in FIGS. 14-1 through 14-3, a target trajectory/pose for the needle 1506 can be determined to be/include (i) a line 1528 between a distal end of the needle 1506 and the target location 1504, and/or (ii) a line 1530 that is parallel to the initial pose of the needle 1506 and passes through the target location 1504. The target trajectory can update as the pose of the needle 1506 changes.

The projected position 1526 can be used to present the one or more interface elements 1508. For example, the position of the instrument alignment element 1508(A) relative to the alignment marking 1508(B) can indicate an alignment of the needle 1506 to the target location 1504. In this example, the user changes the position of the tip of the needle 1506 without changing the orientation of the needle 1506. As shown in FIGS. 15-1 through 15-3, as the position of the needle 1506 changes to align with the target trajectory 1530, the instrument alignment element 1508(A) moves within the alignment marking 1508(B). As such, although the interface generally provides both angular and positional error of the needle 1506 relative to the target trajectory 1528/1530, the user is using the interface to view positional error of the needle 1506 relative to the target trajectory 1530, since the user is changing the position without changing the orientation. Here, the user may use the needle 1506 to scan for the target location 1504.

As similarly discussed above in reference to FIGS. 14-1 through 14-3, the plane 1520 can be mapped to the interface to display the one or more interface elements 1508 at the appropriate position within the interface and/or relative to each other.

Figures 1, 2, 3, 16:
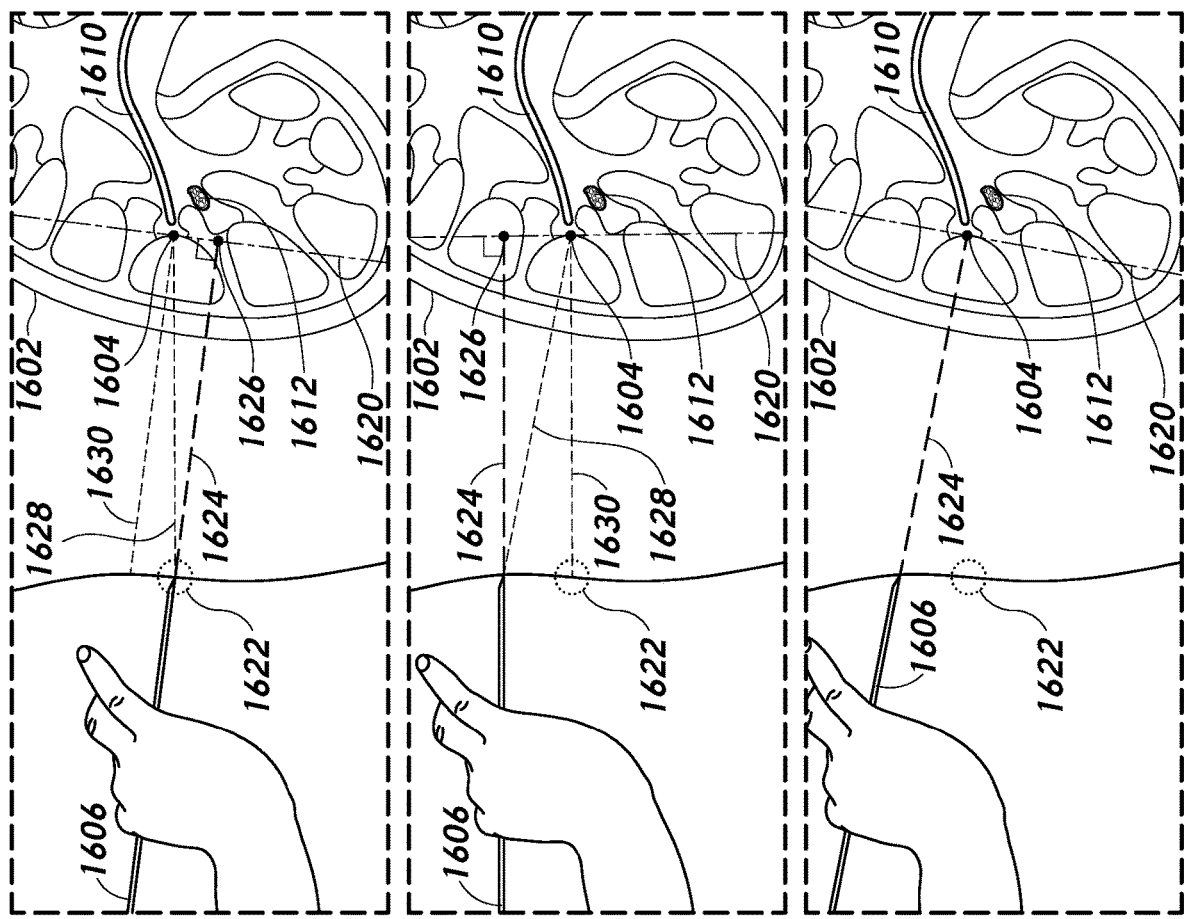

FIGS. 16-1 through 16-3 illustrate another example of mapping the pose of the needle 1606 onto a representation/plane 1620 that updates as the pose of the needle 1606 changes. In this example, the user changes the position of the tip of the needle 1606 and changes the orientation of the needle 1606. As shown in FIG. 16-1, the plane 1620 can be determined in a similar manner as that discussed in reference to FIGS. 14-1 through 14-3. In particular, the user can position the needle at an initial location 1622. The plane 1620 can then be determined such that a heading 1624 of the needle 1606 is normal to the plane 1620 and the plane 1620 includes the target location 1604. A projected position 1626 can be determined for the needle 1606 on the plane 1620 based on the current orientation/heading of the needle 1606.

As similarly discussed above in FIGS. 14-1 through 14-3, a target trajectory/pose for the needle 1606 can be determined to be/include (i) a line 1628 between a distal end of the needle 1606 and the target location 1604, and/or (ii) a line 1630 that is parallel to the pose of the needle 1606 and passes through the target location 1604. The target trajectory can update as the pose of the needle 1606 changes.

The projected position 1626 can be used to present the one or more interface elements 1608. For example, the position of the instrument alignment element 1608(A) relative to the alignment marking 1608(B) can indicate an alignment of the needle 1606 to the target location 1604. In this example, the user changes the position of the tip of the needle 1406 and changes the orientation of the needle 1606. As shown in FIGS. 16-1 through 16-3, as the position of the needle 1606 changes to align with the target trajectory 1628/1630, the instrument alignment element 1608(A) moves within the alignment marking 1608(B). As such, the user is generally using the interface to view both positional error and angular error of the needle 1406, since the user is changing the position and the orientation.

As similarly discussed above in reference to FIGS. 14-1 through 14-3, the plane 1620 can be mapped to the interface to display the one or more interface elements 1608 at the appropriate position within the interface and/or relative to each other.

Although various examples are discussed in the context of projecting a position of a needle onto a plane using the tip of the needle as a reference point, in some examples another portion of the needle can be projected onto a plane, such as a proximal end/tip of the needle, a middle portion of the needle, and so on. For example, in returning to the example of FIGS. 13-1, a proximal end of the needle 1306 can be projected onto the plane 1320 (instead of the tip of the needle 1306), such that the projected line includes the proximal end of the needle 1306 and is parallel to the target trajectory 1324. Here, the projected location of the proximal end of the needle 1306 on the plane 1320 would be above the target location 1304 (and the interface element 1308(A) would be located in the interface in the upper left corner in FIG. 13-1). In some embodiments, a projected position of a needle or another medical instrument on a plane can be determined using one or more projective geometry techniques. Further, although various 2D representations/planes are depicted, other types of representations can be implemented, such as 3D representations.

As discussed herein, various techniques can be used to determine a target plane. For example, a target plane can be based on a heading of a scope, such that the heading of the scope is normal to the plane. In some cases, the heading of the scope can also represent a target trajectory. As such, in some instances, this can assist a user in aligning a needle or other medical instrument to access a target site coaxially with a scope heading.

Example Coordinate Frames

As noted above, a medical instrument can be implemented to reach a target location. In some solutions of using a needle, a particular type of movement of the medical instrument may not be well defined, which may be due to the characteristics of the medical instrument (e.g., a cylindrical form of the needle), a type of sensor being used, and/or characteristics of a system tracking the pose of the medical instrument. As such, it may be difficult to correlate movement of the needle to movement of interface elements within an interface in an effective/intuitive manner. For instance, such solutions can cause a needle indicator to move up within an interface when a needle is tilted to the right relative to a user. This can disorient the user when viewing the interface to manipulate the needle.

Figure 17:
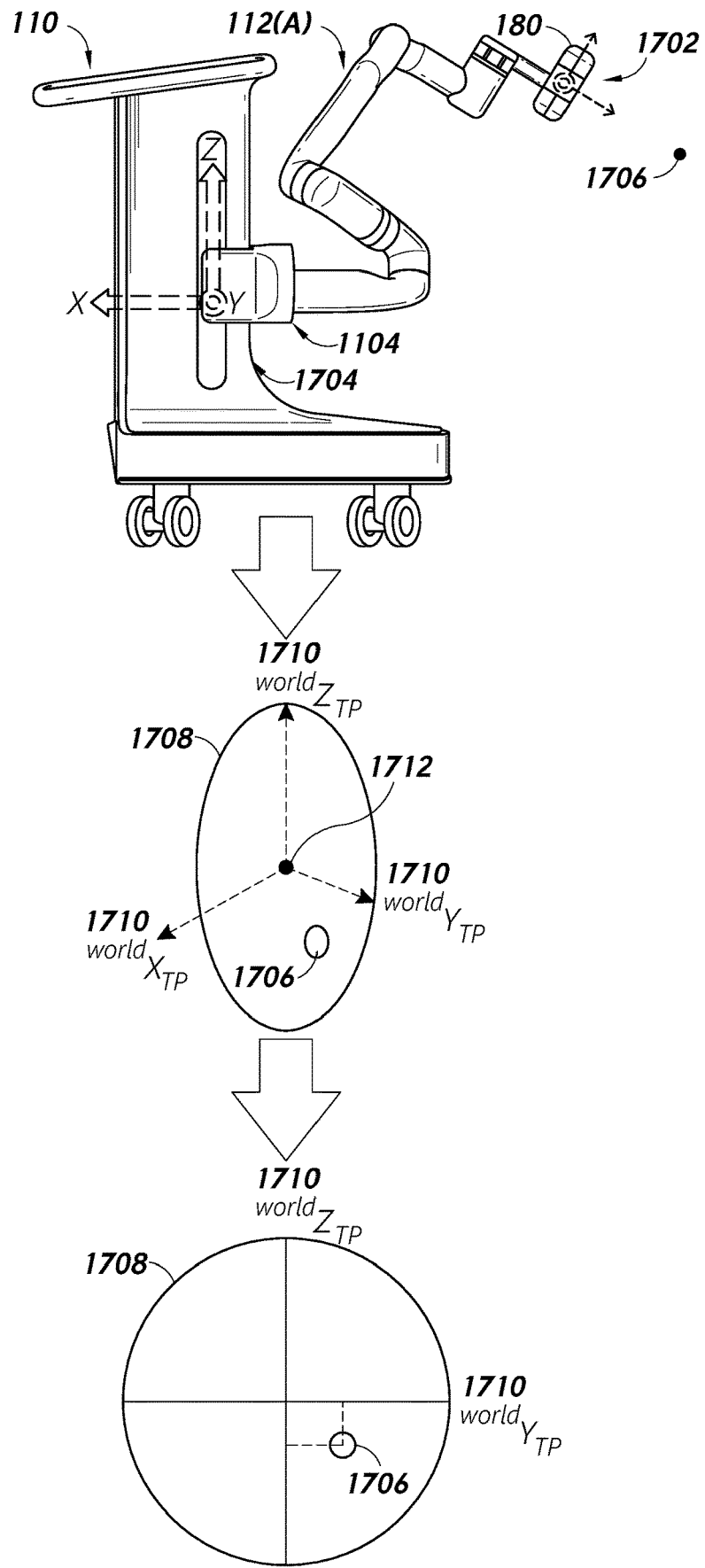
FIG. 17 illustrates example techniques for establishing one or more coordinate frames to correlate movement of a medical instrument to movement of an interface element within an interface in accordance with one or more embodiments.

FIG. 17 illustrates example techniques for establishing one or more coordinate frames to correlate movement of a medical instrument to movement of an interface element within an interface. In general, the techniques can use information about a robotic system to determine a coordinate frame for the medical instrument and use the coordinate frame for the medical instrument to provide information about an alignment/progress of the medical instrument. For example, the techniques can assist in achieving instinctive hand eye coordination by mapping medical instrument movement to a user interface in a manner that correlates to how the medical instrument is being held by a user (e.g., moving an interface icon for a needle left/right within an interface when tilting the needle left/right relative to the user, moving the interface icon up/down within the interface when tilting the needle up/down relative to the user, etc.). This can assist a user in aligning the medical instrument.

To illustrate, as noted above, a physician can implement the robotic system 110 to perform a medical procedure. The robotic system 110 can be coupled to the EM field generator 180, such as to the robotic arm 112(A). The EM field generator 180 can provide an EM field that is detected by an EM sensor on a medical instrument, such as a needle (not illustrated in FIG. 17). Based on the sensor data from the medical instrument, a pose of the medical instrument can be determined relative to a coordinate frame 1702 of the EM field generator 180. Further, a coordinate frame 1704 (also referred to as "the world coordinate frame 1704") can be determined for the robotic system 110, such as fixed to the carriage interface 1104/base of the robotic arm 112(A) or any other component of the robotic system 110. The pose of the medical instrument can then be represented within the world coordinate frame 1704. In examples, the pose of the medical instrument can be represented in the world coordinate frame 1704 based on a transformation (e.g., a homogeneous transformation) between the coordinate frame 1702 and the world frame 1704 using forward kinematics for the robotic system 110 (e.g., the robotic arm 112(A)).

Moreover, a target location 1706 within a patient (not illustrated) can be determined relative to the coordinate frame 1702 of the EM field generator 180 using any of the techniques discussed herein. A plane 1708 (also referred to as "the target plane 1708") can then be determined based on the target location 1706. The plane 1708 can then be represented within the world coordinate frame 1704, such as in a similar manner as the pose of the medical instrument is represented in the world coordinate frame 1704. Coordinate axes 1710 can then be determined for the target plane 1708. For example, an assumption/inference can be made that the medical instrument will not be parallel to the z-axis of the world coordinate frame 1704, which can be used to define a coordinate axis on the target plane 1708 (e.g., a y-axis). A cross product can be performed between the z-axis of the world coordinate frame 1704 and a heading (z-axis) of the medical instrument to define another coordinate axis on the target plane 1708 (e.g., a y-axis). Once two axes are defined, a third axis can be defined by performing a cross product between the newly obtained/determined axis and the heading of the medical instrument. FIG. 17 illustrates a 3D representation of the plane 1708 (the middle image) and a 2D representation of the plane 1708 (the bottom image). As shown, a projected location 1712 of the medical instrument is shown on the plane 1708 as the origin of the coordinate axes 1710. Further, the target location 1706 is represented with a bubble on the target plane 1706.

Once the coordinate frame 1710 is determined for the target plane 1708, a coordinate frame for the medical instrument can be determined. For example, the coordinate frame for the medical instrument can directly translate from the target plane 1708, since a heading of the medical instrument and the target plane normal can be mirror images of each other. As such, the coordinate frame for the medical instrument can be an inverse of the coordinate frame for the target plane 1708.

In examples, one or more of the following mathematical steps can be performed to generate one or more of the coordinate frames, axes, and/or other elements:

$$world_Z = [0,0,1]$$

$$world_{X_{TP}} = world_{R_{needle}}[0:2,2]$$

$$world_{Y_{TP}} = world_Z \times world_{X_{TP}}$$

$$\text{world}_{Z_{TP}} = \text{world}_{X_{TP}} \times \text{world}_{Y_{TP}}$$

$$^{world}R_{TP} = [^{world}X_{TP}, {}^{world}Y_{TP}, {}^{world}Z_{TP}]$$

$$^{world}t_{TP} = {}^{world}P_{target}$$

$$[^{BE}P_{bubble}, 1] = (^{world}T_{TP})^{-1}[^{world}P_{bubble}, 1]$$

$$\text{If } {}^{world}R_{needle}[0:2,2] = {}^{world}Z \rightarrow {}^{world}Z_{+} = eps$$

Example Adaptive Targeting

Figures 1B, 18:
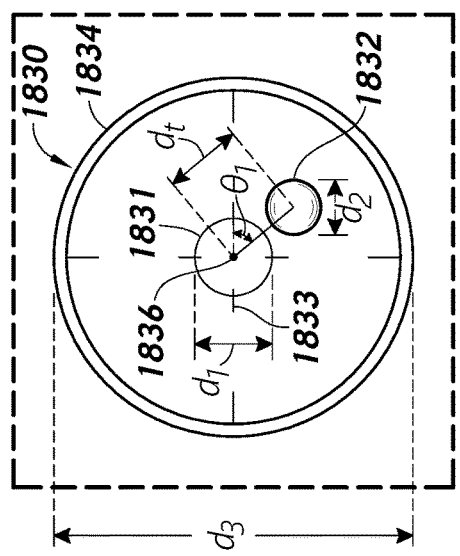
FIGS. 18-1A, 18-1B, 18-2A, and 18-2B illustrate example adaptive targeting techniques for an interface in accordance with one or more embodiments.
Figures 3, 19:
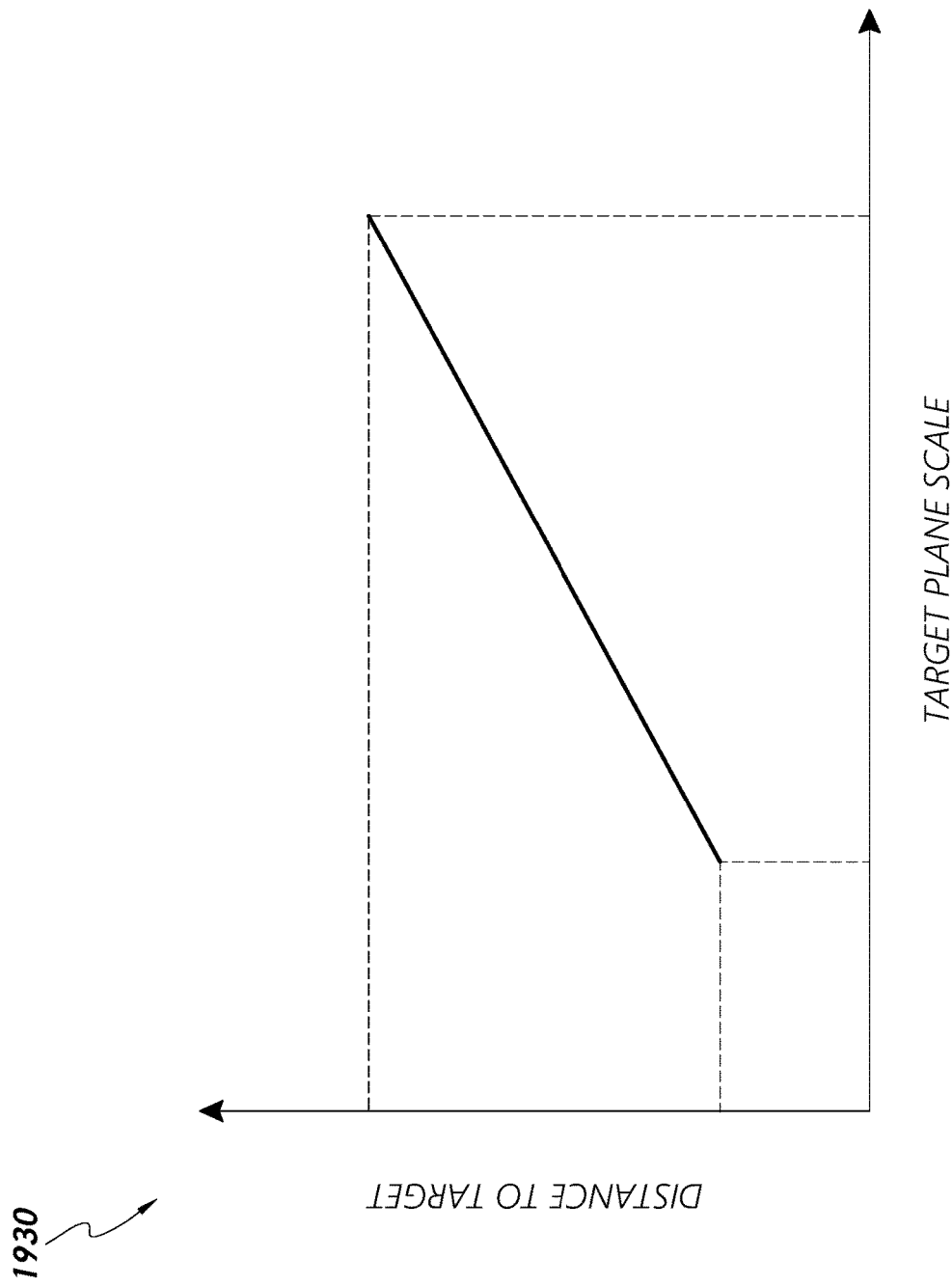

FIGS. 18 and 19 illustrate various example adaptive targeting techniques (also referred to as "adaptive scaling") in accordance with one or more embodiments. In some embodiments, when a medical instrument is relatively far away from a target location (e.g., outside a threshold), some amount of targeting error can be tolerated. However, as the medical instrument moves closer to the target location, a targeting error may need to be smaller (e.g., a size of an anatomical target (such as a size of a papilla), smaller than a size of the anatomical target, or another size) to facilitate access to the target location. As such, in examples, the adaptive targeting techniques can be implemented such that one or more interface features within an interface can function in different manners as a medical instrument moves closer to (or farther away from) a target location (e.g., as the medical instrument is inserted). For instance, when a medical instrument tip is positioned relatively close to a target location, relatively slight deviations from a target trajectory may result in relatively greater movement of an instrument position feature from a target center in the interface, in comparison to when the medical instrument is farther away from the target location. This can assist a physician in aligning the medical instrument with the target location with a greater amount of tolerance when the medical instrument is farther from the target location, and/or assist the physician in more precisely aligning the medical instrument with the target location as the medical instrument approaches the target location.

FIG. 18-1 shows a user holding or otherwise maintaining a needle 1820 in a certain pose 1821, wherein the needle 1820 is oriented at a certain axial orientation associated with the pose 1821. Image 1824 of FIG. 18-1A relates to a medical procedure in which a user inserts the needle 1820 in an attempt to advance the tip of the needle 1820 through a renal pyramid 1825 to a target location 1826 (e.g., a calyx puncture location). For example, as described in detail herein, control circuitry of the relevant system may be configured to determine a target needle trajectory 1822 based on the current position 1828 of the needle tip and/or orientation of the needle 1820. In examples, the target trajectory 1822 may be associated with a direct (or indirect/tortuous) path between the needle tip position 1828 and the target location 1826, as shown. Therefore, ideal implementation of the relevant medical procedure may involve the user inserting the needle 1820 to the target location 1826 in a manner as to deviate as little as possible from the target needle trajectory 1822.

FIG. 18-1B shows certain user interface features that may be implemented in connection with a medical procedure as described herein. For example, control circuitry of the relevant system may be configured to generate interface data representing certain visual features as shown and described herein, wherein certain characteristics of such feature(s) are determined and/or based at least in part on detected needle position(s), determined needle target needle trajectory(s), determined target location(s), and/or other information derived using one or more position sensors or other position determination means/mechanism(s).

The user interface features shown in FIG. 18-1B can include an alignment visualization element 1830 including certain features that may be dynamically adjusted with respect to one or more characteristics thereof in response to changes in needle position, trajectory, and/or the like. In the illustrated example of FIG. 18-1B, the alignment visualization element 1830 includes an instrument position feature 1832 (also referred to as "the instrument-alignment element 1832"), which may have a bubble-type shape or form, or any other shape or form. For example, the instrument position feature 1832 may be configured to visually evoke imagery similar to a bubble level or other leveling instrumentation. The alignment visualization element 1830 may further include an alignment target feature 1831 (also referred to as "the alignment marking 1831"), which may be represented as a shape or form defining a boundary around a central target position 1836, which may generally be associated with an axial center of the alignment visualization element 1830 and/or one or more features thereof. Although illustrated as a full circular boundary, the alignment target feature 1831 may be a broken circle or any other shape or form visually indicating a radial boundary around the target center 1836.

In some embodiments, the alignment visualization element 1830 further includes one or more crosshair features 1833, which may serve to indicate to the user and/or direct the user visually to the target center 1836. In examples, the crosshair features 1833 intersect at the target center 1836. In some embodiments, the alignment visualization element 1830 further includes an outer boundary feature 1834 (also referred to as "the boundary marking 1834"), wherein the outer boundary or may provide a visual and/or enforced boundary for the instrument position feature 1832. The control circuitry may be configured to limit radial distance of the instrument position feature 1832 from the target center 1836 to the outer or inner bounds of the outer boundary feature 1834. However, in some implementations, the instrument position feature 1832 may be permitted to stray outside the outer boundary 1834, wherein the outer boundary provides a visual indication to the user relating to the degree to which the instrument position feature 1832 has departed from the target center 1836 and/or alignment target boundary 1831.

According to some implementations of the present disclosure, the instrument position feature 1832 may be presented a distance $d_t$ from the target center 1836 that is based on and/or representative of a distance $D_P$ between a determined needle projection point 1829 lying in a plane 1827 that intersects the target location 1826. For example, the plane 1827 may be a target entry plane that is substantially orthogonal to the heading/pose of the needle 1820. However, it should be understood, that the distance $D_P$ between the projected position 1829 and the target location 1826 may be with respect to any plane intersecting the target location 1826. The projected needle position 1829 may represent a location/position projected for the tip of the needle 1820 if the needle 1820 is inserted along the current trajectory 1823 until it intersects target plane 1827. However, it should be understood that aspects of the present disclosure relating to projected deviation distances from a target location may represent any projected distance of a needle or other instrument from a target location. With reference to FIG. 18-1B, the distance $d_t$ between the instrument position feature 1832 and the target center 1836 may be based at least in part on the projected deviation distance $D_P$.

In connection with some embodiments disclosed herein, such as with reference to FIG. 18-1B and/or other figures of the present disclosure, reference is made to the distance $d_t$ between an instrument position feature 1832 and a target center with respect to an alignment visualization element of a user interface. It should be understood that the distance $d_t$ may be interpreted/represented as a relative dimension relative to the size of one or more other visual features of the alignment visualization element 1830. That is, where changes in the distance $d_t$ between an instrument position feature and a target center 1836 are described herein, it should be understood that such referenced distances may refer to changes in actual distance as represented on a user interface display, and/or may refer to changes in a distance between the instrument position feature 1832 and the target center 1836 relative to dimension(s) of one or more other visual features of the alignment visualization element 1830. For example, a change in distance $d_t$ between the instrument position feature 1832 and the target center 1836 may be visually represented by changing the actual distance $d_t$ between the instrument position feature 1832 and the target center 1836 and/or by changing dimensions associated with one or more of the features of the alignment visualization element 1830, such as the diameter/dimension $d_1$ of the alignment target feature 1831, the diameter/dimension $d_2$ of the instrument position feature 1832, the diameter/dimension $d_3$ of the outer boundary feature 1834, and/or the length and/or position of the crosshair feature(s) 1833. Therefore, a description herein of change/alteration of the distance between an instrument position feature and a target center of an alignment visualization user interface element can be understood to include changing the distance $d_t$ between the instrument position feature 1832 and the target center 1836, and/or shrinking or enlarging any of the other dimensions shown in FIG. 18-1B, such as in a proportional manner.

Figures 2B, 18:
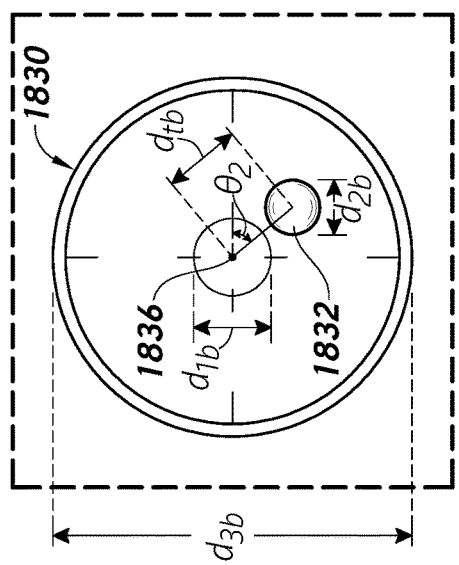
Figures 1A, 18:
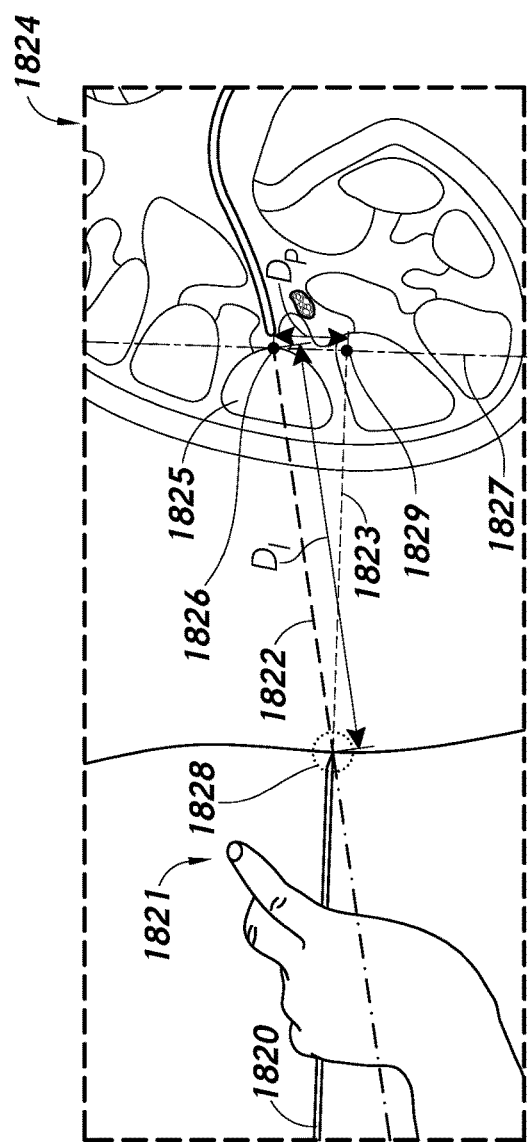
Figures 2A, 18:
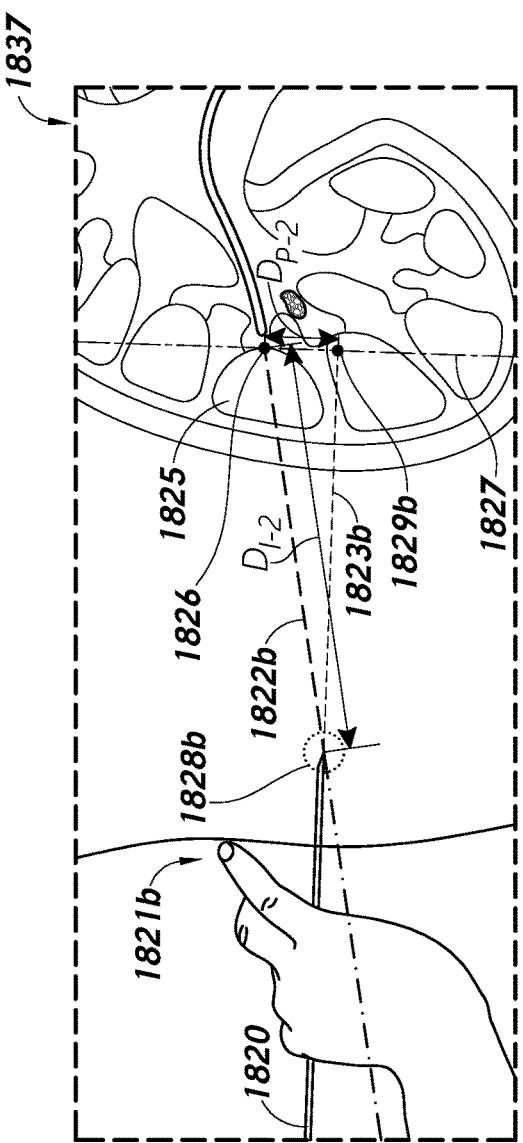

FIG. 18-2A shows the user holding the needle 1820 at an altered position/pose 1821b. For example, image 1837 of FIG. 18-2A may represent the needle 1821 in a pose 1821b that is associated with further insertion of the needle 1820 toward the target location 1826. That is, in FIG. 18-2A, the distance $D_{I-2}$ between the needle point position 1828b and the target location 1826 may be shorter than the distance $D_I$ shown in FIG. 18-1A. FIG. 18-2B shows a modified version of the alignment visualization element 1830, wherein the distance $d_{tb}$ of the instrument position feature 1832 has been modified to represent the current position/pose 1821b of the needle 1820.

As shown in FIG. 18-2A, control circuitry can determine a target needle trajectory 1822b and/or a current insertion distance $D_{I-2}$ between the needle tip position 1828b and the target location 1826. The control circuitry may be configured to determine a target deviation distance $D_{P-2}$, that represents a current projected deviation between the projected needle position 1829b and the target location 1826.

With respect to the image of FIG. 18-2B, in some examples the alignment visualization element 1830 may be configured to present the instrument position feature 1832 at a distance $d_{tb}$ from the central target position 1836, wherein such distance $d_{tb}$ can be based at least in part on the current projected deviation distance $D_{P-2}$. In some implementations, the distance $d_{tb}$ may have a relationship to the distance $d_t$ of FIG. 18-1B that is proportional to the difference between the projected deviation distance $D_{P-2}$ relative to the projected deviation distance $D_P$. That is, the change in distance of the instrument position feature 1832 from the target center 1836 may be generally linear with respect to the change in projected deviation distance between the pose 1821 and the pose 1821b.

In some implementations, the change in distance of the instrument position feature 1832 from the target center 1836 may be generally nonlinear with respect to the change in projected deviation distance between the pose 1821 and the pose 1821b. For example, the degree to which changes in projected deviation distance cause changes in distance between the instrument position feature 1832 and the target center 1836 can be based at least in part on the insertion distance $D_I/D_{I-2}$. That is, when determining the distance $d_t/d_{tb}$, control circuitry may make such determinations based on the distance $D_I/D_{I-2}$, at least in part. For example, the distance $d_{tb}$ may be determined based on a product of projected deviation distance $D_{P-2}$ and the insertion distance $D_{I-2}$, among possibly other multiplier(s). In some implementations, such instrument position feature distance $d_{tb}$ determination may be performed by control circuitry using one or more insertion distance parameters. For example, such parameter(s) may have a greater value (e.g., results in a greater increase/decrease on instrument position feature distance) for relatively shorter insertion distances. That is, the insertion distance parameter(s) may have a generally inverse relationship with insertion distance, such that the parameter(s) has/have a greater effect on the instrument position feature distance $d_t$ determination as the insertion distance decreases. Here, when the user inserts the needle tip to a position that is relatively close to the target location 1826, relatively slight deviations from the target needle trajectory may result in relatively greater movement of the instrument position feature 1832 from the target center 1836. It should be understood that the various distances shown in FIGS. 18-1A and 18-2A may be direct vector distances or may be vector component dimensions/distances with respect to any suitable or desirable reference plane or axis.

In some examples, the instrument position feature 1832 is presented within the alignment visualization element 1830 without being presented outside of such element 1830. For instances, dimensions represented by the alignment visualization element 1830 can change linearly as a function of distance between the needle 1820 and the target location 1826, wherein the position of the instrument position feature 1832 can be positioned within the alignment visualization element 1830 even for relatively large alignment error. To illustrate, a position of the instrument position feature 1832 can be the same for different distances when the alignment error is relatively large, since the instrument position feature 1832 is displayed only within the alignment visualization element 1830 (in some instances) and cropped if it would be positioned outside of the alignment visualization element 1830. As such, in some instances, as the needle 1820 moves closer to the target location 1826, the physical representation associated with the alignment visualization element 1830 becomes smaller, even though the alignment visualization element 1830 looks the same. In examples, the user interface (e.g., alignment visualization element 1830 and/or other elements) do not change. An error or distance in pixel space can correspond to smaller error as the needle 1820 moves closer to the target location 1826. To illustrate, a 2 mm error of the needle 1820 to a target trajectory may not be noticeable when the needle 1820 is relatively far from the target location 1826, but become noticeable as the needle 1820 moves closer to the target location 1826.

FIGS. 19-1 through 19-3 illustrate example techniques of scaling a target plane based on an insertion distance of a medical instrument. In FIGS. 19-1 and 19-2, images 1902 and 1904 on the left depict anatomy of a patient (including a kidney 1906), as well as a target location 1908 and a pose of a needle 1910. Further, images 1912 and 1914 in the middle depict target representations on a plane 1916 (also referred to as "the target plane 1916") (e.g., that correspond to physical dimensions that scale with distance to a target). The target plane 1916 can be associated with/include a circle with a defined diameter, wherein the circle can be centered on the target location 1908. The images 1912 and 1914 are generally not presented to a user, but are provided here for ease of discussion. Moreover, images 1918 and 120 on the right depict one or more interface elements 1922 (e.g., that correspond to fixed user interface dimensions) to indicate a current pose of the needle 1910. The interface element 1922(A) can represent the needle 1910, the interface element 1922(B) can represent the target location 1908, and the interface element 1922(C) can represent a boundary. FIGS. 19-1 and 19-2 also illustrate a scope 1924 to assist in removing a kidney stone 1926.

As shown in FIG. 19-1, when the tip of the needle 1910 is farther from the target location 1908, the target representation on the target plane 1916 can be relatively large. The target representation can represent the one or more interface elements 1922 (e.g., dimensions of the one or more interface elements 1922). For ease of discussion, the target representation is illustrated as being associated/projected onto the target plane 1916; however, the features of the target representation can be implemented in other manners without associating/projecting the target representation onto the target plane 1916.

As shown in FIG. 19-2, as the tip of the needle 1910 moves closer to the target location 1908, the target representation can change in size, as illustrated in the image 1914. For example, one or more dimensions of the target representation on the target plane 1916 can be reduced, such that a smaller area on the target plane 1916 corresponds to the one or more interface elements 1922. As such, a scaling ratio of dimensions represented in the target plane 1916 to dimensions represented in the interface can be adjusted. In some embodiments, a center element 1928 of the target representation can change to be the same as or smaller than a size of an anatomical target, such as a size of a papilla. For example, when the tip of the needle 1910 is with a threshold distance to the target location 1908, the center element 1928 can be updated to be the same size as (or smaller than) the anatomical target.

FIG. 19-3 illustrates an example graph 1930 of a scale of the target plane 1916 relative to a distance of the needle 1910 to the target location 1908 (e.g., the insertion distance). In particular, the y-axis represents the distance between the tip of the needle 1910 and the target location 1908, while the x-axis represents the size of the target representation on the target plane 1916 (i.e., the scaling ratio of distances on the target plane 1916 to distances on the interface). As shown, as the needle 1910 moves closer to the target location 1908, the relationship between a distance on the target plane 1916 and a corresponding distance in the interface (e.g., a scaling ratio) can be updated. Although a linear relationship is illustrated in FIG. 19-3, another type of relationship can be implemented (e.g., non-linear, step, etc.).

In some instances, the scaling techniques discussed in the context of FIGS. 19-1 through 19-3 (and elsewhere herein) can implement adaptive targeting to assist a user in accurately inserting the needle 1910 to reach the target location 1908 (which may be relatively small). For example, such scaling techniques can cause relatively slight deviations from a target trajectory to result in smaller movement of an instrument position feature from a target center in an interface when the needle 1910 is farther from a target location, and cause relatively slight deviations from the target trajectory to result in relatively greater movement of the instrument position feature from the target center when the needle 1910 is positioned relatively close to the target location. In examples, dimension(s) of the one or more interface elements 1922 may not change within an interface as the needle 1910 is inserted (e.g., each interface elements 1922 can maintain the same size/shape). However, in other examples, dimension(s) of the one or more interface elements 1922 may change within the interface.

In some embodiments, one or more of the techniques discussed herein can reduce complexity of percutaneously accessing a target location, such as by providing an interface that includes elements to indicate an alignment/position of a medical instrument relative to a target trajectory and/or a target location. In examples, the interface can assist a physician or other user in manually manipulating the medical instrument. Such techniques can enhance the ability of the physician or another user in accurately reaching a target location with the medical instrument, in comparison to other techniques, such as fluoroscopy or ultrasound.

Example Anatomical Visualization

Figure 20:
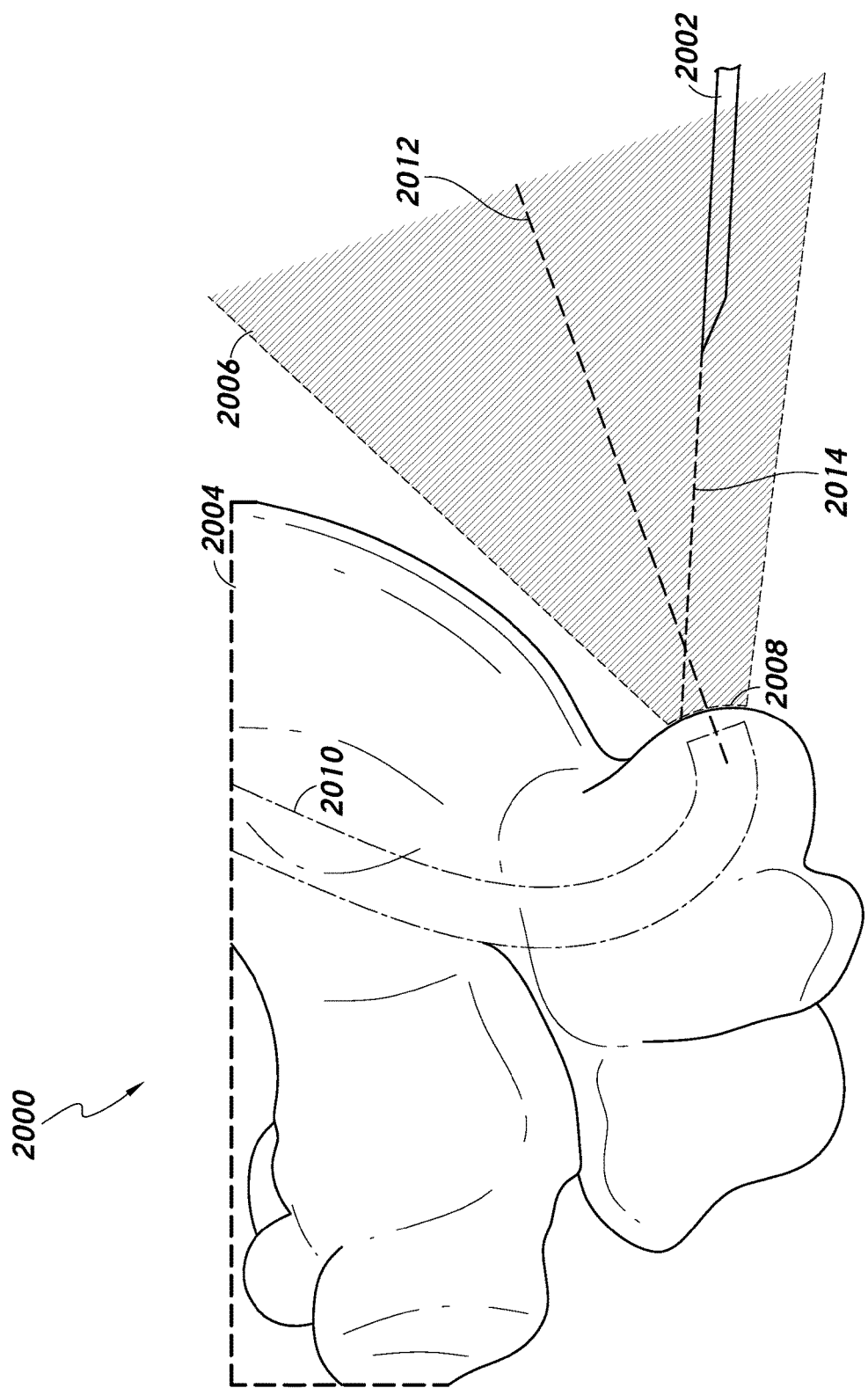
FIG. 20 illustrates an example anatomical visualization that can be provided via an interface to assist a user in navigating a medical instrument in accordance with one or more embodiments.

FIG. 20 illustrates an example anatomical visualization 2000 that can be provided via an interface to assist a user in navigating a medical instrument in accordance with one or more embodiments. In this example, the medical instrument is implemented as a needle; however, the medical instrument can be implemented as other instruments. In some instances, the visualization 2000 can assist a user in aligning the needle with the appropriate orientation to access a target location coaxially, such as coaxially aligned with a renal pyramid/papilla, which can avoid damaging surrounding anatomy (e.g., which can occur due to overshoot of the needle) and/or provide more flexibility for an instrument that is inserted into the access path (e.g., a catheter or another instrument).

As shown, the visualization 2000 includes a needle representation 2002 of the needle and an anatomical representation 2004 of anatomy of a patient, such as a calyx network and/or other anatomy associated with the patient. The anatomical representation 2004 can be presented as a 2D or 3D representation within an interface, such as any of the interfaces discussed herein. The visualization 2000 also includes a target region representation 2006 representing a target region that the needle should stay within to reach a target location (represented with a target location representation 2008). The target region representation 2006 can be presented as a 2D or 3D representation, such as a 2D cone (as shown), a 3D cone, and so on. The target location and target region can be determined based on an orientation/position of a scope and or another element (represented with an element 2010 in the visualization 200). In this example, the target region is aligned with a distal end of the scope, which is positioned within the kidney to designate the target location, such that a line 2012 that is normal to the distal end of the scope (e.g., a line representing a heading of the scope) runs through a center of the target region and target location. The line 2012 may represent a target trajectory in some instances, which may or may not be presented in the visualization 2000. In examples, as the scope moves, the target region representation 2006 and/or the target location representation 2008 can be updated to maintain alignment with the distal end of the scope. The target location representation 2008 can be presented as a 2D or 3D representation, such as a 2D line (as shown), a 3D sphere/surface, and so on. In examples, the target location representation 2008 is associated with an anatomical target (e.g., scaled to/represents a size of a papilla, which can be 4 or 6 mm). Further, the visualization 2000 can includes a line 2014 representing a heading of the needle.

Although various elements are discussed in the context of visualizations, in some instances such elements may not be presented, but may merely be determined/generated for use in evaluating a current pose of the needle 2000 relative to the target location 2008. For example, the target region and/or an anatomical representation/model may be determined and used to evaluate a current pose of the needle without displaying the target region visualization 2006 and/or the anatomical representation 2004.

Example Instrument States and Regions

Figure 21:
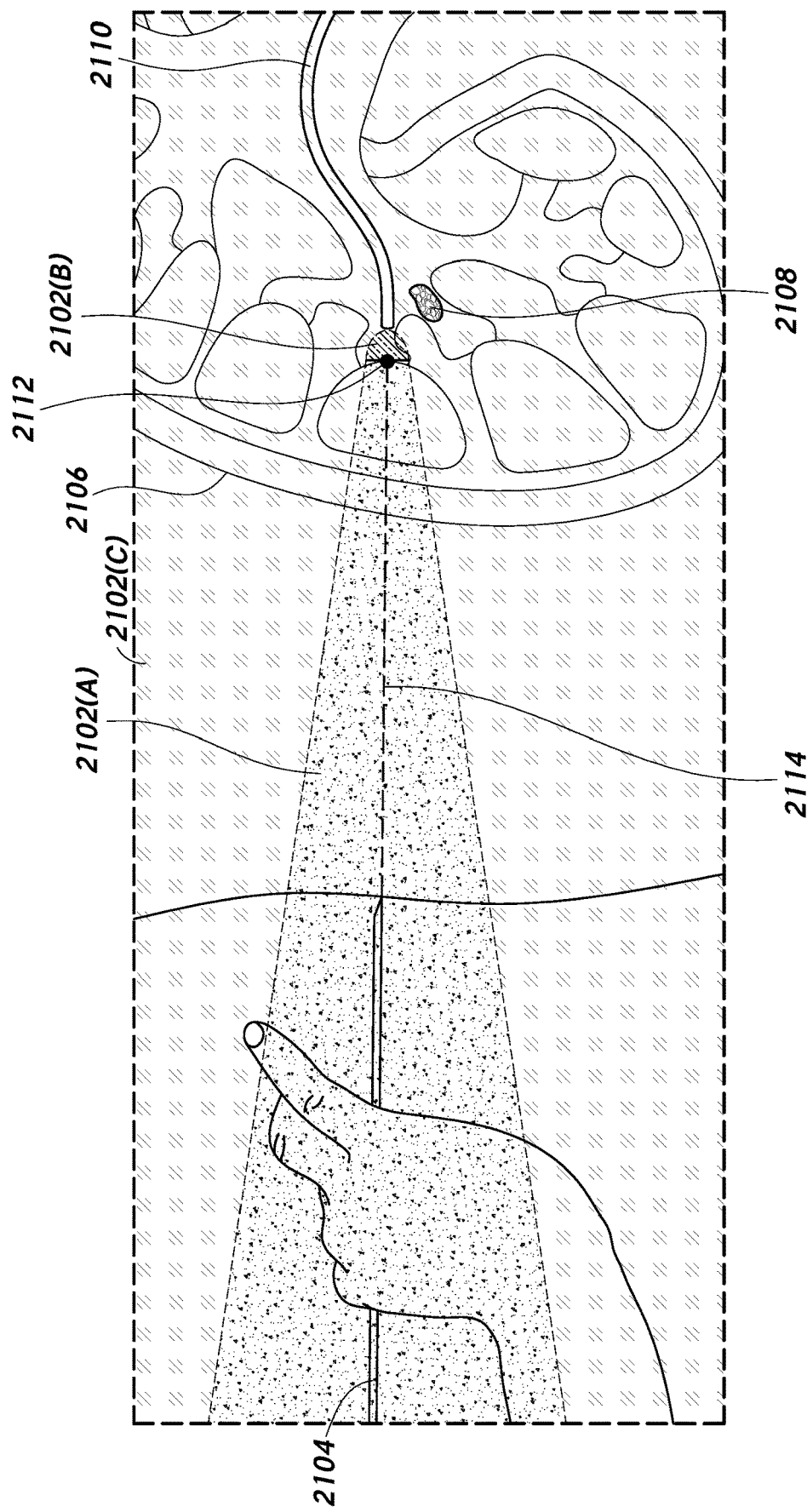
FIG. 21 illustrates example regions that can be implemented/generated to determine a state of a medical instrument in accordance with one or more embodiments.

FIG. 21 illustrates example regions 2102 that can be implemented/generated to determine a state (sometimes referred to as "a progress state") of a medical instrument in accordance with one or more embodiments. As shown, the regions 2102 are discussed in the context of a needle 2104 accessing a kidney 2106 to assist in removal of a kidney stone 2108. Here, a scope 2110 is implemented to designate a target location 2112 for percutaneous access by the needle 2104. However, the regions 2102 can be implemented in the context of other situations/medical procedures. In examples, a state of the needle 2104 can indicate a location/progress of the needle 2104 relative to the target location 2112. For example, a state can include: an in-progress state indicating that the needle 2104 is being inserted and has not yet reached/passed the target location 2112, an in-progress and aligned state indicating that the needle 2104 is being inserted and is aligned with a target trajectory/pose, a target-unreachable state indicating that the target location 2112 is unreachable given the current orientation of the needle 2104, a target-reached state indicating that the needle 2104 has reached the target location 2112, a target-passed state indicating that the needle 2104 has been inserted beyond the target location 2112, and so on. A state of the needle 2104 can be used for a variety of purposes, such as to provide an indication via an interface and/or perform other processing.

In some embodiments, the regions 2102 are determined based on the target location 2112 and/or a position/orientation of the scope 2110. For example, a first region 2102(A) can be determined based on a target plane and/or a position/orientation of the scope 2110. Here, the region 2102(A) includes a cone shaped region that is aligned with a line 2114 that is normal to a distal end of the scope 2110. However, the region 2102(A) can include other forms/shapes. In this example, the needle 2104 is also aligned with the line 2114. The region 2102(A) can be associated with a state in which it is possible to reach the target location 2112 (e.g., an in-progress state, an in-progress and aligned state, etc.). For example, when the needle 2104 is positioned within the region 2102(A) (e.g., relative to the tip of the needle 2104 and/or any other portion), an indication can be provided via an interface indicating that it is possible to align the needle 2104 with the target location 2112. Moreover, if the needle is aligned with the line 2114 (e.g., a target pose/trajectory), the needle 2104 can be associated with a state indicating that the needle 2104 is aligned with the target location 2112 (e.g., an in-progress and aligned state). In examples, when the needle 2104 is positioned within the region 2102(A), a progress indicator can indicate the proximity of the needle 2104 relative to the target location 2112 and/or can indicate that the needle 2104 is in progress of being inserted.

Further, a second region 2102(B) can align with and extend from a distal end of the scope 2110. Here, the region 2102(B) includes a particular form; namely, a semicircle with a straight line that aligns with a target plane (partially illustrated in FIG. 21). However, the region 2102(B) can include other forms/shapes. The region 2102(B) can be associated with a state in which that the target location 2112 is reached. For example, when the tip of the needle 2104 is located within the region 2102(B), it can be determined that the target location 2112 is reached. In examples, an indication can be displayed via an interface indicating such state. In one illustration, a progress indicator can be displayed that indicates that the needle 2104 has reached the target location 2112. In examples, the region 2102(B) can allow for some amount of overshoot of the target location 2112. Further, in examples, a dimensions and shape of the region 2102(B) can be determined based on a dimension and/or shape of human anatomy associated with the target location, such as an average size of a papilla (with an amount of tolerance), a size/shape of another organ/anatomical feature, and so on. In examples, the region 2102(A) and/or 2102(B) represent a target region (e.g., a region that the needle 2104 should stay within to reach the target location 2112).

Moreover, as also shown in FIG. 21, the third region 2102(C) can encompass an area outside of the first and second regions 2102(A), 2102(B). The region 2102(C) can be associated with a state in which the target location 2112 is unreachable, the target location 2112 has been passed, or that the needle 2104 is otherwise not located with the target region. For example, when the tip of the needle 2104 is located within the region 2102(C), it can be determined that the target location 2112 is unreachable given the current pose of the needle 2104, that the target location 2112 has been passed (e.g., the needle 2104 has substantially overshot the target location 2112), or that the needle 2104 is otherwise not located with the target region. In examples, an indication can be displayed via an interface indicating such state. This can indicate that a physician should stop inserting and/or retract the needle 2104, as the physician may not be able to correct the needle trajectory at this point and/or the physician has overshot the target location 2112 by a particular amount. In one illustration, if the needle 2104 crosses over into the region 2102(C), an instrument-alignment element can be displayed in a deformed state and/or another indication can be provided.

Example Adaptive Progress Indication

As discussed in various examples herein, a proximity/progress of a medical instrument to a target location can be indicated in a user interface or otherwise. In some embodiments, such information is indicated in a linear manner, such that an amount of progress indicated for a unit of movement closer/farther from the target location can consistently be represented by a particular amount of progress change. To illustrate, each 10 mm change in a distance between a tip of a medical instrument and a target location can correspond to a 5% progress change that is displayed within an interface (e.g., to indicate a progress of inserting the medical instrument to the target location). Here, such progress change can be implemented for each 10 mm change until the medical instrument reaches the target location.

In other embodiments, one or more adaptive progress indication techniques can be performed to adjust an amount of progress that is indicated for a unit of movement. In one illustration, as shown in the graph 2200 of FIG. 22, an amount of progress change indicated for a unit of position change can be based on a distance between a medical instrument and a target location. In this illustration, an insertion distance within a range of 150 mm to 75 mm can be associated with a non-linear progress indication. For instance, each 1 mm change in a proximity to the target location within the 150 mm to 75 mm range can cause an increasing amount of progress to be indicated (e.g., a change from 150 mm to 140 mm can be associated with a 1% change in progress, a change from 140 mm to 130 mm can be associated with a 2% change in progress, etc.). Further, in this illustration, progress change can become linear for changes from 75 mm to and/or past the target location. By implementing such adaptive techniques, progress change within an interface can be minimal when the medical instrument is relatively far from the target location, which may allow a physician to reposition or otherwise select an insertion site without seeing much progress change. Moreover, this can cause the physician to slow down the insertion as the medical instrument approaches the target location, thereby achieving a more accurate needle alignment before reaching the target location.

Figure 22:
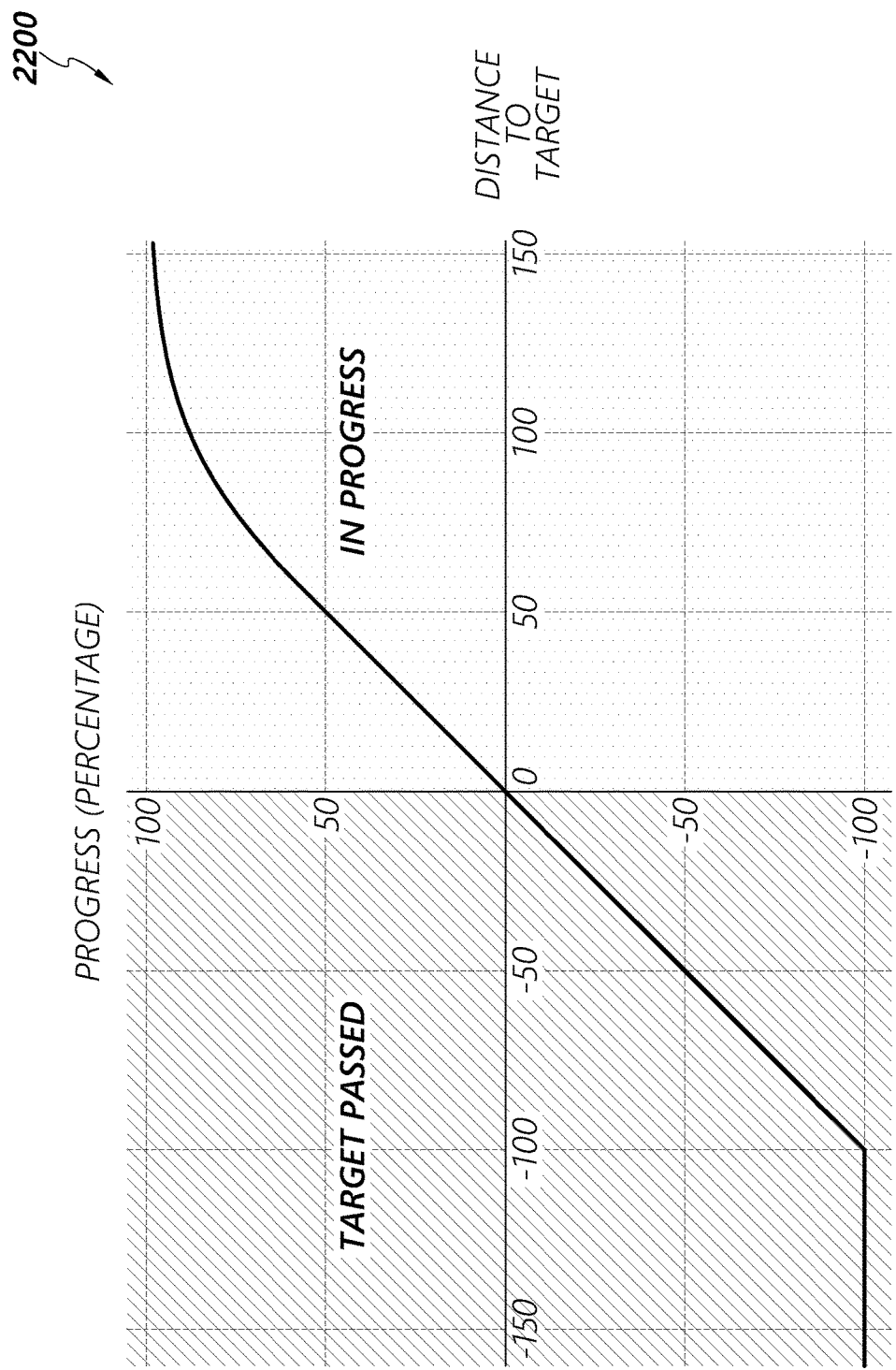
FIG. 22 illustrates an example graph of a progress percentage relative to a distance of a medical instrument to a target location in accordance with one or more embodiments.

FIG. 22 and the above illustration describe one of many example techniques for adaptive progress indication. As such, other linear or non-linear progress indications can be implemented, such as a piecewise linear function, exponential function, and so on.

Although various techniques are discussed herein to determine/present progress/alignment information, a variety of other techniques can be used in addition to or alternatively from such techniques. In some embodiments, a scope can be positioned within proximity to a target location, such as parked in front of a papilla of interest. Here, an image captured by the scope can be presented through an interface to provide a visual confirmation that a target location has been reached, such as in the case when anatomical motion is minimal and/or the scope is parked with the appropriate field of view. In examples, the image from the scope can be analyzed to determine a progress state of a medical instrument. Further, in some embodiments, any of the progress information discussed herein can be presented in addition to or alternatively from the image captured by the scope to assist in confirming that the target location has been reached. Such progress information can be particularly useful when there is substantial anatomical motion, the papilla or other anatomy is pressed against a camera of the scope, and so on. In examples, such progress information can augment images obtained by a scope. Furthermore, such progress information can avoid navigating the scope around to search within the kidneys to confirm if a medical instrument has been inserted into the kidneys. Additionally or alternatively, in some embodiments, a current position of a medical instrument, such as a needle, can be overlaid on an image view of a scope. Additionally or alternatively, in some embodiments a medical instrument can be equipped with an impedance-sensing-electrodes and an impedance signal can be used to classify which medium the medical instrument electrodes are in contact with. In examples, if the impedance signal is classified as urine, it can be determined that the target is reached (e.g., the target-reached state can be determined).

Example Flow Diagrams

FIGS. 23-28 illustrate example flow diagrams of processes for performing one or more techniques discussed herein. The various operations/blocks associated with the processes can be performed by control circuitry implemented in any of the devices/systems discussed herein, or a combination thereof, such as the control system 140, the robotic system 110, the table 150, the EM field generator 180, the scope 120, and/or the needle 170.

Figure 23:
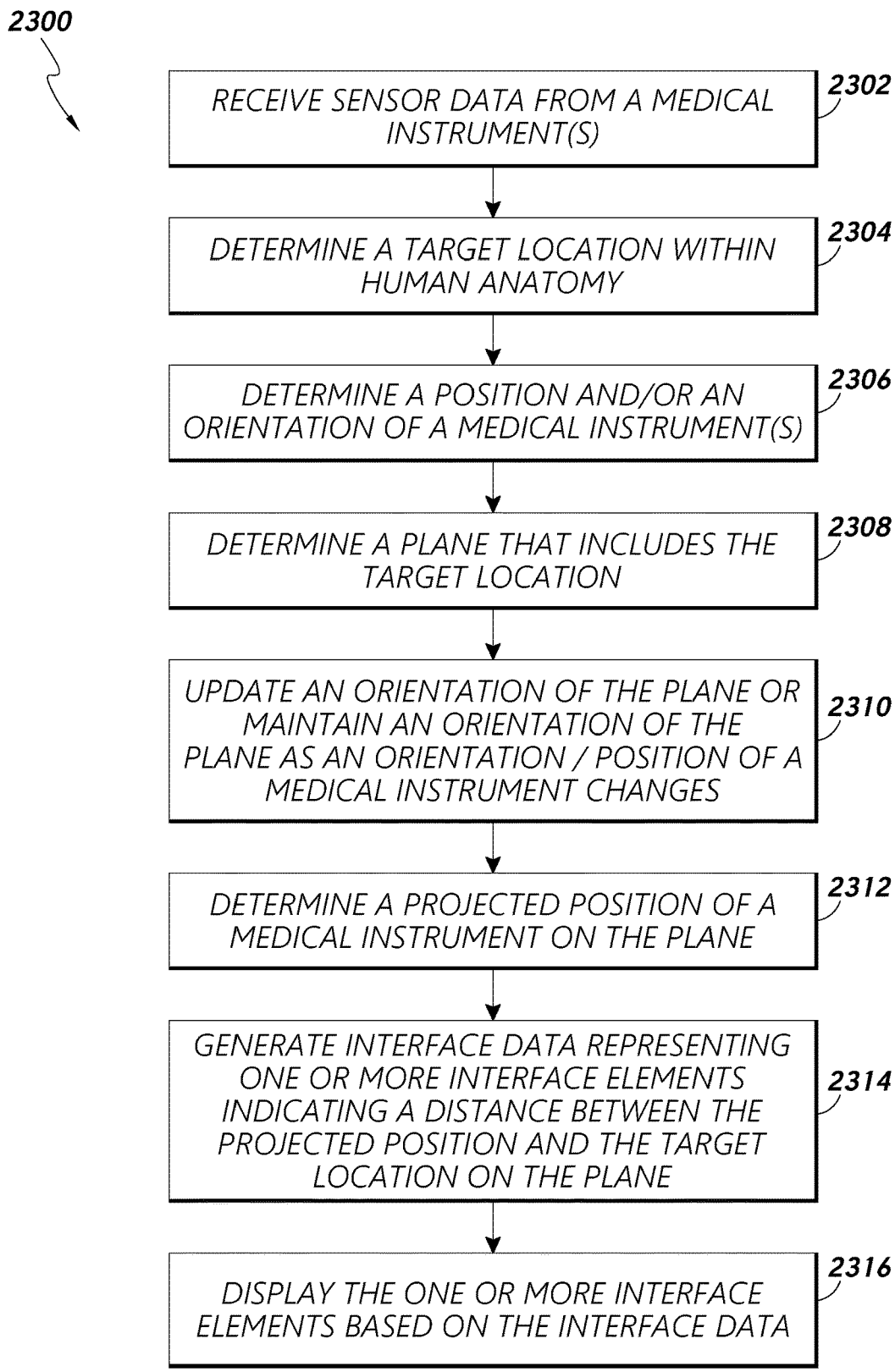
FIG. 23 illustrates an example flow diagram of a process for generating data indicating a distance between a projected position of a medical instrument on a plane and a target location on the plane in accordance with one or more embodiments.

FIG. 23 illustrates an example flow diagram of a process 2300 for generating data indicating a distance between a projected position of a medical instrument on a plane and a target location on the plane in accordance with one or more embodiments.

At block 2302, the process 2300 can include receiving sensor data from one or more medical instruments. For example, according to certain use cases, control circuitry of a device/system, such as a control system, can receive sensor data via a communication interface from one or more medical instruments, such as a scope, a needle, or any other medical instrument. The sensor data can be indicative of and/or used to determine a position and/or an orientation of the one or more medical instruments.

At block 2304, the process 2300 can include determining a target location within human anatomy. For example, control circuitry can determine a target location within a patient, such as an anatomical landmark, a location of a medical instrument, or any other location/target. In some embodiments, the control circuitry can determine the target location based on sensor data from a medical instrument that is disposed at least partially within the patient (e.g., a scope or another medical instrument).

At block 2306, the process 2300 can include determining a position and/or an orientation of one or more medical instruments. For example, control circuitry can determine a position and/or an orientation of one or more medical instruments based on sensor data from the one or more medical instruments. In some embodiments, the control circuitry can use one or more localization techniques to determine the position and/or the orientation. In examples, a position and orientation of a medical instrument can be referred to as a pose of the medical instrument.

At 2308, the process 2300 can include determining a plane that includes the target location. In one example, control circuitry can determine, based on sensor data of a medical instrument, a plane such that a heading of the medical instrument is normal to the plane. In another example, control circuitry can determine, based on sensor data of a medical instrument, a line between a distal end of a medical instrument and the target location and determine a plane such that the line is normal to the plane. In yet another example, control circuitry can determine, based on sensor data from a scope, a plane such that a heading of the scope is normal to the plane.

At 2310, the process 2300 can include updating an orientation of the plane or maintaining the orientation of the plane as an orientation of a medical instrument changes. In one example, control circuitry can update an orientation of a plane as an orientation of a needle changes such that a heading of the needle remains normal to the plane. In another example, control circuitry can maintain a constant/fixed orientation of a plane as an orientation of a needle changes. In yet another example, control circuitry can update an orientation of a plane as an orientation of a scope changes such that a heading of the scope remains normal to the plane.

At 2312, the process 2300 can include determining a projected position of a medical instrument on the plane. For example, control circuitry can determine a projected position of a medical instrument on the plane based on an orientation/position of the medical instrument. In examples, the projected position can be with respect to a tip of the medical instrument; however, the projected position can be with respect to other portions of the medical instrument, such as a back/proximal end of the medical instrument, a middle portion of the medical instrument, or another portion.

At block 2314, the process 2300 can include generating interface data representing one or more interface elements indicating a distance (e.g., projected deviation distance) between the projected position and the target location on the plane. For example, control circuitry can generate user interface data representing an instrument-alignment element representing an orientation of a medical instrument and/or an alignment marking representing the target location. In some embodiments, a positioning of the instrument-alignment element relative to the alignment marking and/or other features in the interface can indicate an alignment of the medical instrument to a target trajectory.

At block 2316, the process 2300 can include causing display of the one or more interface elements based on the interface data. For example, control circuitry can cause display of an interface via a display device, such as by sending user interface data to a display device associated with a control system. Further, a display device can display an interface based on interface data. In some instances, the interface presents a first interface element a distance from a center of a second interface element, wherein the distance is based on a distance between the projected position and the target location on the plane and/or an insertion distance between a tip of the medical instrument and the target location on the plane.

Figure 24:
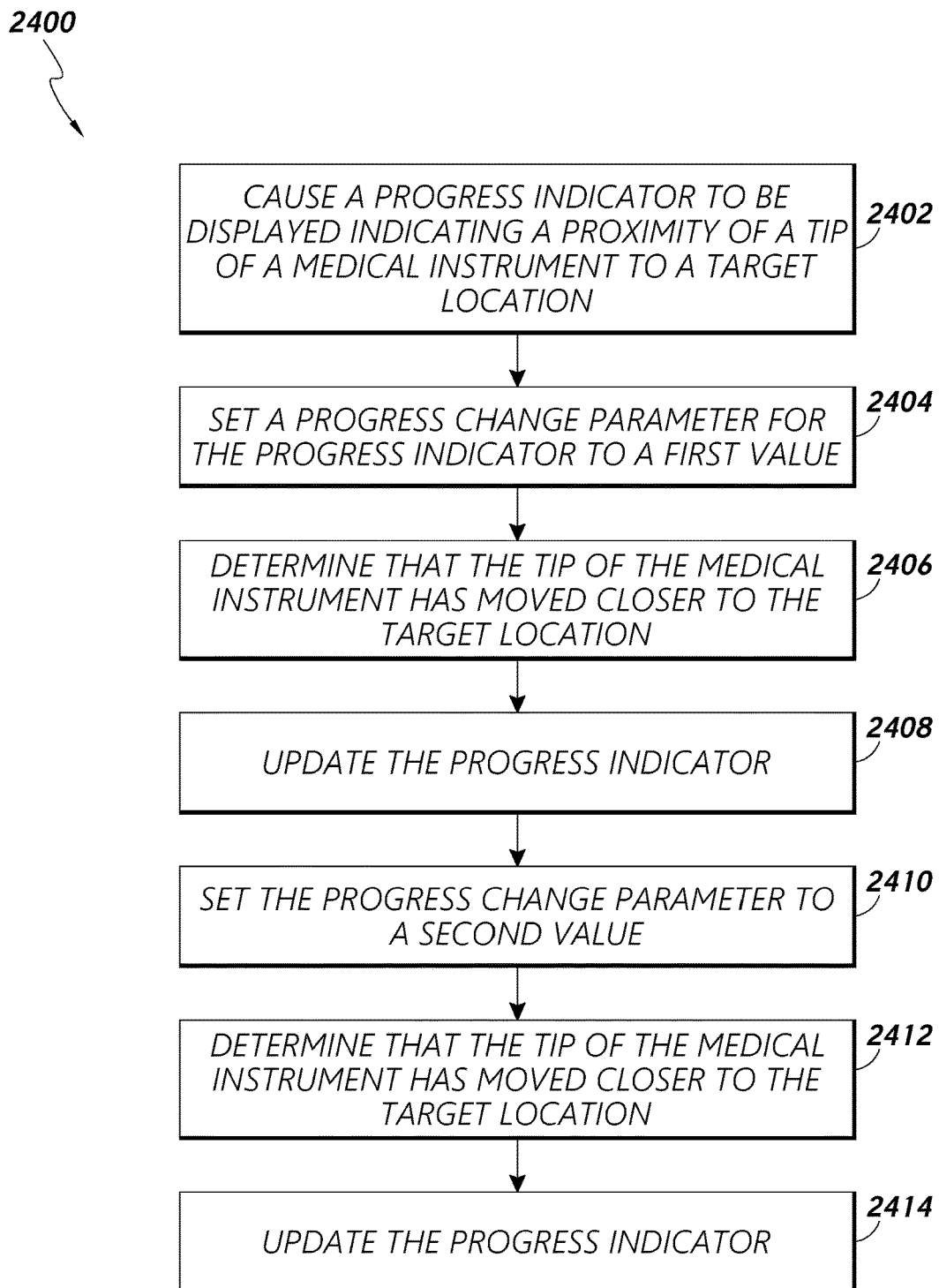
FIG. 24 illustrates an example flow diagram of a process for updating an amount of progress indicated for a unit of movement of a medical instrument in accordance with one or more embodiments.

FIG. 24 illustrates an example flow diagram of a process 2400 for updating an amount of progress indicated for a unit of movement of a medical instrument in accordance with one or more embodiments.

At block 2402, the process 2400 can include causing a progress indicator to be displayed indicating a proximity of a tip of the medical instrument to a target location and/or another other portion of the medical instrument to the target location. For example, control circuitry can cause display of a progress indicator via a display device, such as by sending interface data to a display device associated with a control system. Further, a display device can display a progress indicator based on interface data.

At block 2404, the process 2400 can include setting a progress change parameter for the progress indicator to a first value. For example, control circuitry can set a progress change parameter to a first value, wherein the progress change parameter is indicative of an amount of progress change of the progress indicator with respect to a unit of movement of the medical instrument (e.g., a unit of change in proximity of the tip of the medical instrument relative to a target location).

At block 2406, the process 2400 can include determining that the tip of the medical instrument has moved closer to the target location. For example, control circuitry can determine (a first time/instance) that the tip of the medical instrument has moved closer to the target location based on sensor data from the medical instrument. In examples, the control circuitry can determine that the medical instrument moved closer to the target location by a first amount.

At block 2408, the process 2400 can include updating the progress indicator. For example, control circuitry can update (a first time/instance) the progress indicator based on the progress change parameter and/or determining that the tip of the medical instrument has moved closer to the target location.

At block 2410, the process 2400 can include setting the progress change parameter to a second value. For example, control circuitry can set a progress change parameter to a second value based on determining that the tip of the medical instrument has moved closer to the target location. The second value can be associated with a greater amount of progress change of the progress indicator for the unit of movement of the medical instrument than the first value.

At block 2412, the process 2400 can include determining that the tip of the medical instrument has moved closer to the target location. For example, control circuitry can determine (a second time/instance) that the tip of the medical instrument has moved closer to the target location based on sensor data from the medical instrument. In examples, the control circuitry can determine that the medical instrument moved closer to the target location by the first amount.

At block 2414, the process 2400 can include updating the progress indicator. For example, control circuitry can update (a second time/instance) the progress indicator based on the progress change parameter and/or determining that the tip of the medical instrument has moved closer to the target location. In examples, the progress indicator can be updated to indicate a different amount of progress change than that indicated in block 2408.

Figure 25:
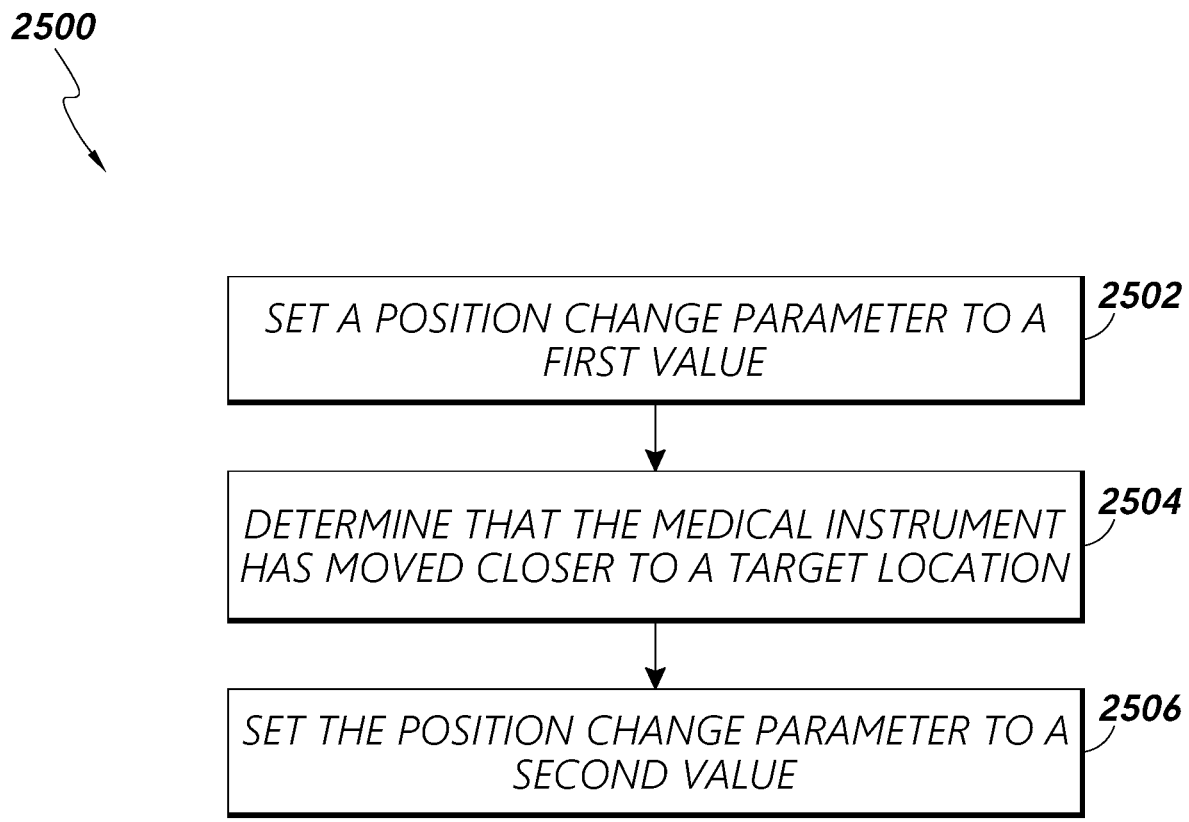
FIG. 25 illustrates an example flow diagram of a process for updating a position change parameter indicative of an amount of position change of an interface element for a unit of orientation/movement change of a medical instrument in accordance with one or more embodiments.

FIG. 25 illustrates an example flow diagram of a process 2500 for updating a position change parameter indicative of an amount of position change of an interface element for a unit of orientation/movement change of a medical instrument in accordance with one or more embodiments.

At block 2502, the process 2500 can include setting a position change parameter to a first value. For example, control circuitry can set a position change parameter to a first value, wherein the position change parameter can be indicative of an amount of position change of one or more interface elements within an interface with respect to a unit of movement/orientation change of the medical instrument.

At block 2504, the process 2500 can include determining that the medical instrument has moved closer to a target location. For example, control circuitry can determine that a tip of the medical instrument (e.g., needle) has moved closer to the target location based on sensor data from the medical instrument.

At block 2506, the process 2500 can include setting the position change parameter to a second value. For example, control circuitry can set the position change parameter to a second value, wherein the second value is associated with a greater amount of position change of the one or more interface elements within the interface for the unit of movement/orientation change of the medical instrument than the first value. In examples, the position change parameter can be set to the second value based on determining that the medical instrument has moved closer to the target location.

Figure 26:
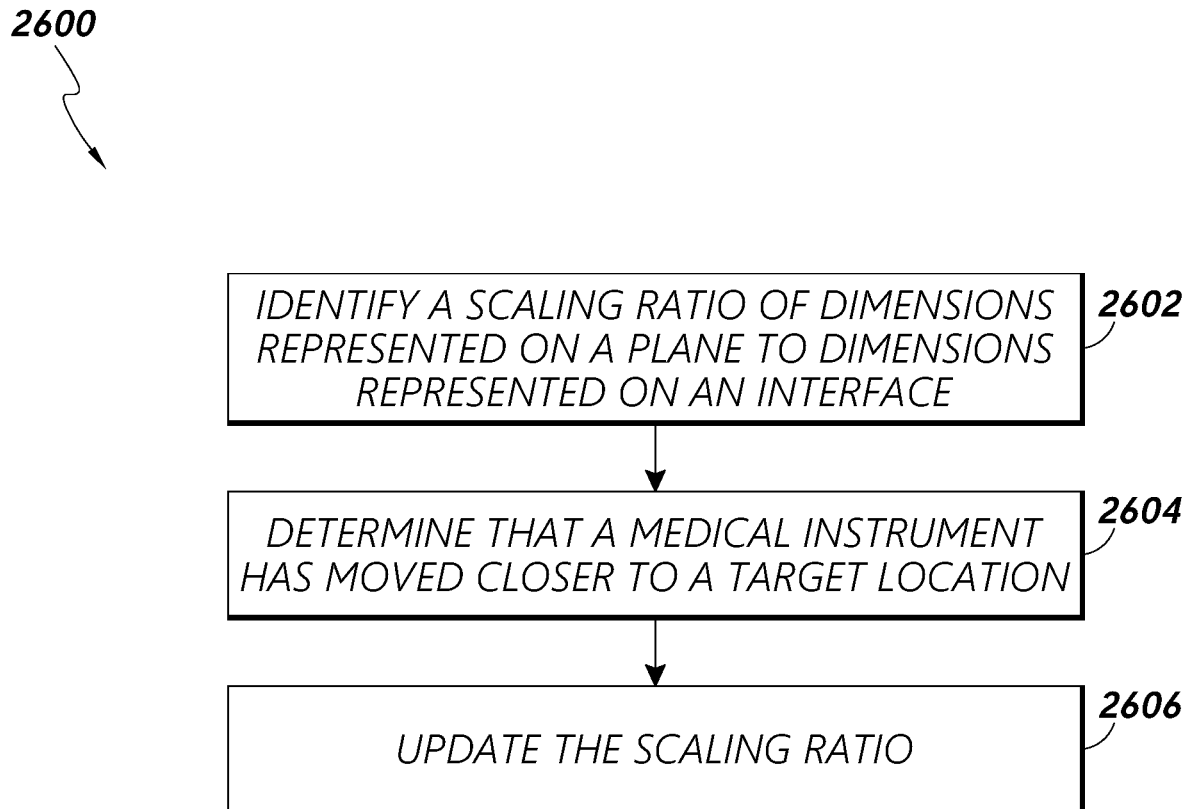
FIG. 26 an example flow diagram of a process for updating a scaling ratio of a plane to an interface in accordance with one or more embodiments.

FIG. 26 an example flow diagram of a process 2600 for updating a scaling ratio of a plane (e.g., target plane) to an interface in accordance with one or more embodiments.

At block 2602, the process 2600 can include identifying a scaling ratio of dimensions represented on a plane to dimensions represented on an interface. For example, control circuitry can determine a scaling ratio of dimensions for a target plane to dimensions for an interface.

At block 2604, the process 2600 can include determining that a medical instrument has moved closer to a target location. For example, control circuitry can determine that a tip of the medical instrument (e.g., needle) has moved closer to the target location based on sensor data from the medical instrument.

At block 2606, the process 2600 can include updating the scaling ratio. For example, control circuitry can update the scaling ratio based on the determining that the medical instrument has moved closer to the target location. The scaling ratio can be reduced or increased. The scaling ratio can be used to move/represent one or more interface elements within an interface.

Figure 27:
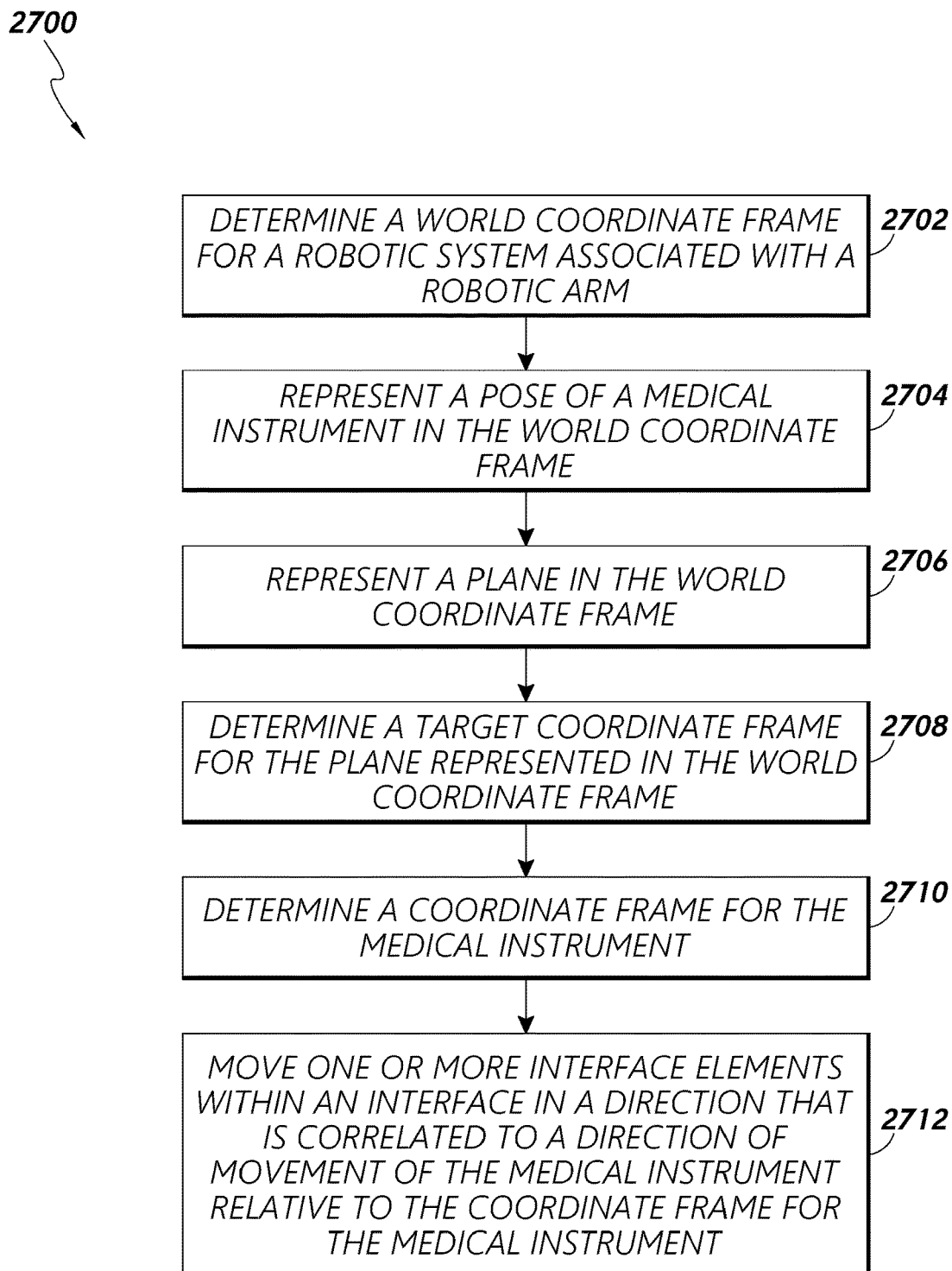
FIG. 27 illustrates an example flow diagram of a process for determining a coordinate frame for a medical instrument and/or correlating movement of an interface element to movement of the medical instrument in accordance with one or more embodiments.

FIG. 27 illustrates an example flow diagram of a process 2700 for determining a coordinate frame for a medical instrument and/or correlating movement of an interface element to movement of the medical instrument in accordance with one or more embodiments.

At block 2702, the process 2500 can include determining a world coordinate frame for a robotic system associated with a robotic arm. For example, a medical system can include a robotic arm coupled to an electromagnetic field generator and include a needle or other medical instrument configured to generate sensor data based on detection of electromagnetic fields from the electromagnetic field generator. Control circuitry can determine a coordinate frame for the robotic system.

At block 2704, the process 2700 can include representing a pose of a medical instrument in the world coordinate frame. For example, control circuitry can determine a pose of a needle based on sensor data from the needle and/or represent the pose of the needle within the world coordinate frame.

At block 2706, the process 2700 can include representing a plane in the world coordinate frame. For example, control circuitry can determine a target plane based on a target location and/or a pose of a needle and/or represent the target plane within the world coordinate frame.

At block 2708, the process 2700 can include determining a target coordinate frame for the plane represented in the world coordinate frame. For example, control circuitry can determine a target coordinate frame for a target plane based on a pose of a needle within the world coordinate frame.

At block 2710, the process 2700 can include determining a coordinate frame for the medical instrument. For example, control circuitry can determine a coordinate frame for a needle based on the target coordinate frame.

At block 2712, the process 2700 can include moving one or more interface elements within an interface in a direction that is correlated to a direction of movement of the medical instrument relative to the coordinate frame for the medical instrument. For example, control circuitry can cause one or more interface elements to move/update within an interface such that the one or more interface elements move in a direction that is correlated to a direction of movement of a needle relative to a coordinate frame for the needle. In examples, this can allow a user to view an interface element as moving left/right within the interface when tilting the needle left/right relative to the user, up/down within the interface when tilting the needle up/down relative to the user, and so on.

Figure 28:
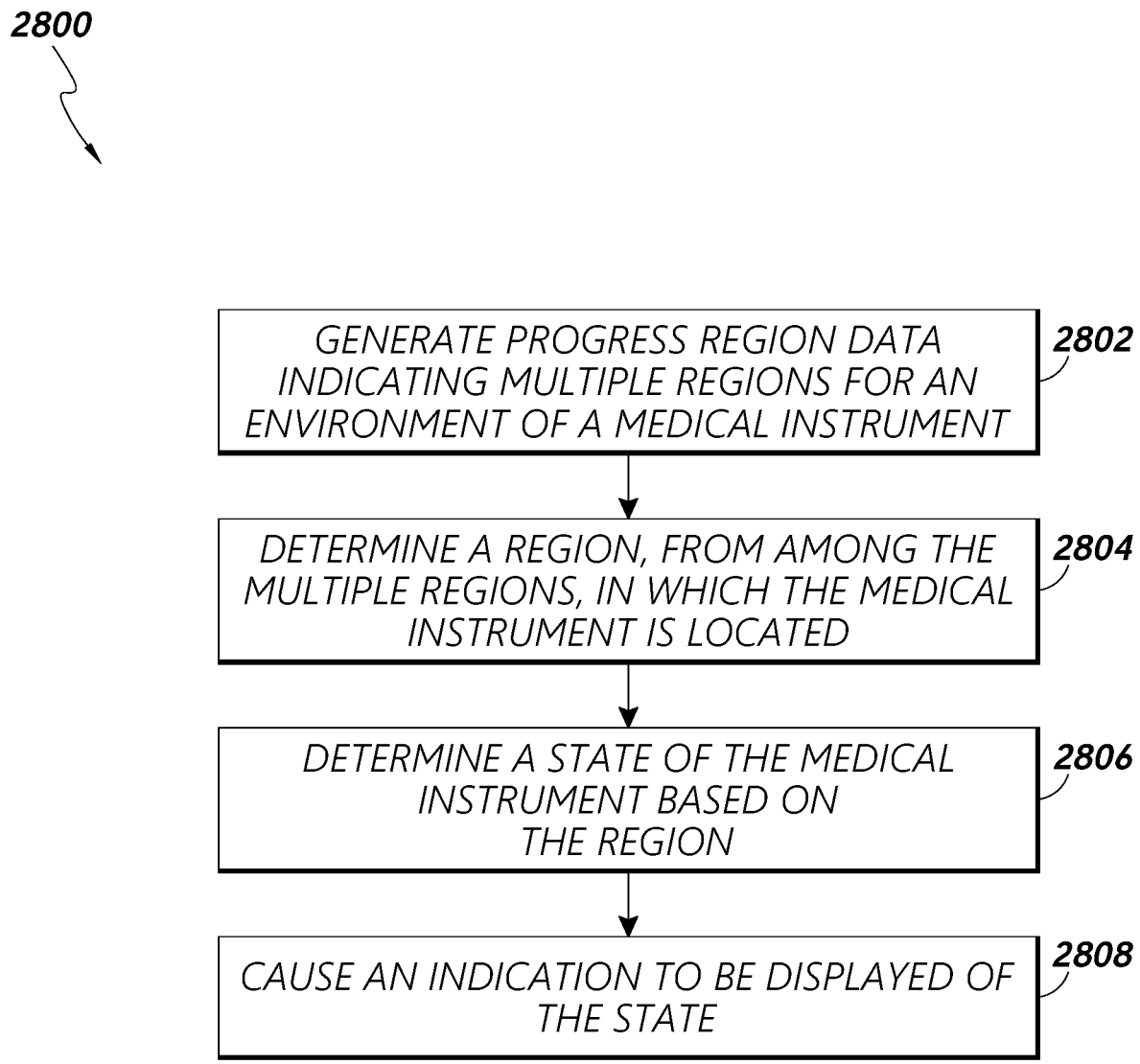
FIG. 28 illustrates an example flow diagram of a process for determining a state of a medical instrument based on a region in which the medical instrument is located in accordance with one or more embodiments.

FIG. 28 illustrates an example flow diagram of a process 2800 for determining a state of a medical instrument based on a region in which the medical instrument is located in accordance with one or more embodiments.

At block 2802, the process 2800 can include generating progress region data indicating multiple regions for an environment of a medical instrument. For example, control circuitry can generate progress region data based on sensor data from a needle and/or sensor data from a scope. The progress region data can indicate multiple regions within an environment, wherein each region can be associated with a state.

At block 2804, the process 2800 can include determining a region, from among the multiple regions, in which the medical instrument is located. For example, control circuitry can determine, based on sensor data from a needle and/or the progress region data, a region in which the needle is located.

At block 2806, the process 2800 can include determining a state of the medical instrument based on the region. For example, control circuitry can determine a state of a needle based on a region in which the needle is located. Such state can indicate if the needle is within a target region (e.g., associated with reaching a target location), if the needle is aligned with a target trajectory/pose, if the needle is outside the target region, if the needle has reached a target location, if the needle has passed the target location, and so on.

At block 2808, the process 2800 can include causing an indication to be displayed of the state. For example, control circuitry can cause display of a progress/alignment indication via a display device, such as by sending user interface data to a display device associated with a control system. Further, a display device can display a progress/alignment indication based on interface data. In examples, the state of the medical instrument and/or an indication of such state provided via an interface can be updated as the medical instrument changes position/orientation, such as by moving into a different region.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the disclosure should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A medical system comprising:
   a robotic system coupled to a device that is configured to generate a signal;
   a communication interface configured to receive sensor data from a medical instrument that is configured to access a human anatomy percutaneously, the sensor data being based at least in part on the signal; and
   control circuitry communicatively coupled to the communication interface and configured to:
      based at least in part on the sensor data, determine an orientation of the medical instrument;
      determine a target location within the human anatomy;
      determine a plane that includes the target location;
      based at least in part on the orientation of the medical instrument, determine a projected position of the medical instrument on the plane;
      generate interface data representing one or more interface elements indicating a distance between the projected position and the target location on the plane;
      determine a coordinate frame for the medical instrument based at least in part on a coordinate frame for the robotic system; and
      cause the one or more interface elements to move within an interface in a direction that is correlated to a direction of movement of the medical instrument relative to the coordinate frame for the medical instrument.

2. The medical system of claim 1, further comprising:
   an endoscope configured to access the target location via a lumen of the human anatomy, the endoscope including a sensor that is configured to provide additional sensor data to the communication interface;
   wherein the control circuitry is configured to determine the target location based at least in part on the additional sensor data.

3. The medical system of claim 1, wherein the control circuitry is configured to determine the plane such that a heading of the medical instrument is normal to the plane.

4. The medical system of claim 3, wherein the control circuitry is further configured to:
   update an orientation of the plane as the orientation of the medical instrument changes such that the heading of the medical instrument remains normal to the plane.

5. The medical system of claim 1, wherein the control circuitry is configured to determine the plane by determining a line between a distal end of the medical instrument and the target location and determining the plane such that the line is normal to the plane.

6. The medical system of claim 5, wherein the control circuitry is further configured to:
   maintain an orientation of the plane as the orientation of the medical instrument changes.

7. The medical system of claim 1, wherein the control circuitry is further configured to:
   set a position change parameter to a first value, the position change parameter being indicative of an amount of position change of the one or more interface elements within the interface with respect to a unit of movement of the medical instrument;
   determine that the medical instrument has moved closer to the target location; and
   set the position change parameter to a second value, the second value being associated with a greater amount of position change of the one or more interface elements within the interface for the unit of movement of the medical instrument than the first value.

8. The medical system of claim 1, wherein the control circuitry is further configured to:
   cause a progress indicator to be displayed indicating a proximity of the medical instrument to the target location;
   set a progress change parameter for the progress indicator to a first value, the progress change parameter being indicative of an amount of progress change of the progress indicator with respect to a unit of movement of the medical instrument;
   determine that the medical instrument has moved closer to the target location; and
   set the progress change parameter to a second value, the second value being associated with a greater amount of progress change of the progress indicator for the unit of movement of the medical instrument than the first value.

9. One or more non-transitory computer-readable media storing computer-executable instructions that, when executed by control circuitry, cause the control circuitry to perform operations comprising:
determining an orientation of a medical instrument that is configured to access a human anatomy percutaneously;
determining a target location within the human anatomy;
determining a plane that includes the target location;
based at least in part on the orientation of the medical instrument, determining a projected position of the medical instrument on the plane;
generating interface data representing one or more interface elements indicating a first distance between the projected position and the target location on the plane; and
displaying a first interface element of the one or more interface elements a second distance from a center of a second interface element of the one or more interface elements, the second distance being based at least in part on the first distance and an insertion distance between a tip of the medical instrument and the target location on the plane.

10. The one or more non-transitory computer-readable media of claim 9, wherein a heading of the medical instrument is normal to the plane.

11. The one or more non-transitory computer-readable media of claim 10, wherein the operations further comprise:
updating an orientation of the plane as the orientation of the medical instrument changes such that the heading of the medical instrument remains normal to the plane.

12. The one or more non-transitory computer-readable media of claim 9, wherein the plane is normal to a line between a distal end of the medical instrument and the target location.

13. The one or more non-transitory computer-readable media of claim 12, wherein the operations further comprise:
maintaining an orientation of the plane as the orientation of the medical instrument changes.

14. The one or more non-transitory computer-readable media of claim 9, wherein the operations further comprise:
causing a progress indicator to be displayed indicating a proximity of the medical instrument to the target location;
based at least in part on the medical instrument moving closer to the target location a first time by a first amount, updating the progress indicator by a second amount; and
based at least in part on the medical instrument moving closer to the target location a second time by the first amount, updating the progress indicator by a third amount that is greater than the first amount.

15. The one or more non-transitory computer-readable media of claim 9, wherein the operations further comprise:
generating progress region data indicating multiple regions for an environment of the medical instrument;
based at least in part on the progress region data, determining a region, from among the multiple regions, in which the medical instrument is located;
determining a state of the medical instrument based at least in part on the region; and
causing an indication to be displayed of the state.

16. A medical system comprising:
a communication interface configured to receive sensor data from a medical instrument that is configured to access a human anatomy percutaneously; and
control circuitry communicatively coupled to the communication interface and configured to:
based at least in part on the sensor data, determine an orientation of the medical instrument;
determine a target location within the human anatomy;
determine a plane that includes the target location;
based at least in part on the orientation of the medical instrument, determine a projected position of the medical instrument on the plane;
generate interface data representing one or more interface elements indicating a distance between the projected position and the target location on the plane;
set a position change parameter to a first value, the position change parameter being indicative of an amount of position change of the one or more interface elements within an interface with respect to a unit of movement of the medical instrument;
determine that the medical instrument has moved closer to the target location; and
set the position change parameter to a second value, the second value being associated with a greater amount of position change of the one or more interface elements within the interface for the unit of movement of the medical instrument than the first value.

17. The medical system of claim 16, wherein the control circuitry is configured to determine the plane such that a heading of the medical instrument is normal to the plane.

18. The medical system of claim 17, wherein the control circuitry is further configured to:
update an orientation of the plane as the orientation of the medical instrument changes such that the heading of the medical instrument remains normal to the plane.

19. The medical system of claim 16, wherein the control circuitry is configured to determine the plane by determining a line between a distal end of the medical instrument and the target location and determining the plane such that the line is normal to the plane.

20. A medical system comprising:
a communication interface configured to receive sensor data from a medical instrument that is configured to access a human anatomy percutaneously; and
control circuitry communicatively coupled to the communication interface and configured to:
based at least in part on the sensor data, determine an orientation of the medical instrument;
determine a target location within the human anatomy;
determine a plane that includes the target location;
based at least in part on the orientation of the medical instrument, determine a projected position of the medical instrument on the plane;
generate interface data representing one or more interface elements indicating a distance between the projected position and the target location on the plane;
cause a progress indicator to be displayed indicating a proximity of the medical instrument to the target location;
set a progress change parameter for the progress indicator to a first value, the progress change parameter being indicative of an amount of progress change of the progress indicator with respect to a unit of movement of the medical instrument;

determine that the medical instrument has moved closer to the target location; and set the progress change parameter to a second value, the second value being associated with a greater amount of progress change of the progress indicator for the unit of movement of the medical instrument than the first value.

21. The medical system of claim 20, wherein the control circuitry is configured to determine the plane such that a heading of the medical instrument is normal to the plane.

22. The medical system of claim 21, wherein the control circuitry is further configured to:

update an orientation of the plane as the orientation of the medical instrument changes such that the heading of the medical instrument remains normal to the plane.

23. The medical system of claim 20, wherein the control circuitry is configured to determine the plane by determining a line between a distal end of the medical instrument and the target location and determining the plane such that the line is normal to the plane.

24. One or more non-transitory computer-readable media storing computer-executable instructions that, when executed by control circuitry, cause the control circuitry to perform operations comprising:

determining an orientation of a medical instrument that is configured to access a human anatomy percutaneously;

determining a target location within the human anatomy;

determining a plane that includes the target location;

based at least in part on the orientation of the medical instrument, determining a projected position of the medical instrument on the plane;

generating interface data representing one or more interface elements indicating a first distance between the projected position and the target location on the plane;

causing a progress indicator to be displayed indicating a proximity of the medical instrument to the target location;

based at least in part on the medical instrument moving closer to the target location a first time by a first amount, updating the progress indicator by a second amount; and based at least in part on the medical instrument moving closer to the target location a second time by the first amount, updating the progress indicator by a third amount that is greater than the first amount.

25. The one or more non-transitory computer-readable media of claim 24, wherein the determining the plane includes determining the plane such that a heading of the medical instrument is normal to the plane.

26. The one or more non-transitory computer-readable media of claim 25, wherein the operations further comprise updating an orientation of the plane as the orientation of the medical instrument changes such that the heading of the medical instrument remains normal to the plane.

27. The one or more non-transitory computer-readable media of claim 24, wherein the determining the plane includes determining a line between a distal end of the medical instrument and the target location and determining the plane such that the line is normal to the plane.

28. One or more non-transitory computer-readable media storing computer-executable instructions that, when executed by control circuitry, cause the control circuitry to perform operations comprising:

determining an orientation of a medical instrument that is configured to access a human anatomy percutaneously;

determining a target location within the human anatomy;

determining a plane that includes the target location;

based at least in part on the orientation of the medical instrument, determining a projected position of the medical instrument on the plane;

generating interface data representing one or more interface elements indicating a first distance between the projected position and the target location on the plane;

generating progress region data indicating multiple regions for an environment of the medical instrument;

based at least in part on first sensor data and the progress region data, determining a region, from among the multiple regions, in which the medical instrument is located;

determining a state of the medical instrument based at least in part on the region; and causing an indication to be displayed of the state.

29. The one or more non-transitory computer-readable media of claim 28, wherein a heading of the medical instrument is normal to the plane.

30. The one or more non-transitory computer-readable media of claim 28, wherein a line between a distal end of the medical instrument and the target location is normal to the plane.

* * * * *